(12) United States Patent
Deckman et al.

(10) Patent No.: US 7,959,720 B2
(45) Date of Patent: Jun. 14, 2011

(54) LOW MESOPORE ADSORBENT CONTACTORS FOR USE IN SWING ADSORPTION PROCESSES

(75) Inventors: Harry W. Deckman, Clinton, NJ (US); Ronald R. Chance, Annandale, NJ (US); Edward W. Corcoran, Jr., Easton, PA (US); David L. Stern, Asbury, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 220 days.

(21) Appl. No.: 12/080,784

(22) Filed: Apr. 4, 2008

(65) Prior Publication Data

US 2008/0282892 A1 Nov. 20, 2008

Related U.S. Application Data

(60) Provisional application No. 60/930,827, filed on May 18, 2007.

(51) Int. Cl.
 *B01D 53/02* (2006.01)
(52) U.S. Cl. ............... 96/130; 96/108; 96/134; 96/140; 96/141; 95/96
(58) Field of Classification Search .................... 96/108, 96/130, 134, 140, 141; 95/96
See application file for complete search history.

(56) References Cited

U.S. PATENT DOCUMENTS

| | | | |
|---|---|---|---|
| 3,430,418 A | 3/1969 | Wagner | |
| 3,738,087 A | 6/1973 | McCombs | |
| 3,751,878 A | 8/1973 | Collins | |
| 3,801,513 A * | 4/1974 | Munzner et al. | 502/420 |
| 4,194,891 A * | 3/1980 | Earls et al. | 95/98 |
| 4,398,927 A * | 8/1983 | Asher et al. | 95/104 |
| 4,529,416 A | 7/1985 | Sircar et al. | |
| 4,578,089 A | 3/1986 | Richter et al. | |
| 4,589,888 A | 5/1986 | Hiscock et al. | |
| 4,671,893 A | 6/1987 | Pinto | |
| 4,770,676 A | 9/1988 | Sircar et al. | |
| 4,775,394 A | 10/1988 | Yamano et al. | |
| 4,775,396 A | 10/1988 | Rastelli et al. | |
| 4,784,672 A | 11/1988 | Sircar | |
| 4,801,308 A | 1/1989 | Keefer | |

(Continued)

FOREIGN PATENT DOCUMENTS

DE 3308304 9/1984

(Continued)

OTHER PUBLICATIONS

Johan van den Bergh, Weidong Zhu, Johan C. Groen, Freck Kapteijn, Jacob A. Moulijn, Kenji Yajima, Kunio Nakayama, Toshihiro Tomita, Shuichi Yoshida, Natural gas purification with a DDR zeolite membrane; permeation modeling with maxwell.

(Continued)

*Primary Examiner* — Robert J Hill, Jr.
*Assistant Examiner* — Christopher P Jones
(74) *Attorney, Agent, or Firm* — Bruce M. Bordelon

(57) ABSTRACT

The present invention relates to engineered structured adsorbent contactors for use in pressure swing adsorption and thermal swing adsorption processes. Preferably, the contactors contain engineered and substantially parallel flow channels wherein 20 volume percent or less of the open pore volume of the contactor, excluding the flow channels, is in the mesopore and macropore range.

23 Claims, 16 Drawing Sheets

U.S. PATENT DOCUMENTS

| | | | |
|---|---|---|---|
| 4,816,121 A | 3/1989 | Keefer | |
| 4,892,565 A | 1/1990 | Schmidt et al. | |
| 4,938,939 A | 7/1990 | Kuznicki | |
| 4,964,888 A * | 10/1990 | Miller | 95/95 |
| 4,968,329 A | 11/1990 | Keefer | |
| 4,988,490 A | 1/1991 | Nicholas et al. | |
| 5,082,473 A | 1/1992 | Keefer | |
| 5,185,139 A | 2/1993 | Krishnamurthy et al. | |
| 5,256,172 A | 10/1993 | Keefer | |
| 5,733,451 A | 3/1998 | Coellner et al. | |
| 5,840,099 A | 11/1998 | Kratz et al. | |
| 5,917,136 A | 6/1999 | Gaffney et al. | |
| 5,938,819 A | 8/1999 | Seery | |
| 6,024,781 A | 2/2000 | Bulow et al. | |
| 6,051,050 A | 4/2000 | Keefer et al. | |
| 6,056,804 A | 5/2000 | Keefer et al. | |
| 6,063,161 A | 5/2000 | Keefer et al. | |
| 6,068,682 A | 5/2000 | Kuznicki et al. | |
| 6,179,900 B1 | 1/2001 | Behling et al. | |
| 6,183,539 B1 | 2/2001 | Rode et al. | |
| 6,266,976 B1 | 7/2001 | Scharpf | |
| 6,280,503 B1 | 8/2001 | Mayorga et al. | |
| 6,299,994 B1 | 10/2001 | Towler et al. | |
| 6,406,523 B1 | 6/2002 | Connor et al. | |
| 6,409,801 B1 | 6/2002 | Shen et al. | |
| 6,451,095 B1 | 9/2002 | Keefer et al. | |
| 6,488,747 B1 | 12/2002 | Keefer et al. | |
| 6,497,750 B2 | 12/2002 | Butwell et al. | |
| 6,503,297 B1 | 1/2003 | Lu et al. | |
| 6,514,318 B2 | 2/2003 | Keefer | |
| 6,530,975 B2 | 3/2003 | Rode et al. | |
| 6,551,380 B1 | 4/2003 | Reddy et al. | |
| 6,565,635 B2 | 5/2003 | Keefer et al. | |
| 6,610,124 B1 | 8/2003 | Dolan et al. | |
| 6,629,525 B2 | 10/2003 | Hill et al. | |
| 6,630,012 B2 | 10/2003 | Wegeng et al. | |
| 6,692,545 B2 | 10/2003 | Hill et al. | |
| 6,651,658 B1 | 11/2003 | Hill et al. | |
| 6,691,702 B2 | 2/2004 | Appel et al. | |
| 6,742,507 B2 | 6/2004 | Keefer et al. | |
| 6,840,985 B2 | 1/2005 | Keefer | |
| 6,905,535 B2 | 5/2005 | Keefer et al. | |
| 6,921,597 B2 | 7/2005 | Keefer et al. | |
| 6,964,692 B2 | 11/2005 | Gittleman et al. | |
| 7,037,358 B2 | 5/2006 | Babicki et al. | |
| 7,041,272 B2 | 5/2006 | Keefer et al. | |
| 7,087,331 B2 | 8/2006 | Keefer et al. | |
| 7,094,275 B2 | 8/2006 | Keefer et al. | |
| 7,097,925 B2 | 8/2006 | Keefer | |
| 7,326,278 B2 * | 2/2008 | Butters et al. | 95/114 |
| 2002/0004157 A1 | 8/2002 | Keefer et al. | |
| 2002/0112479 A1 | 8/2002 | Keefer et al. | |
| 2002/0144597 A1 * | 10/2002 | Olson | 95/143 |
| 2002/0162452 A1 | 11/2002 | Butwell et al. | |
| 2003/0047071 A1 | 3/2003 | Dolan et al. | |
| 2003/0157390 A1 | 8/2003 | Keefer et al. | |
| 2005/0139072 A1 | 6/2005 | Landrum et al. | |
| 2005/0201929 A1 | 9/2005 | Hershkowitz et al. | |
| 2005/0203327 A1 | 9/2005 | Jovanovic et al. | |
| 2006/0165574 A1 | 7/2006 | Sayari | |
| 2006/0169142 A1 | 8/2006 | Rode et al. | |
| 2006/0174764 A1 | 8/2006 | Sundaram et al. | |
| 2006/0225569 A1 | 10/2006 | Schmidt et al. | |
| 2006/0235256 A1 | 10/2006 | Reddy | |
| 2006/0236862 A1 | 10/2006 | Golden et al. | |
| 2006/0257708 A1 | 11/2006 | Keefer et al. | |
| 2006/0280993 A1 | 12/2006 | Keefer et al. | |
| 2007/0163256 A1 | 7/2007 | McDonald et al. | |
| 2008/0148936 A1 | 6/2008 | Baksh | |

FOREIGN PATENT DOCUMENTS

| | | |
|---|---|---|
| DE | 3427804 | 4/1985 |
| DE | 100042601 | 10/1996 |
| EP | 0305919 | 8/1988 |
| EP | 0426937 A1 | 5/1990 |
| EP | 0595100 | 10/1993 |
| EP | 0145545 | 2/1998 |
| EP | 0862937 A2 | 9/1998 |
| EP | 1120149 A1 | 8/2001 |
| EP | 1291067 | 3/2003 |
| EP | 1674555 A1 | 6/2006 |
| EP | 1710008 | 10/2006 |
| EP | 1716906 A1 | 11/2006 |
| FR | 2794993 | 6/1999 |
| GB | 1238822 | 7/1970 |
| GB | 1283822 | 7/1970 |
| GB | 2155805 | 10/1985 |
| JP | 62046911 | 2/1987 |
| JP | 62105906 | 5/1987 |
| JP | 62225590 | 10/1987 |
| JP | 2135112 | 5/1990 |
| JP | 06327936 | 11/1994 |
| JP | 08131756 | 5/1996 |
| JP | 08131767 | 5/1996 |
| JP | 09187622 | 7/1997 |
| KR | 2000060821 | 10/2000 |
| KR | 2002003963 | 1/2002 |
| WO | 0076629 | 12/2000 |
| WO | WO 02/068093 A2 | 9/2002 |
| WO | 03063276 | 7/2003 |
| WO | WO 2004/000440 A1 | 12/2003 |
| WO | WO 2004/052812 A1 | 6/2004 |
| WO | WO 2006/052937 A2 | 5/2006 |
| WO | WO 2006/074343 A2 | 7/2006 |
| WO | WO 2006/133576 A1 | 12/2006 |
| WO | 2008050289 | 5/2008 |

OTHER PUBLICATIONS

Shuji Himeno, Toshihiro Tomita, Kenji Suzuki, Shuichi Yoshida, "Characterization and selectivity for methane and carbon dioxide adsorption on the all-silica DD3R zeolite"; Microporous and Mesoporous Materials, Elsevier Science Publishing, NY, US, vol. 98, No. 1-3, Dec. 7, 2006, pp. 62-69.

R. Krishna, J. M. van Baten, E. Garcia-Perez, S. Calero, "Difusión of CH4 and CO2 in MFI, CHA and DDR zeolites", Chemical Physics Letters, North-Holland, Amsterdam, vol. 429, No. 1-3, Sep. 29, 2006, pp. 219-224.

Jose A. Delgado, Maria A. Uguina, Jose L. Sotelo, Beatriz Ruiz, Jose M. Gomez; "Fixed-bed adsorption of carbon dioxide/methane mixtures on silicalite pellets," Adsorption (2006) 12:5-18.

Jose A. Delgado, Maria A. Uguina, Jose L. Sotelo, Beatriz Ruiz; "Modelling of the fixed-bed adsorption of methane/nitrogen mixtures on silicalite pellets," Separation and Purification Technology 50 (2006) 192-203.

Shivaji Sircar; "Separation of Methane and Carbon Dioxide Gas Mixtures by Pressure Swing Adsorption," Separation Science and Technology, 23(6 & 7) pp. 519-529, 1988.

Steven M. Kuznicki, Valerie A.A Bell, Sankar Nair, Hugh W. Hillhouse, Richard M. Jacubinas, Carola M. Braunbarth, Brian H. Toby, Michael Tsapatsis; "A titanosilicate molecular sieve with adjustable pores for size-selective adsorption of molecules," Nature, vol. 412, Aug. 16, 2001, pp. 720-724.

Jeremy Hart; "Separation of gases by adsorption," University of Bath, (1987).

D. M. Ruthven, Catherine Thaeron; "Performance of a parellel passage adsorbent contactor," Gas. Sep. Purif., vol. 10, No. 1, pp. 63-73, 1996.

D. M. Ruthven, C. Thaeron; Performance of a parellel passage adsorbent contactor, Separation and Purificatin Technology 12 (1997) pp. 43-60.

X. Shuai, S. Cheng, A. Meisen; "Simulation of pressure swing adsorption modules having laminated structure," Microporous Materials, 5 (1996) pp. 347-355.

\* cited by examiner

LOW MESOPORE ADSORBENT CONTACTORS FOR USE IN SWING ADSORPTION PROCESSES

This application claims the benefit of U.S. Provisional Application No. 60/930,827 filed May 18, 2007.

FIELD OF THE INVENTION

The present invention relates to engineered structured adsorbent contactors having a plurality of flow channels for use in pressure swing adsorption and thermal swing adsorption processes. The flow channels are preferably parallel flow channels wherein 20 volume percent or less of the open pore volume of the contactors, excluding the flow channels, is in the mesopore and macropore range.

BACKGROUND OF THE INVENTION

Gas separation is important in various industries and can typically be accomplished by flowing a mixture of gases over an adsorbent that preferentially adsorbs a more readily adsorbed component relative to a less readily adsorbed component of the mixture. One of the more important gas separation techniques is pressure swing adsorption (PSA). PSA processes rely on the fact that under pressure gases tend to be adsorbed within the pore structure of the microporous adsorbent materials or within the free volume of a polymeric material. The higher the pressure, the more gas is adsorbed. When the pressure is reduced, the gas is released, or desorbed. PSA processes can be used to separate gases in a mixture because different gases tend to fill the micropore or free volume of the adsorbent to different extents. If a gas mixture, such as natural gas, for example, is passed under pressure through a vessel containing polymeric or microporous adsorbent that fills with more nitrogen than it does methane, part or all of the nitrogen will stay in the sorbent bed, and the gas coming out of the vessel will be enriched in methane. When the bed reaches the end of its capacity to adsorb nitrogen, it can be regenerated by reducing the pressure, thereby releasing the adsorbed nitrogen. It is then ready for another cycle.

Another important gas separation technique is temperature swing adsorption (TSA). TSA processes also rely on the fact that under pressure gases tend to be adsorbed within the pore structure of the microporous adsorbent materials or within the free volume of a polymeric material. When the temperature of the adsorbent is increased, the gas is released, or desorbed. By cyclically swinging the temperature of adsorbent beds, TSA processes can be used to separate gases in a mixture when used with an adsorbent that selectively picks up one or more of the components in the gas mixture.

Adsorbents for PSA systems are usually very porous materials chosen because of their large surface area. Typical adsorbents are activated carbons, silica gels, aluminas and zeolites. In some cases a polymeric material can be used as the adsorbent material. Though the gas adsorbed on the interior surfaces of microporous materials may consist of a layer only one, or at most a few molecules thick, surface areas of several hundred square meters per gram enable the adsorption of a significant portion of the adsorbent's weight in gas.

Different molecules can have different affinities for adsorption into the pore structure or open volume of the adsorbent. This provides one mechanism for the adsorbent to discriminate between different gasses. In addition to their affinity for different gases, zeolites and some types of activated carbons, called carbon molecular sieves, may utilize their molecular sieve characteristics to exclude or slow the diffusion of some gas molecules into their structure. This provides a mechanism for selective adsorption based on the size of the molecules and usually restricts the ability of the larger molecules to be adsorbed. Either of these mechanisms can be employed to selectively fill the micropore structure of an adsorbent with one or more species from a multi-component gas mixture. The molecular species that selectively fill the micropores or open volume of the adsorbent are usually referred to as the "heavy" components and the molecular species that do not selectively fill the micropores or open volume of the adsorbent are usually referred to as the "light" components.

An early teaching of a PSA process having a multi-bed system is found in U.S. Pat. No. 3,430,418 wherein a system having at least four beds is described. This '418 patent describes a cyclic PSA processing sequence that includes in each bed: (1) higher pressure adsorption with release of product effluent from the product end of the bed; (2) co-current depressurization to intermediate pressure with release of void space gas from the product end thereof; (3) countercurrent depressurization to a lower pressure; (4) purge; and (5) repressurization. The void space gas released during the co-current depressurization step is commonly employed for pressure equalization purposes and to provide purge gas to a bed at its lower desorption pressure. Another conventional PSA processes using three sorbent beds is disclosed in U.S. Pat. No. 3,738,087. Conventional PSA processes are typically able to recover only one of the key components (i.e., light or heavy) at high purity and are unable to make a complete separation and separate both components with a high recovery. The light component usually has a low recovery factor. Recovery of the light component usually drops even lower when the feed gas is introduced at higher pressures (i.e., pressures above 500 psig).

For the recovery of a purified strongly adsorbed "heavy" component, an additional step is usually necessary, namely, rinsing of the bed with a heavy component to displace the light component from the bed prior to depressurization. The rinsing step is well known in the art. The problems associated with these processes are the following: (a) if the rinsing is complete and the light component is completely displaced from the bed, substantially pure heavy component can be obtained, but the adsorption front of the heavy component breaks through to the light component and the latter cannot be recovered at high purity; (b) if the displacement of the light component is incomplete, the typical concentration profile of the heavy component in the bed is not optimum and as such the bed is depressurized countercurrently to recover the heavy key component at the feed end, the light component still present in the bed reaches the feed end very rapidly and the purity of the heavy component drops. Therefore it is not practical in the prior art to obtain both key components at high purity in a single PSA unit.

The faster the beds perform steps to complete a cycle, the smaller the beds can be when used to process a given hourly feed gas flow. Several other approaches to reducing cycle time in PSA processes have emerged which use rotary valve technologies as disclosed in U.S. Pat. Nos. 4,801,308; 4,816,121; 4,968,329; 5,082,473; 5,256,172; 6,051,050; 6,056,80; 6,063,161; 6,406,523; 6,629,525; 6,651,658 and 6,691,702. A parallel channel (or parallel passage) contactor with a structured adsorbent is used to allow for efficient mass transfer in these rapid cycle pressure swing adsorption processes. Approaches to constructing parallel passage contactors with structured adsorbents have been disclosed in US20060169142 A1, US20060048648 A1, WO2006074343 A2, WO2006017940 A1, WO2005070518 A1, and WO2005032694 A1.

In a parallel channel contactor, the adsorbent lines the wall of the flow channel which can be formed from the space between parallel plates or the open path through a duct or tube. When parallel plates are used to form the parallel channel, a spacer may be present in the space of the parallel channel. An example of a spacer-less parallel passage contactor as provided in US20040197596 A1 and an example of a parallel passage contactor with a high density adsorbent structure is given in US20050129952A1. In all cases, the adsorbent used to line the parallel channel contains both mesopores and macropores.

Mesopores and macropores are known in the art to improve the mass transfer characteristics of adsorbents used in either a parallel channel contactor or conventional packed bed contactors. Improvements in mass transfer characteristics from the presence of mesopores and macropores in conventional packed bed contactors have been widely discussed. See for example U.S. Pat. Nos. 6,436,171 and 6,284,021. Improvements in mass transfer characteristics from the presence of mesopores and macropores in parallel channel contactors are discussed in EP1413348 A1. As such, the prior art teaches that a large number of mesopores and macropores are needed in an adsorbent particle or layer of adsorbent in order to have mass transfer characteristics good enough to operate a pressure swing adsorption cycle. The inventors hereof have unexpected found that adequate mass transfer characteristics can be attained without a significant amount of mesopores and/or macropores providing easy access to the micropore structure in the adsorbent where selective separation occurs.

While there are various teachings in the art with respect to new adsorbent materials, new and improved parallel channel contactors, and improved rapid cycle PSA equipment, none of these to date present a viable solution to the problem of producing good recovery of the light component and purity when the feed gas is at very high-pressure. This is a critical issue since natural gas is often produced at high pressures (500-7000 psi) and methane acts as a light component in the adsorption process. Many gas fields also contain significant levels of $H_2O$, $H_2S$, $CO_2$, $N_2$, mercaptans and/or heavy hydrocarbons that have to be removed to various degrees before the gas can be transported to market. It is preferred that as much of the acid gases $H_2S$ and $CO_2$ be removed from natural gas as possible. In all natural gas separations, methane is a valuable component and acts as a light component in swing adsorption processes. Small increases in recovery of this light component can result in significant improvements in process economics and also serve to prevent unwanted resource loss. It is desirable to recover more than 80 vol. %, preferably more than 90 vol. % of the methane when detrimental impurities are removed. While various processes exist for removing $CO_2$, $H_2S$, and $N_2$ from natural gas there remains a need for processes and materials that will perform this recovery more efficiently, at lower costs, and at higher hydrocarbon yields, particularly at higher methane yields.

Similarly, for other gaseous feed streams, the prior art describes several ways to recover high amounts of the heavy components in a heavy component rich "reject" stream, but cannot achieve as high a recovery of the light components in the light component rich product stream. This difference in recoveries becomes greater as the feed pressure increases.

SUMMARY OF THE INVENTION

In accordance with the present invention there is provided an adsorbent contactor for use in swing adsorption gas separation process units, comprising:

a) a gas inlet end; and
b) a gas outlet end;

wherein the gas inlet end and the gas outlet end are in fluid connection by a plurality of open flow channels wherein the surface of the open flow channels are comprised of an adsorbent material that has a selectivity for a first gas component over a second gas component of a gas mixture greater than 5, and wherein the contactor has less than about 20% of its open pore volume in pores with diameters greater than about 20 angstroms and less than about 1 micron.

In a preferred embodiment, the adsorbent contactor is a parallel channel contactor comprising structured (engineered) adsorbents in which substantially parallel flow channels are incorporated into the adsorbent structure.

In another embodiment, the open flow channels have a channel gap from about 5 to about 1000 microns.

In yet other embodiments, the adsorbent material is comprised of a material selected from the group consisting of zeolites, titanosilicates, ferrosilicates, stannosilicates, aluminophosphates (AlPOs), silicoaluminophosphates (SAPOs) and carbon molecular sieves.

In still another embodiment the adsorbent material is comprised of an 8-ring zeolite that has a Si to Al ratio of from about 1:1 to about 1000:1.

In another embodiment the contactor has less than about 10% of its open pore volume in pores with diameters greater than about 20 angstroms and less than about 1 micron.

In another embodiment the adsorbent contains an effective amount of a blocking agent occupying mesopores and macropores so that no more than about 20 vol. % of open pore volume of the adsorbent is in the mesopore or greater size range.

DETAILED DESCRIPTION OF THE INVENTION

Figure 1:
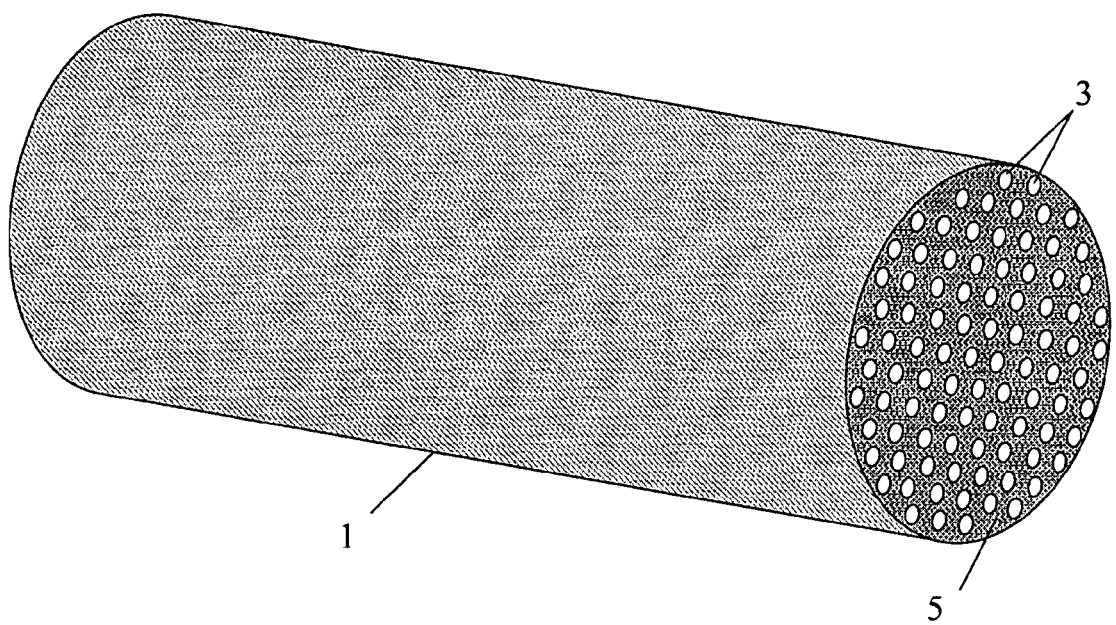
FIG. 1 hereof is a representation of one embodiment of a parallel channel contactor of the present invention in the form of a monolith directly formed from the microporous adsorbent of the present invention and containing a plurality of parallel channels.

The present invention is directed to adsorbent contactors for use in swing adsorption processes, which adsorbent contactors contain a plurality of flow channels and which contactors contain 20 vol. % or less, preferably 15 vol. % or less, more preferably 10 vol. % or less, and most preferably 5 vol. % or less of their open pore volume in pores in the mesopore and macropore size range. The term "adsorbent contactor" as utilized herein includes both structured and unstructured adsorbent contactors. The preferred contactors of the present invention are a type of structured adsorbent contactor entitled herein as "parallel channel contactors" for use in thermal swing adsorption (TSA) and various types of pressure swing adsorption processes including conventional pressure swing adsorption (PSA), and partial pressure swing or displacement purge adsorption (PPSA) technologies. These swing adsorption processes can be conducted with rapid cycles, in which case they are referred to as rapid cycle thermal swing adsorption (RCTSA), rapid cycle pressure swing adsorption (RCPSA), and rapid cycle partial pressure swing or displacement purge adsorption (RCPPSA) technologies. The term swing adsorption processes shall be taken to include all of these processes (i.e. TSA, PSA, PPSA, RCTSA, RCPSA, and RCPPSA) including combinations of these processes. Such processes require efficient contact of a gas mixture with a solid adsorbent material. It should also be noted that unless otherwise noted herein or by reference to specific "geometric shapes" (in which case would apply only to structured adsorbent contactors), that all preferred embodiments as described in this application, such as, but limited to, contactor voidages, separation components and efficiencies, operating conditions, preferred materials, etc., apply to both structured and unstructured adsorbent contactors of the present invention as described herein.

The structure of parallel channel contactors, including fixed surfaces on which the adsorbent or other active material is held, provides significant benefits over previous conventional gas separation methods, such as vessels containing adsorbent beads or extruded adsorbent particles. "Parallel channel contactors" are defined herein as a subset of adsorbent contactors comprising structured (engineered) adsorbents in which substantially parallel flow channels are incorporated into the adsorbent structure. These flow channels may be formed by a variety of means, many of which are described herein and in addition to the adsorbent material, the adsorbent structure may contain items such as, but not limited to, support materials, heat sink materials, void reduction components, etc., which are described more fully herein.

Swing adsorption processes are all well known to those having ordinary skill in the art and they can be applied to remove a variety of target gases from a wide variety of gas mixtures. It is possible to significantly improve the recovery percentage of the light component of a gas mixture by use of the present invention. The "light component" as utilized herein is taken to be the species, or molecular component, or components that are not preferentially taken up by the adsorbent in the adsorption step of the process. Conversely, the "heavy component" as utilized herein is taken to be the species, or molecular component, or components that are preferentially taken up by the adsorbent in the adsorption step of the process. With the contactors of the present invention, it has been unexpectedly discovered that total recovery of the light component achieved in the swing adsorption process can be greater than about 80 vol. %, more preferably greater than about 85 vol. %, even more preferably greater than about 90 vol. %, and most preferably greater than about 95 vol. % of the content of the light component introduced into the process. Recovery of the light component is defined as the time averaged molar flow rate of the light component in the product stream divided by the time averaged molar flow rate of the light component in the feedstream. Similarly, recovery of the heavy component is defined as the time averaged molar flow rate of the heavy component in the product stream divided by the time averaged molar flow rate of the heavy component in the feedstream.

The adsorbent contactors of the present invention contain a very low volume fraction of open mesopores and macropores. That is, the structured bed adsorbent contactors of the present invention contain less than about 20 vol. %, preferably less than about 15 vol. %, more preferably less than about 10 vol. %, and most preferably less than about 5 vol. % of their pore volume in open pores in the mesopore and macropore size range. Mesopores are defined by the IUPAC to be pores with sizes in the 20 to 500 angstrom size range. Macropores are defined herein to be pores with sizes greater than 500 angstroms and less than 1 micron. Because the flow channels are larger than 1 micron in size, they are not considered to be part of the macropore volume. By open pores we mean mesopores and macropores that are not occupied by a blocking agent and that are capable of being occupied, essentially non-selectively, by components of a gas mixture. Different test methods as described below are to be used to measure the volume fraction of open pores in a contactor depending on the structure of the contactor.

Open pore volume (in percent or volume percent) is defined herein as the volume of the pores in the adsorbent that are between 20 angstroms and 10,000 angstroms (1 micron) in diameter divided by the total volume of the contactor that is occupied by the adsorbent material including associated mesopores and macropores in the adsorbent structure. "Swept volumes" such as engineering flow channels as well as the volume occupied by any non-adsorbent material, such as but not limited to, support materials, blocking agents, thermal masses, etc., are not included in the amount of volume occupied by the adsorbent material.

The preferred test for determining the volume fraction of open mesopores and macropores of the contactor is defined as follows and involves an analysis of the isotherm of a condensable vapor adsorbed by the contactor. A liquid which has a vapor pressure greater than 0.1 torr at the temperature of the test is a suitable material that can be used to produce a condensable vapor. At 20° C., water, hexane, trimethylbenzene, toluene, xylenes, and isooctane have sufficiently high vapor pressures that they can be used as condensable vapors. In the adsorption branch of the isotherm (obtained by increasing the pressure of the condensable vapor), capillary condensation fills empty micropore, mesopore, and much of the empty macropore volume with liquid. In the desorption branch micropores, mesopores, and macropores pores filled with liquid are emptied. It is well known that there is a hysteresis between the adsorption and desorption branches of the isotherm. Detailed analysis of the adsorption isotherm relies in part on the Kelvin equation which is well known to those skilled in the art. The detailed analysis provides a measurement of the volume fraction of the mesopores and macropores in the structured adsorbent. The preferred measurement technique described in the following paragraphs derives from these principles.

Figure 17:
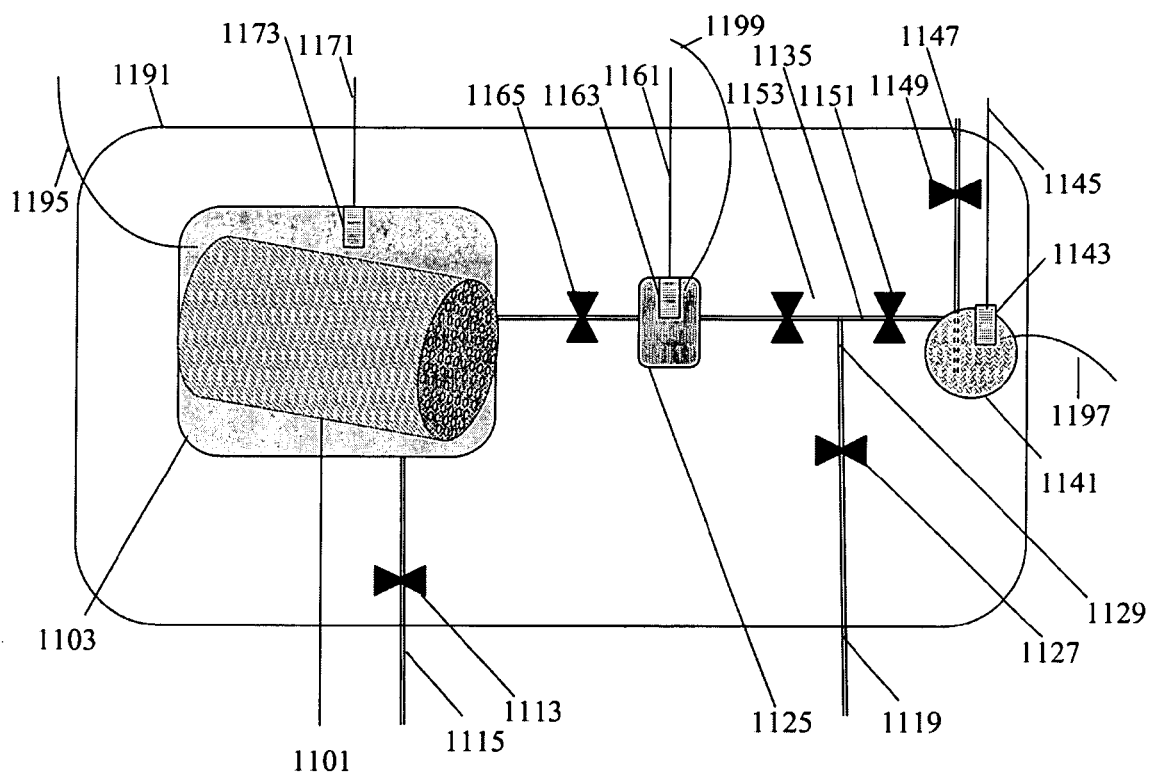
FIG. 17 hereof is a schematic representation of a preferred procedure for measuring the volume fraction of mesopores and macropores of adsorbent contactors of the present invention.

If a liquid blocking agent is not used in the contactor the procedure outlined in this paragraph is used to measure the volume of open mesopores and macropores of the subject contactor. This measurement is performed on either the entire contactor or a representative portion of the contactor. A representative portion of the contactor contains a least an entire cross section of the contactor and has a mass that is between 10% and 100% of the mass of the contactor. Additionally, the mass of the contactor used in this measurement should be more than 50 grams. A preferred procedure is represented in FIG. 17 hereof wherein the initial steps of the procedure involve placing the contactor 1101 or a representative portion of the contactor, into a sealable vacuum tight container 1103 and evacuating the container. Chamber 1103 is designed so that the volume defined by the exterior surface of the contactor 1101 is at least 50% of the interior volume of the chamber. The vacuum tight container is equipped with a pressure transducer 1173 and a cable 1171 to power the transducer and transmit the signal generated. The transducer is chosen so that it can measure pressures with an accuracy of 0.01 torr. A suitable transducer for such a measurement is a capacitance manometer.

The vacuum tight vessel 1103 and all of the equipment used to evacuate the vessel and fill the vessel with known quantities of the condensable vapor are located in an isothermal chamber 1191. The isothermal chamber 1191 is kept at a temperature of 30.00 (+/−0.01)° C. To make sure that the vacuum tight container 1103 and vessels 1125 and 1141 are at a constant temperature before and after each step used to dose hexane into the contactor their temperature is monitored with thermocouples 1195, 1197 and 1199 that can be read with a resolution of 0.01° C. The thermocouple readings may differ by a small amount because the accuracy of thermocouple readings is generally 0.2° C. The important issue is that before and after each hexane dosing step the readings of thermocouples 1195, 1197 and 1199 remain constant to within +/−0.01° C. Initially all valves (1113, 1127, 1149, 1151, 1153 and 1165) in the system are closed. It is preferred that the valves be air actuated (instead of solenoid activated) so that do not heat the gas or piping when they are opened. Before the measurement begins the equipment used to fill hexane vapor (chosen as an example of a condensable vapor at 30° C.) into vessel 1103 must be leak checked. This is done by opening valves 1127, 1151, and 1153, allowing line 1119 that is attached to a vacuum pump to evacuate vessels 1125 and 1141.

Pressure in these vessels is measured with transducers 1163 and 1143 which have cables 1161 and 1145, respectively to power them and transmit the signals generated. The transducer is chosen so that they can measure pressures with an accuracy of 0.01 torr and suitable transducers are capacitance manometers. The vessel 1125 and 1141 are evacuated so that transducers 1163 and 1143 read a pressure of less than 0.03 torr. Valve 1127 is then closed and the system is considered leak tight if the pressure recorded by transducers 1163 and 1143 does not rise by more than 0.02 torr over a three hour period. At this point valves 1153 and 1151 are closed and the evacuated vessel 1141 is filled with hexane through line 1147 by opening valve 1149. Line 1147 was originally filled with liquid hexane. To stop the filling of reservoir 1141, valve 1149 is shut.

A procedure is then instituted to remove any impurity gases that may have been carried into vessel 1141 during the hexane filling step. Gases are removed by opening valve 1127 and then opening valve 1151 for a period of 2 minutes dropping the pressure in vessel 1141 thus allowing the hexane to boil. This degassing procedure is repeated five times before the hexane in vessel 1141 can be used. At this point valve 1153 is closed and valve 1127 is open, thus evacuating line 1129. Valve 1153 is then opened pulling a vacuum on vessel 1125. Adsorbed molecules in the contactor or a representative piece of the contactor 1101 in chamber 1103 are then removed by opening valve 1113. This allows line 1115 that is attached to a vacuum pump to evacuate chamber 1103. The evacuation procedure continues until the pressure in the vessel 1103 falls below 0.03 torr. At this point valve 1113 is closed and the pressure in the chamber is monitored for an hour. If the pressure in the chamber rises by more than 0.02 torr during this time period then the evacuation procedure is repeated. If the evacuation procedure has to be repeated more than ten times then alternative means of removing molecules from the contactor 1101 should be employed (such as heating the contactor). After adsorbed molecules have been successfully removed from the contactor, valves 1127 and 1153 are closed.

Valve 1151 is then opened allowing line 1129 to fill with hexane vapor. Under the conditions of the test this will be approximately 187 torr of hexane vapor. Valve 1151 is then closed and valve 1153 is opened allowing the vapor in the line to expand into vessel 1125. Because of the difference in volume between line 1129 and vessel 1125 the pressure measured by transducer 1163 will be less than 5 torr. Valve 1153 is then closed and this filling procedure is repeated until the pressure in vessel 1125 is approximately 5 torr. At this point valve 1165 is opened to dose the contactor 1101 with hexane vapor. The pressure in vessel 1125 drops because of gas expansion into chamber 1103 and possible adsorption of molecules of hexane into micropores of the contactor. After the pressure in vessel 1125 stops dropping and stabilizes, the pressure is recorded and the number of moles of hexane transferred into chamber 1103 is computed from the ideal gas law. This requires knowledge (previous measurement) of the interior volume of vessel 1125 and its associated piping.

The moles of gas transferred into vessel 1103 that would be needed to fill the gas space inside it are computed using the ideal gas law with the pressure measured by transducer 1173. Again, knowledge of the available gas space in chamber 1103 is required for the calculation. The interior volume of chamber 1103 is known (previous measurement) and the available gas volume is computed by subtracting from the interior volume of vessel 1103 the exterior volume of the contactor and adding back the volume of the flow channels in the contactor. Errors in knowledge of the exterior volume of the contactor or the volume of the flow channels will not significantly affect the measurement of the total open mesopore and macropore volumes. The quantity which is the difference between the exterior volume of the contactor and the volume of the flow channels only has to be known to an accuracy of 20%.

The moles of gas adsorbed by the contactor is then the difference between the moles of gas transferred and the moles of gas required to fill the available gas space in vessel 1103 and its associated piping. After completing this dosing step and the evaluation of the moles of gas adsorbed in the contactor 1101 valve 1165 is closed and pressure in vessel 1125 is increased 5 more torr by repeating the procedure originally used to fill it with hexane vapor. The dosing step to adsorb more molecules into the contactor is then repeated. The filling and dosing steps continue to be repeated until the pressure in vessel 1125 at the end of a dosing step is within +/-2.5 torr of 15% of the reading of pressure transducer 1143. This range is expected to be between 25.5 and 30.5 torr. From this point onward in the procedure the additional moles of hexane that are adsorbed in the contactor are considered to fill the mesopores and macropores. The filling and dosing steps are continued until the pressure in chamber 1103 housing the contactor exceeds 95% of the pressure read by transducer 1143.

Filling and dosing steps are continued in a manner such that the pressure in vessel 1125 is only increased by 1 torr in each filling step. When the pressure read by transducer 1173 at the end of a dosing step exceeds 98.5% of the pressure read by transducer 1143 the pressure increase in vessel 1125 during a filling step is decreased to 0.5 torr. When the pressure read by transducer 1173 at the end of a dosing step exceeds 99.25% of the pressure read by transducer 1143 the pressure increase in vessel 1125 during a filling step is decreased to 0.05 torr. The filling and dosing steps are then continued until the pressure read by the transducer 1173 at the end of a dosing step exceeds 99.6% of the pressure read by transducer 1143. The pressure at which the experiment is ended is expected to be approximately 186.4 torr. The total number of moles adsorbed by the contactor from the point at which at the end of a dosing step transducer 1161 was in a range between within +/-2.5 torr of 15% of the reading of pressure transducer 1143 and the point at which the pressure read by the transducer 1173 at the end of a dosing step exceeded 99.6% of the pressure read by transducer 1143 is the total number of moles of hexane adsorbed in the mesopore and macropore volume of the contactor. The volume of the open mesopores and macropores in the contactor is then determined by multiplying this number of moles by the molar volume of hexane. The open pore volume as expressed in a volume fraction as used herein is then obtained by dividing the volume of open mesopores and macropores determined by this test by the total volume of the contactor that is occupied by the adsorbent material as defined prior. Although the open pore volume for the contactor is determined by the test procedure described above, scanning electron microscopy may be used to further confirm the relative volume of mesopores and macropores in the sample. When scanning electron microscopy is used the surface as well as a cross section of the contactor should be imaged.

If a liquid material is used as a blocking agent in the formulation of the contactor, and the contactor is operated under conditions where the pores remain substantially fully filled with liquid no assay as described above is required to determine the open pore volume of the contactor. In this contactor configuration, the mesopores and macropores of the contactor will remain filled with liquid as long as the liquid remains condensable at the operating temperature of the contactor and the feed flowing into the contactor is fully saturated with the vapor of the liquid at the inlet temperature and pressure. In this case, there is no open mesopore or macropore volume in the contactor because it has all been filled-in by the condensable vapor. If under operating conditions (i.e., inlet temperature and pressure) the feed flowing into the contactor is only partially saturated with the vapor of the liquid then some fraction of the mesopore or macropore volume will remain open. The degree of saturation is characterized by a liquid activity ($a_{liquid}$) that is the ratio of the partial pressure of the vapor of the liquid in the flowing gas stream to the saturated vapor pressure of the liquid at the temperature of the contactor (i.e. $P_i/P_{sat}$). The amount of open mesopore and macropore volume increases as the partial pressure of the condensable liquid in the feed decreases. To determine the volume of mesopores and macropores under operating conditions the liquid material used in the formulation of the contactor is removed from the mesopores and macropores of the contactor by drying. Liquid can be dried-out of the mesopores and macropores of the contactor by heating it in a sealed container while drawing a vacuum or by heating it while passing a substantially pure purge gas, such as He, over the contactor. Once liquid has been removed from the mesopores and macropores of the contactor, the assay method previously described can be conducted. In this assay the amount of gas adsorbed by the contactor is plotted against the hexane activity ($a_{hexane}$) which is the hexane pressure at the end of an adsorption step divided by the saturated hexane vapor pressure. The amount of open mesopores and macropores that would be expected in operation is then determined from the cumulative number of moles of hexane adsorbed between the point at which the hexane activity exceeds $a_{liquid}$ and the point at which the experiment is terminated (i.e., when the pressure read by the transducer 1173 at the end of a dosing step exceeds 99.6% of the pressure read by transducer 1143). Again the molar volume of hexane is used to compute the actual open mesopore and macropore volume. The open pore volume as expressed in a volume fraction as used herein is then obtained by dividing the volume of open mesopores and macropores determined by this test by the total volume of the contactor that is occupied by the adsorbent material as defined prior.

In equilibrium controlled swing adsorption processes most of the selectivity is imparted by the equilibrium adsorption properties of the adsorbent, and the competitive adsorption isotherm of the light product in the micropores or free volume of the adsorbent is not favored. In a kinetically controlled swing adsorption processes most of the selectivity is imparted by the diffusional properties of the adsorbent and the transport diffusion coefficient in the micropores and free volume of the adsorbent of the light species is less than that of the heavier species. Also, in kinetically controlled swing adsorption processes with microporous adsorbents the diffusional selectivity can arise from diffusion differences in the micropores of the adsorbent or from a selective diffusional surface resistance in the crystals or particles that make-up the adsorbent.

It will be understood that the term PSA, unless preceded by the term "conventional" or "rapid cycle" refers collectively to all pressure swing adsorption processes including conventional PSA, RCPSA and PPSA. In PSA processes, a gaseous mixture is conducted under pressure for a period of time over a first bed of a solid sorbent that is selective, or relatively selective, for one or more components, usually regarded as a contaminant, that is to be removed from the gaseous mixture. The components that are selectively adsorbed are referred to as the heavy component and the weakly adsorbed components that pass through the bed are referred to as the light components. It is possible to remove two or more contaminants simultaneously but for convenience, the component or components, that are to be removed by selective adsorption will be referred to in the singular and referred to as a contaminant or heavy component.

Unless otherwise noted, the term "selectivity" as used herein is based on binary (pairwise) comparison of the molar concentration of components in the feed stream and the total number of moles of these components adsorbed by the particular adsorbent during the adsorption step of the process cycle under the specific system operating conditions and feedstream composition. For a feed containing component A, component B, as well as additional components, an adsorbent that has a greater "selectivity" for component A than component B will have at the end of the adsorption step of the swing adsorption process cycle a ratio:

$U_A$=(total moles of $A$ in the adsorbent)/(molar concentration of $A$ in the feed)

that is greater than the ratio:

$U_B$=(total moles of $B$ in the adsorbent)/(molar concentration of $B$ in the feed)

Where $U_A$ is the "Adsorption Uptake of component A" and $U_B$ is the "Adsorption Uptake of component B".
Therefore for an adsorbent having a selectivity for component A over component B that is greater than one:

Selectivity=$U_A/U_B$(where $U_A > U_B$).

Amongst a comparison of different components in the feed, the component with the smallest ratio of the total moles picked up in the adsorbent to its molar concentration in the feed is the lightest component in the swing adsorption process. This means that the molar concentration of the lightest component in the stream coming out during the adsorption step is greater than the molar concentration of that lightest component in the feed. The adsorbent contactors of the present invention have a selectivity for a first component (e.g., component A) over a second component (e.g., component B) of at least 5, more preferably a selectivity for a first component over a second component of at least 10, and most preferably a selectivity for a first component over a second component of at least 25.

Examples of components are molecules such as molecular nitrogen, $N_2$, or compounds, such as carbon dioxide, $CO_2$, and methane, $CH_4$. In a preferred embodiment of the present invention, the adsorbent contactor has a selectivity for $CO_2$ over $CH_4$ of at least 5, more preferably a selectivity for $CO_2$ over $CH_4$ of at least 10, and most preferably a selectivity for $CO_2$ over $CH_4$ of at least 25. In another preferred embodiment of the present invention, the adsorbent contactor has a selectivity for $N_2$ over $CH_4$ of at least 5, more preferably a selectivity for $N_2$ over $CH_4$ of at least 10, and most preferably a selectivity for $N_2$ over $CH_4$ of at least 25. In yet another preferred embodiment of the present invention, the adsorbent contactor has a selectivity for $H_2S$ over $CH_4$ of at least 5, more preferably a selectivity for $H_2S$ over $CH_4$ of at least 10, and most preferably a selectivity for $H_2S$ over $CH_4$ of at least 25.

In a preferred embodiment of the present invention, the adsorbent has a "kinetic selectivity" for two or more gas components. As used herein, the term "kinetic selectivity" is defined as the ratio of single component diffusion coefficients, D (in m²/sec), for two different species. These single component diffusion coefficients are also known as the Stefan-Maxwell transport diffusion coefficients that are measured for a given adsorbent for a given pure gas component. Therefore, for example, the kinetic selectivity for a particular adsorbent for component A with respect to component B would be equal to $D_A/D_B$. The single component diffusion coefficients for a material can be determined by tests well known in the adsorptive materials art. The preferred way to measure the kinetic diffusion coefficient is with a frequency response technique described by Reyes et al. in "Frequency Modulation Methods for Diffusion and Adsorption Measurements in Porous Solids", J. Phys. Chem. B. 101, pages 614-622, 1997. In a kinetically controlled separation it is preferred that kinetic selectivity (i.e., $D_A/D_B$) of the selected adsorbent for the first component (e.g., Component A) with respect to the second component (e.g., Component B) be greater than 5, more preferably greater than 20, even more preferably greater than 50.

In another preferred embodiment of the present invention, the adsorbent has an "equilibrium selectivity" for two or more gas components. As used herein, the term "equilibrium selectivity" is defined in terms of the slope of the single component uptake into the adsorbent (in μmole/g) vs. pressure (in torr) in the linear portion, or "Henry's regime", of the uptake isotherm for a given adsorbent for a given pure component. The slope of this line is called herein the Henrys constant or "equilibrium uptake slope", or "H". The "equilibrium selectivity" is defined in terms of a binary (or pairwise) comparison of the Henrys constants of different components in the feed for a particular adsorbent. Therefore, for example, the equilibrium selectivity for a particular adsorbent for component A with respect to component B would be $H_A/H_B$. It is preferred that in an equilibrium controlled separation the equilibrium selectivity (i.e., $H_A/H_B$) of the selected adsorbent for the first component (e.g., Component A) with respect to the second component (e.g., Component B) be greater than 5, more preferably greater than 20, even more preferably greater than 50.

In the PSA process, the gaseous mixture is passed over a first adsorption bed in a first vessel and a light component enriched product stream emerges from the bed depleted in the contaminant, or heavy component, which remains sorbed in the bed. After a predetermined time or, alternatively when a break-through of the contaminant or heavy component is observed, the flow of the gaseous mixture is switched to a second adsorption bed in a second vessel for the purification to continue. While the second bed is in adsorption service, the sorbed contaminant, or heavy component, is removed from the first adsorption bed by a reduction in pressure. In some embodiments, the reduction in pressure is accompanied by a reverse flow of gas to assist in desorbing the heavy component. As the pressure in the vessels is reduced, the heavy component previously adsorbed in the bed is progressively desorbed to a heavy component enriched product stream. When desorption is complete, the sorbent bed may be purged with an inert gas stream, e.g., nitrogen or a purified stream of process gas. Purging may also be facilitated by the use of a higher temperature purge gas stream.

After the first bed has been regenerated so that it is again ready for adsorption service, the flow of the gaseous mixture is switched from the second bed to the first bed, and the second bed is regenerated. The total cycle time is the length of time from when the gaseous mixture is first conducted to the first bed in a first cycle to the time when the gaseous mixture is first conducted to the first bed in the immediately succeeding cycle, i.e., after a single regeneration of the first bed. The use of third, fourth, fifth, etc. vessels in addition to the second vessel can serve to increase cycle time when the adsorption cycle time for the bed is shorter than the cycle times for the desorption & purging cycles for the bed.

Conventional PSA processes suffer from several inherent disadvantages. For example, conventional PSA units are typically more costly to build and operate and are significantly larger in size for the same amount of target gas that needs to be recovered from a target-gas containing gas stream, such as natural gas, as compared to RCPSA. Also, a conventional PSA unit will generally have cycle times in excess of one minute, typically in excess of 2 to 4 minutes due to time limitations required to allow diffusion of the components through the larger beds utilized in conventional PSA and the equipment configuration involved. In contrast, RCPSA generally has a total cycle times of less than one minute. The total cycle times of RCPSA may be less than 30 seconds, preferably less than 15 seconds, more preferably less than 10 seconds, even more preferably less than 5 seconds, and even more preferably less than 1 second. Further, the rapid cycle pressure swing adsorption units can make use of substantially different sorbents, such as, but not limited to, structured materials such as monoliths, laminates, and hollow fibers.

RCPSA can enable a significant increase in process intensification (e.g., higher operating frequencies and gas flow velocities) when compared to conventional PSA. RCPSA typically utilizes a rotary valving system to conduct the gas flow through a rotary adsorber module that contains a number of separate adsorbent bed compartments or "tubes", each of which is successively cycled through the sorption and desorption steps as the rotary module completes the cycle of operations. The rotary sorber module is normally comprised of multiple tubes held between two seal plates on either end of the rotary sorber module wherein the seal plates are in contact with a stator comprised of separate manifolds wherein the inlet gas is conducted to the RCPSA tubes and the processed purified product gas and the tail gas exiting the RCPSA tubes are conducted away from the rotary sorber module. By suitable arrangement of the seal plates and manifolds, a number of individual compartments or tubes may pass through the characteristic steps of the complete cycle at any given time. In contrast, with conventional PSA, the flow and pressure variations, required for the RCPSA sorption/desorption cycle, changes in a number of separate increments on the order of seconds per cycle, which smoothes out the pressure and flow rate pulsations encountered by the compression and valving machinery. In this form, the RCPSA module includes valving elements angularly spaced around the circular path taken by the rotating sorption module so that each compartment is successively passed to a gas flow path in the appropriate direction and pressure to achieve one of the incremental pressure/flow direction steps in the complete RCPSA cycle. One key advantage of the RCPSA technology is a significantly more efficient use of the adsorbent material. The quantity of adsorbent required with RCPSA technology can be only a fraction of that required for conventional PSA technology to achieve the same separation quantities and qualities. As a result, the footprint, investment, and the amount of active adsorbent required for RCPSA is typically significantly lower than that for a conventional PSA unit processing an equivalent amount of gas.

The present invention may be used in PPSA, RCPSA or hybrid PPSA or RCPPSA processes where a gas or liquid is purged through the bed to help desorb molecules. In a PPSA process, desorption of the adsorbed species is accomplished by passing a gas or liquid through the contactor to desorb molecules taken up during an adsorption step. An example of a gas that may be used is steam. In hybrid PPSA processes, the desorption of molecules from the contactor is accomplished by use of a thermal or pressure swing and part of the desorption is accomplished with a purge.

Improvements in the recovery of the light component are especially important for processes used to remove impurities from natural gas streams, particularly high pressure natural gas streams. It is desirable to recover the impurities, also referred to as the "heavy component(s)", and the methane-rich product, also referred to as the "light component", at as high a pressure as practical for operability in natural gas processing. As previously mentioned, the present invention can be used to obtain methane recovery of greater than about 80 vol. %, more preferably greater than about 85 vol. %, even more preferably greater than about 90 vol. %, and most preferably greater than about 95 vol. %, even when the natural gas is fed at high inlet pressures, such as at inlet pressures greater than about 50 psig, preferably at pressures of about 150 psig, more preferably at inlet pressures greater than about 450 psig, even more preferably at inlet pressures greater than about 600 psig and most preferably at inlet pressures greater than about 1200 psig. The present invention can be used even when the gas stream is at an exceptionally high inlet pressure of up to about 7000 psig. The composition of natural gas streams directly from an underground field (raw natural gas) will vary from field to field. Non-limiting examples of components that comprise a raw natural gas stream include water, condensates (higher molecular weight organics), methane, ethane, propane, butane, $CO_2$, $N_2$, He, $H_2S$, Hg, and mercaptans. Water and condensates are typically removed and the condensates sent to a petroleum refinery. In order to produce a gas that can be introduced into a pipeline for sale to residential and commercial fuel markets contaminants, such as $N_2$, Hg, mercaptans, and the acid gases $CO_2$ and $H_2S$ must to removed to acceptable levels. The levels and impurity types vary from gas field to gas field and in some cases can comprise the majority of molecules in the produced gas. For example, it is not uncommon for some natural gas fields to contain from about 0 to 90 vol. % $CO_2$, more typically from about 10 vol. % to about 70 vol. % $CO_2$.

The present invention also provides a method to increase recovery of the light component by conditioning the temperature and pressure of gas fed to the contactor. This method can be used with or without a contactor having a low volume fraction of mesopores and macropores. During the adsorptive step of well designed kinetically controlled swing adsorption processes, the amount of heavy component in the micropores or free volume can be approximately computed from the adsorption isotherm of the heavy component in equilibrium with its local gas phase concentration in the contactor. In well designed equilibrium controlled swing adsorption processes the amount of heavy component in the micropores or free volume can be approximately computed from the competitive adsorption isotherm of the heavy and light components in equilibrium with their local gas phase concentration in the contactor. These approximations are possible because in well designed swing adsorption processes, the contactor provides good mass transfer characteristics between the gas phase and the adsorbed phase in the micropores or free volume of the contactor. The maximum attainable loading of the heavy component in the macropores or free volume of the contactor is called $q_s$ (units for $q_s$ are milli-mole/m³ of the microporous or polymeric material). At low pressures the adsorption isotherm for the heavy component usually obeys Henry's Law and the amount of heavy component adsorbed, $q_{Heavy}$, in the microporous or polymeric material is $$q_{Heavy} = K_{Heavy} P_{Heavy} q_s \text{(in milli-mole/m}^3\text{)}$$

where $K_{Heavy}$ is the Henry's constant and $P_{Heavy}$ is the partial pressure of the heavy component. The Henry's constant, $K_{Heavy}$ depends on temperature and usually varies according to the equation $$K_{Heavy} = K_0 e^{\frac{\Delta H}{RT}} \text{ (in Pascals}^{-1}\text{)}$$

where $K_0$ is a pre-exponential factor and $\Delta H$ is the heat of adsorption (in joule/mole).

To improve selectivity and recovery for either a kinetically or equilibrium controlled swing adsorption processes the inlet temperature and pressure should be chosen such that at the end of the adsorption step the loading of the heavy component in the micropores or free volume near the point at which feed is introduced to the contactor should be greater than $0.15\ q_s$ and preferably greater than $0.3\ q_s$ and even more preferably greater than $0.6\ q_s$. This requirement places a lower bound on the inlet pressure and a maximum bound on the inlet temperature. With increasing loading of the heavy component in the micropores or free volume of the adsorbent the amount of material that is selectively adsorbed in the contactor is increased and the amount of material that can be selectively released in the desorption step is increased. These increases reduce the loss of the light component that is non-selectively adsorbed into the mesopores and macropores. Increasing the loading significantly beyond this range reduces the recovery of the light component because the slope of the adsorption isotherm tends to decrease with increasing pressure. To maximize the recovery of the light component it is also preferred that near the point at which feed is introduced to the contactor the slope of the adsorption isotherm for the heavy component be large enough so that:

$$\frac{\partial q_{Heavy}}{\partial P_{Heavy}} > \alpha\, K_{Heavy}\, q_s$$

where $\alpha=\frac{1}{50}$, more preferably $\alpha=\frac{1}{25}$, and even more preferably $\alpha=\frac{1}{8}$. This inequality places a maximum bound on the inlet pressure and a minimum bound on the inlet temperature. As such these requirements define a window (i.e., maxima and minima) for feed pressure and temperature in which the recovery of the light component is optimized. Usually it is preferred to operate the swing adsorption process at the lowest pressure within the operating window as is practical. As the feed pressure decreases, the concentration of molecules in the mesopores and macropores of the contactor decreases. Lower concentrations of molecules nonselectively adsorbed in the mesopores and macropores leads to lower losses of the light component in the swing adsorption process.

This window is especially important in natural gas separations because natural gas is usually produced at pressures ranging from 1,500 to 7,000 psi. These feed pressures are usually too high to fall within the optimum recovery window for methane which acts as a light component in swing adsorption separation. It is possible to reduce the feed pressure with a simple expansion nozzle, however this technique wastes energy. It is also possible to access the optimum light component recovery window for separations of most heavy components (such as $CO_2$, $N_2$, $H_2S$, $H_2O$, heavy hydrocarbons, and mercaptans) by preconditioning the natural gas with a turboexpander that recovers the energy from the gas expansion. Energy recovered from gas expansion can then be used for power generation or to help recompress separated acid gas components (such as $CO_2$ or $H_2S$) so that they can be disposed of in underground formations. Underground formations that are suitable for disposal/sequestration of $CO_2$ and $H_2S$ include aquifers that have a top seal that prevents significant loss of injected acid gas components, oil reservoirs, gas reservoirs, depleted oil reservoirs and depleted gas reservoirs. Typically the separated $CO_2$ and $H_2S$ has to be recompressed to pressures greater than 2,000 psi and often to pressures greater than 5,000 psi to be injected into these types of underground formations. Thus, it is important to be able to reuse energy recovered from a turboexpander for recompression. The cost of a turboexpander is also less than a gas fired turbine producing the same amount of power. As such, it is economically advantageous to use a turboexpander to capture energy from gas expansion used to condition natural gas for the optimum methane recovery window. When a turboexpander is used, the energy can either be recovered with a shaft coupled electric generator or with a shaft coupled compressor. It can be advantageous to pass the gas coming out of the turboexpander through a heat exchanger before introducing it into the swing adsorption process in order to access the operating window that maximizes methane recovery. Gas coming out of a turboexpander can be too cold to be in the optimum recovery window because the work is recovered in an isentropic expansion. Typically a heat exchanger will be run so that the gas temperature is increased before entering a swing adsorption process. These considerations are especially important when the swing adsorption is a PSA or RCPSA process.

In applications where $CO_2$ is removed from natural gas in swing adsorption processes it is preferred to formulate the adsorbent with a specific class of 8-ring zeolite materials that has a kinetic selectivity. The kinetic selectivity of this class of 8-ring zeolite materials allows $CO_2$ to be rapidly transmitted into zeolite crystals while hindering the transport of methane so that it is possible to selectively separate $CO_2$ from a mixture of $CO_2$ and methane. For the removal of $CO_2$ from natural gas, this specific class of 8-ring zeolite materials has a Si/Al ratio from about 1:1 to about 1000:1, preferably from about 10:1 to about 500:1, and more from about 50:1 to about 300:1. It should be noted that as used herein, the term Si/Al is defined as the molar ratio of silica to alumina of the zeolitic structure. This preferred class of 8-ring zeolites that are suitable for use herein allow $CO_2$ to access the internal pore structure through 8-ring windows in a manner such that the ratio of single component diffusion coefficients of $CO_2$ and methane (i.e., $D_{CO2}/D_{CH4}$) is greater than 10, preferably greater than about 50, and more preferably greater than about 100 and even more preferably greater than 200. Single component diffusion coefficients are taken to be transport diffusion coefficients measured for a pure gas in the Henry's law regime of the adsorption isotherm. The loading of molecules in the zeolite is low in the Henry's law regime and in this regime the Fickian and Stephan-Maxwell diffusion coefficients are nearly equal. The diffusivity of a porous crystalline material for a particular sorbate is conveniently measured in terms of its diffusion time constant, $D/r^2$, wherein D is the Fickian diffusion coefficient ($m^2$/sec) and the value "r" is the radius of the crystallites (m) characterizing the diffusion distance. In situations where the crystals are not of uniform size and geometry, "r" represents a mean radius representative of their corresponding distributions. One way to measure the time constant and diffusion coefficient is from analysis of standard adsorption kinetics (i.e., gravimetric uptake) using methods described by J. Crank in "The Mathematics of Diffusion", 2nd Ed., Oxford University Press, Great Britain, 1975. Another way to measure the time constant and diffusion coefficient is from analysis of zero length chromatography data using methods described by D. M. Ruthven in "Principles of Adsorption and Adsorption Processes", John Wiley, NY (1984) and by J. Kärger and D. M. Ruthven in "Diffusion in Zeolites and Other Microporous Solids", John Wiley, NY (1992). A preferred way to measure the time constant and diffusion coefficient is with a frequency response technique described by Reyes et al. in "Frequency Modulation Methods for Diffusion and Adsorption Measurements in Porous Solids", J. Phys. Chem. B. 101, pages 614-622, 1997. An example of an 8-ring zeolite in this class of materials that is preferred for use in swing adsorption processes to remove $CO_2$ from natural gas is zeolite DDR. Additional preferred 8-ring zeolites are Sigma-1 and ZSM-58 which are isotypic framework structures of DDR. At temperatures below 100° C. the single component diffusion coefficient of $CO_2$ is found to be more than a hundred times greater than that of methane. From the measured activation energies of the diffusion coefficients, at temperatures up to about 300° C., the diffusion coefficient of $CO_2$ is computed to be more than five fold times greater than that of methane. Resistance to fouling in swing adsorption processes that remove $CO_2$ from natural gas is another advantage offered by this class of 8-ring zeolite materials.

In many instances, nitrogen also has to be removed from natural gas or gas associated with the production of oil. In some cases this is because of the high nitrogen levels (>2 vol %) in the produced gas, and in other cases nitrogen removal is needed in order to liquefy natural gas. It may also be advantageous to separate nitrogen from flash gas that occurs in LNG production so that the methane and hydrocarbon products can be used as fuel. Another application is the purification of gas from LNG boil-off so that the methane and hydrocarbon products can be recovered or used as fuel. When recovered, it may be advantageous to re-liquefy the methane and hydrocarbon and returned them back to the LNG cargo. In all of these applications it is desirable to selectively adsorb the nitrogen to obtain high recovery of a purified methane product from nitrogen containing gas. There have been very few molecular sieve sorbents with significant equilibrium or kinetic selectivity for nitrogen separation from methane. For $N_2$ separation from natural gas it is also preferred to formulate the adsorbent with a class of 8-ring zeolite materials that has a kinetic selectivity. The kinetic selectivity of this class of 8-ring materials allows $N_2$ to be rapidly transmitted into zeolite crystals while hindering the transport of methane so that it is possible to selectively separate $N_2$ from a mixture of $N_2$ and methane. For the removal of $N_2$, from natural gas, this specific class of 8-ring zeolite materials also has a Si/Al ratio from about 1:1 to about 1000:1, preferably from about 10:1 to about 500:1, and more from about 50:1 to about 300:1. This preferred class of 8-ring zeolites that are suitable for use herein allow $N_2$ to access the internal pore structure through 8-ring windows in a manner such that the ratio of single component diffusion coefficients of $N_2$ and methane (i.e., $D_{N2}/D_{CH4}$) is greater than 5, preferably greater than about 20, and more preferably greater than about 50 and even more preferably greater than 100. Resistance to fouling in swing adsorption processes during the remove $N_2$ from natural gas is another advantage offered by this class of 8-ring zeolite materials.

In other instances, it is also desirable to remove $H_2S$ from natural gas which can contain from about 0.001 vol % $H_2S$ to about 70 vol % $H_2S$. In this case, it can be advantageous to formulate the adsorbent with stannosilicates as well as the aforementioned class of 8-ring zeolites that has kinetic selectivity. The kinetic selectivity of this class of 8-ring materials allows $H_2S$ to be rapidly transmitted into zeolite crystals while hindering the transport of methane so that it is possible to selectively separate $H_2S$ from a mixture of $H_2S$ and methane. For the removal of $H_2S$, from natural gas, this specific class of 8-ring zeolite materials has a Si/Al ratio from about 1:1 to about 1000:1, preferably from about 10:1 to about 500:1, and more from about 50:1 to about 300:1. This preferred class of 8-ring zeolites that are suitable for use herein allow $H_2S$ to access the internal pore structure through 8-ring windows in a manner such that the ratio of single component diffusion coefficients of $H_2S$ and methane (i.e., $D_{H2S}/D_{CH4}$) is greater than 5, preferably greater than about 20, and more preferably greater than about 50 and even more preferably greater than 100. DDR framework zeolites, such as Sigma-1 and ZSM-58, are also suitable for the removal of $H_2S$ from natural gas. In some applications the $H_2S$ has to be removed to the ppm or sub-ppm levels. To achieve such extensive removal of $H_2S$ it can be advantageous to use a PPSA or RCPPSA process.

It is sometimes necessary to remove heavy hydrocarbons, as previously defined, from natural gas or gas associated with the production of oil. Heavy hydrocarbon removal may be necessary for dew point conditioning before the natural gas is shipped via pipeline or to condition natural gas before it is liquefied. In other instances it may be advantageous to recover heavy hydrocarbons from produced gas in enhanced oil recovery (EOR) floods that employ $CO_2$ and nitrogen. In still other instances it may be advantageous to recover heavy hydrocarbons from associated gas that is cycled back into an oil reservoir during some types of oil production. In many instances where it is desirable to recover heavy hydrocarbons, the gas can be at pressures in excess of 1,000 psi and in some instances the gas pressure can be in excess of 5,000 psig, even sometimes in excess of about 7,000 psig. It is advantageous in these applications to use an adsorbent formulated with a zeolite having a pore size between about 5 and about 20 angstroms. Non-limiting examples of zeolites having pores in this size range are MFI, faujasite, MCM-41 and Beta. It is preferred that the Si/Al ratio of zeolites utilized in an embodiment of a process of the present invention for heavy hydrocarbon removal be from about 20 to about 1000, preferably from about 200 to about 1000 in order to prevent excessive fouling of the adsorbent.

In some instances, natural gas is produced with mercaptans present and it is advantageous to use adsorption processes to aid in their separation. Streams containing mercaptans and components found in natural gas are present in several processes that have been developed to purify natural gas. It is possible to more selectively separate mercaptans from natural gas or natural gas components and increase the recovery of the valuable components (such as methane) using the contactors of the present invention. It is advantageous in these applications to also use an adsorbent formulated with a zeolite having a pore size between about 5 and about 20 angstroms. Non-limiting examples of zeolites having pores in this size range are MFI, faujasite, MCM-41 and Beta. In these applications the Si/Al ratio of the zeolite can be from about 1 to about 1000.

The low mesoporous and macroporous adsorbent is an integral component of the contactors of the present invention that can be used in both equilibrium and kinetically controlled swing adsorption processes to improve light component product recovery. Adsorbents contactors of the prior art contain significant levels of mesopores and macropores. At the end of the adsorption step, the mesopores and macropores, which are non-selective, will contain significant amounts of light components because transport into the mesopores and macropores is nonselective. This is an especially important problem in high pressure RCPSA, PSA, TSA and PPSA processes because at the end of the adsorption step the number of molecules in the mesopore and macropore spaces can be comparable to the number of molecules selectively adsorbed in the micropores of the adsorbent. In the desorption step most of the light components contained in the mesopores and macropores are undesirably lost to the heavy component product stream. As such, these light molecules are not recovered as desired with the light product. This can result in significant loss of valuable light product. The adsorbent contactors of the present invention can significantly improve this recovery of light products by reducing the volume fraction of the open mesopore and macropore spaces.

In one embodiment of the present invention, the walls of the open flow parallel channels are comprised of the adsorbent. The adsorbent is preferably a microporous adsorbent or polymer that selectively adsorbs the heavy components. Non-limiting examples of microporous adsorbents include zeolites, titanosilicates, ferrosilicates, stannosilicates, aluminophosphates (AlPOs), silicoaluminophosphates (SAPOs) and carbon molecular sieves. In other preferred embodiments, the adsorbent material is comprised of a microporous adsorbent selected from the group consisting of titanosilicates and stannosilicates. In yet other preferred embodiments, the adsorbent material is comprised of a microporous adsorbent selected from the group consisting of aluminophosphates (AlPOs), silicoaluminophosphates (SAPOs) and carbon molecular sieves. Preferred are zeolites for the removal of $CO_2$, $N_2$, and $H_2S$ with the stannosilicates being more preferred for the removal of $H_2S$. In other preferred embodiments, the adsorbent material is comprised of a zeolite selected from the group consisting of MFI, faujasite, MCM-41, and Beta. Non-limiting examples of polymers that can be used as selective adsorbents include polyimides, polysulfones, and functionalized polymers such as amine functionalized polymers.

The adsorbent contactors of the present invention may optionally contain a thermal mass (heat transfer) material to help control heating and cooling of the adsorbent of the contactor during both the adsorption step and desorption step of a pressure swing adsorption process. Heating during adsorption is caused by the heat of adsorption of molecules entering the adsorbent. The optional thermal mass material also helps control cooling of the contactor during the desorption step. The thermal mass can be incorporated into the flow channels of the contactor, incorporated into the adsorbent itself, or incorporated as part of the wall of the flow channels. When it is incorporated into the adsorbent, it can be a solid material distributed throughout the adsorbent layer or it can be included as a layer within the adsorbent. When it is incorporated as part of the wall of the flow channel, the adsorbent is deposited or formed onto the wall. Any suitable material can be used as the thermal mass material in the practice of the present invention. Non-limiting examples of such materials include metals, ceramics, and polymers. Non-limiting examples of preferred metals include steel, copper, and aluminum alloys. Non-limiting examples of preferred ceramics include silica, alumina, and zirconia. An example of a preferred polymer that can be used in the practice of the present invention is polyimide. Depending upon the degree to which the temperature rise is to be limited during the adsorption step, the amount of thermal mass material used can range from about 0 to about 25 times the mass of the microporous adsorbent of the contactor.

A preferred range for the amount of thermal mass in the contactor is from about 0 to 5 times the mass of the microporous adsorbent of the contactor. A more preferred range for the amount of thermal mass material will be from about 0 to 2 times the mass of the microporous adsorbent material, most preferably from about 0 to 1 times the mass of the microporous material of the contactor. In a preferred embodiment, an effective amount of thermal mass is incorporated into the contactor. The effective amount of thermal mass is an amount sufficient to maintain the thermal rise of the adsorbent during the adsorption step to less than about 100° C. In a preferred embodiment, the amount of thermal mass incorporated into the contactor is an amount sufficient to maintain the thermal rise of the adsorbent during the adsorption step to less than about 50° C., and more preferably to less than about 10° C.

Open mesopore and macropore volume includes the volume fraction of all mesopores and macropores that are not filled with a blocking agent, and that are non-selective and thus are capable of being occupied essentially by all components of the gas mixture. Non-limiting examples of blocking agents that can be used in the practice of the present invention include polymers, microporous materials, solid hydrocarbons, and liquids that can fill the open mesopore and macropore space but still allow molecules to transport into the micropores in the selective adsorbent. When the blocking agent is a polymer or liquid, it is preferred that the molecular size of the blocking agent be large enough so that is does not significantly invade micropores of the adsorbent, but not so large that it does not fill the mesopores and macropores. When solid blocking agents are used the particle size of the solid is greater than any selective micropores in the adsorbent but smaller than the mesopores and macropores. As such the blocking agent can fit into the mesopores and macropores without significantly occluding or filling micropores which may be present in the adsorbent.

The blocking agent fills the open mesopores and macropores of the adsorbent to an extent that the volume fraction of the open mesopores and macropores of the adsorbent meets the aforementioned requirements. Non-limiting examples of polymers that can be used as blocking agents include polyimides, polysulfones, and silicone rubbers. Non-limiting examples of liquids that can be used as blocking agents include amines, aromatics such as 1,3,5 trimethylbenzene and branched saturated hydrocarbons such a heptamethylnonane as well as liquid hydrocarbons having carbon numbers in the about 5 to about 60 range. When a liquid blocking agent is used it is advantageous to saturate, or nearly saturate, the feed gas with the liquid blocking agent. Non-limiting examples of solid blocking agents include hydrocarbons such as waxes and those having carbon numbers in the 10-1000 range. Non-limiting examples of microporous materials that can be used in the practice of the present invention include microporous carbons and zeolites having pore sizes larger than those of the selective structured adsorbent of this invention. An example of an adsorbent formulated with a blocking agent is a silica or alumina bound zeolite layer having about 30% mesopore and macropore volume in the interstices between the zeolite particles that is filled in with a liquid so that substantially all voids are filled with liquid (i.e., the total resulting macro and mesoporosity in the layer is less than about 20%). In some cases, the blocking agent forms a continuous network and the adsorbent is a composite structure with the microporous material embedded within the blocking agent. A non-limiting example of such a structure is a zeolite/polymer composite where the polymer is continuous and the composite has less than about 20 volume % in open mesopores or macropores.

It is also possible to formulate the adsorbent using a mesoporous material that fills the macropores to reduce the overall void, or open, volume. An example of such a structure would be an adsorbent having about 30 volume % of macropores that are filled in with a mesoporous sol gel so that the resulting mesopore and macropore volume is less than about 20%.

The channels, also sometimes referred to as "flow channels" or "gas flow channels" are paths in the contactor that allow gas flow through. Generally, flow channels provide for relatively low fluid resistance coupled with relatively high surface area. Flow channel length should be sufficient to provide the mass transfer zone which is at least, a function of the fluid velocity, and the surface area to channel volume ratio. The channels are preferably configured to minimize pressure drop in the channels. In many embodiments, a fluid flow fraction entering a channel at the first end of the contactor does not communicate with any other fluid fraction entering another channel at the first end until the fractions recombine after exiting at the second end. It is important that there be channel uniformity to ensure that substantially all of the channels are being fully utilized, and that the mass transfer zone is substantially equally contained. Both productivity and gas purity will suffer if there is excessive channel inconsistency. If one flow channel is larger than an adjacent flow channel, premature product break through may occur, which leads to a reduction in the purity of the product gas to unacceptable purity levels. Moreover, devices operating at cycle frequencies greater than about 50 cycles per minute (cpm) require greater flow channel uniformity and less pressure drop than those operating at lower cycles per minute. Further, if too much pressure drop occurs across the bed, then higher cycle frequencies, such as on the order of greater than 100 cpm, are not readily achieved.

The dimensions and geometric shapes of the parallel channel contactors of the present invention can be any dimension or geometric shape that is suitable for use in swing adsorption process equipment. Non-limiting examples of geometric shapes include various shaped monoliths having a plurality of substantially parallel channels extending from one end of the monolith to the other; a plurality of tubular members; stacked layers of adsorbent sheets with and without spacers between each sheet; multi-layered spiral rolls, bundles of hollow fibers, as well as bundles of substantially parallel solid fibers. The adsorbent can be coated onto these geometric shapes or the shapes can, in many instances, be formed directly from the adsorbent material plus suitable binder. An example of a geometric shape formed directly from the adsorbent/binder would be the extrusion of a zeolite/polymer composite into a monolith. Another example of a geometric shape formed directly from the adsorbent would be extruded or spun hollow fibers made from a zeolite/polymer composite. An example of a geometric shape that is coated with the adsorbent would be a thin flat steel sheet that is coated with a microporous, low mesopore, adsorbent film, such as a zeolite film. The directly formed or coated adsorbent layer can be itself structured into multiple layers or the same or different adsorbent materials. Multi-layered adsorbent sheet structures are taught in United States Patent Application Publication No. 2006/0169142, which is incorporated herein by reference.

The dimensions of the flow channels can be computed from considerations of pressure drop along the flow channel. It is preferred that the flow channels have a channel gap from about 5 to about 1,000 microns, preferably from about 50 to about 250 microns. As utilized herein, the "channel gap" of a flow channel is defined as the length of a line across the minimum dimension of the flow channel as viewed orthogonal to the flow path. For instance, if the flow channel is circular in cross-section, then the channel gap is the internal diameter of the circle. However, if the channel gap is rectangular in cross-section, the flow gap is the distance of a line perpendicular to and connecting the two longest sides of the rectangular (i.e., the length of the smallest side of the rectangle). It should also be noted that the flow channels can be of any cross-sectional configuration. Preferred embodiments are wherein the flow channel cross-sectional configuration is either circular, rectangular or square. However, any geometric cross-sectional configuration may be used, such as but not limited to, ellipses, ovals, triangles, or various polygonal shapes. In other preferred embodiments, the ratio of the adsorbent volume to flow channel volume in the adsorbent contactor is from about 0.5:1 to about 100:1, and more preferably from about 1:1 to about 50:1.

In some RCPSA applications, the flow channels are formed when adsorbent sheets are laminated together. Typically, adsorbent laminates for RCPSA applications have flow channel lengths from about 0.5 centimeter to about 10 meter, more typically flow channel lengths from about 10 cm to about 1 meter and a channel gap of about 50 to about 250 microns. The channels may contain a spacer or mesh that acts as a spacer. For laminated adsorbents, spacers can be used which are structures or material, that define a separation between adsorbent laminates. Non-limiting examples of the type of spacers that can be used in the present invention are those comprised of dimensionally accurate: plastic, metal, glass, or carbon mesh; plastic film or metal foil; plastic, metal, glass, ceramic, or carbon fibers and threads; ceramic pillars; plastic, glass, ceramic, or metal spheres, or disks; or combinations thereof. Adsorbent laminates have been used in devices operating at PSA cycle frequencies up to at least about 150 cpm. The flow channel length may be correlated with cycle speed. At lower cycle speeds, such as from about 20 to about 40 cpm, the flow channel length can be as long as or longer than one meter, even up to about 10 meters. For cycle speeds greater than 40 cpm, the flow channel length typically is decreased, and may vary from about 10 cm to about 1 meter. Longer flow channel lengths can be used for slower cycle PSA processes. Rapid cycle TSA processes tend to be slower than rapid cycle PSA processes and as such longer flow channel lengths can also be used with TSA processes.

The overall adsorption rate of the swing adsorption processes is characterized by the mass transfer rate from the flow channel into the adsorbent. It is desirable to have the mass transfer rate of the species being removed (i.e., the heavy component) high enough so that most of the volume of the adsorbent is utilized in the process. Since the adsorbent selectively removes the heavy component from the gas stream, inefficient use of the adsorbent layer can lower recovery of the light component and/or decrease the purity of the light product stream. With use of the present invention, it is possible to formulate an adsorbent with a low volume fraction of mesoporous and macroporous such that most of the volume of the adsorbent, which will be in the microporous range, is efficiently used in the adsorption and desorption of the heavy component. One way of doing this is to have an adsorbent of substantially uniform thickness where the thickness of the adsorbent layer is set by the mass transfer coefficients of the heavy component and the time of the adsorption and desorption steps of the process. The thickness uniformity can be assessed from measurements of the thickness of the adsorbent or from the way in which it is fabricated. It is preferred that the uniformity of the adsorbent be such that the standard deviation of its thickness is less than about 25% of the average thickness. More preferably, the standard deviation of the thickness of the adsorbent is less than about 15% of the average thickness. It is even more preferred that the standard deviation of the adsorbent thickness be less than about 5% of the average thickness.

Calculation of these mass transfer rate constants is well known to those having ordinary skill in the art and may also be derived by those having ordinary skill in the art from standard testing data. D. M. Ruthven & C. Thaeron, Performance of a Parallel Passage Absorbent Contactor, Separation and Purification Technology 12 (1997) 43-60, which is incorporated herein by reference, clarifies many aspects of how the mass transfer is affected by the thickness of the adsorbent, channel gap and the cycle time of the process. Also, U.S. Pat. No. 6,607,584 to Moreau et al., which is also incorporated by reference, describes the details for calculating these transfer rates and associated coefficients for a given adsorbent and the test standard compositions used for conventional PSA.

A figure of merit for the mass transfer through the adsorbent layer is a time constant, $\tau_a$, for transport of the heavy component computed at each point in the adsorbent. For a planar adsorbent sheet with thickness in the x direction, and the y and z directions being in the plane of the sheet, the time constant $\tau_a$ of the heavy component is $$\tau_a[x,y,z] = \text{Minimum}[L_{path}^2/D_{path}] \text{(in seconds)}$$

where $D_{path}$ is the average transport diffusion coefficient of the heavy component along a path from the feed channel to the point (x,y,z) and $L_{path}$ is the distance along the path. There are many possible trajectories or paths from the feed channel to each point (x,y,z) in the adsorbent. The time constant is the minimum of the possible time constants ($L_{path}^2/D_{path}$) along all possible paths from the feed channel to the (x,y,z) point in the adsorbent. This includes paths through mesopores and macropores. If there is a solid material in the adsorbent (such as that which may be included for heat management) there will be no transport within it and (x,y,z) points within it are not included in the computation. The transport diffusion coefficient of each species is taken to be the single component Stefan-Maxwell diffusion coefficient for each species. The average transport diffusion coefficient along the path, $D_{path}$, is the linearly averaged diffusion coefficient along the path. A linear averaging is sufficient to provide a diffusion coefficient characterizing the path. When the heavy component has many species the diffusion coefficient, $D_{path}$, is also compositionally averaged. The diffusion coefficient depends on temperature and it may depend on pressure as well. To the extent that the diffusion coefficient changes, it must be averaged for the temperature and pressure changes occurring during a cycle. For an adsorbent to be efficient, the averaged thickness of the adsorbent layer preferably is chosen such that the time constant for at least half the points (or volume) in the adsorbent that is not a dense solid is less than the cycle time of the process. More preferably, the average thickness of the adsorbent layer is chosen such that the time constant for at least 75% of the points (or volume) in the adsorbent that is not a dense solid is less than the cycle time of the process. Even more preferably the average thickness of the adsorbent layer is chosen such that the time constant for at least 75% of the points (or volume) in the adsorbent that is not a dense solid is less than about 25% of the cycle time of the process.

The present invention can be applied to improve the separation of molecular species from synthesis gas. Synthesis gas can be produced by a wide variety of methods, including steam reforming of hydrocarbons, thermal and catalytic partial oxidation of hydrocarbons, and many other processes and combinations known in the art. Synthesis gas is used in a large number of fuel and chemical applications, as well as power applications such as Integrated Gasification Combined Cycle (IGCC). All of these applications have a specification of the exact composition of the syngas required for the process. As produced, synthesis gas contains at least CO and $H_2$. Other molecular components in the gas can be $CH_4$, $CO_2$, $H_2S$, $H_2O$, and $N_2$. Minority (or trace) components in the gas can include hydrocarbons, $NH_3$ and NOx. In almost all applications most of the $H_2S$ has to be removed from the syngas before it can be used and in many applications it is desirable to remove much of the $CO_2$. In applications where the syngas is used as a feedstock for a chemical synthesis process, it is generally desirable to adjust the $H_2$/CO ratio to a value that is optimum for the process. In certain fuel applications, a water-gas shift reaction may be employed to shift the syngas almost entirely to $H_2$ and $CO_2$, and in many such applications it is desirable to remove the $CO_2$.

The present invention provides a method for increasing the recovery of the valuable molecular components from synthesis gas. In most applications valuable components are CO and $H_2$. When multiple species are removed from the synthesis gas, individual contactors, each optimized for the removal of a particular component, can be used. Multiple contactors can be used because the invention provides a means of rapidly changing the pressure in the contactor allowing for rapid cycle operation and consequentially small equipment size. Alternatively several different adsorbents can be incorporated into a single contactor. This provides a means of selectively removing several species with a single contactor.

It can be desirable to recover separated acid gases, such as $H_2S$ and/or $CO_2$, at higher pressure. The recovery of higher pressure acid gases can be desirable, for example, when $CO_2$ sequestration is planned. In these cases, adsorption by temperature swing (TSA) can be preferred over pressure swing. The invention provides a means to rapidly change the contactor temperature without experiencing large heat losses, long heat-up and cool-down times, or adsorbate dilution. Temperature swing adsorption can be executed with fixed parallel-channel contactors and associated valves, or by means of a rotary-based parallel-channel contactor following the approach of a Ljungstrom heat exchanger.

Rapid TSA cycle operation is facilitated with a parallel channel contactor where the adsorbent is on one surface of a compact heat exchange structure. Heating and cooling would take place in a channel isolated from the adsorbing and desorbing material. In this configuration, a thermal wave can be made to move through the contactor during the adsorption step allowing for better separation of adsorbed components. In some instance a chromatographic like separation can be achieved (with no dilution from a carrier gas). This type of parallel channel contactor arrangement can be extremely energy efficient. Thermal energy used in the swing adsorption process can be readily recovered and reused. Because of the energy efficiency a larger degree of thermal swing can be used.

The contactors of the present invention can better be understood with reference to the Figures hereof. FIG. 1 hereof is a representation of a parallel channel contactor of the present invention in the form of a monolith formed directly from a microporous adsorbent plus binder and containing a plurality of parallel flow channels. A wide variety of monolith shapes can be formed directly by extrusion processes. An example of a cylindrical monolith 1 is shown schematically in FIG. 1 hereof. The cylindrical monolith 1 contains a plurality of parallel flow channels 3. These flow channels 3 can have channel gaps from about 5 to about 1,000 microns, preferably from about 50 to about 250 microns, as long as all channels of a given contactor have substantially the same size channel gap. The channels can be formed having a variety of shapes including, but not limited to, round, square, triangular, and hexagonal. The space between the channels is occupied by the adsorbent 5. As shown the channels 3 occupy about 25% of the volume of the monolith and the adsorbent 5 occupies about 75% of the volume of the monolith. The adsorbent 5 can occupy from about 50% to about 98% of the volume of the monolith. The effective thickness of the adsorbent can be defined from the volume fractions occupied by the adsorbent 5 and channel structure as:

$$\text{Effective Thickness Of Adsorbent} = \frac{1}{2} \text{Channel Diameter} \frac{\text{Volume Fraction Of Adsorbent}}{\text{Volume Fraction Of Channels}}$$

Figure 2:
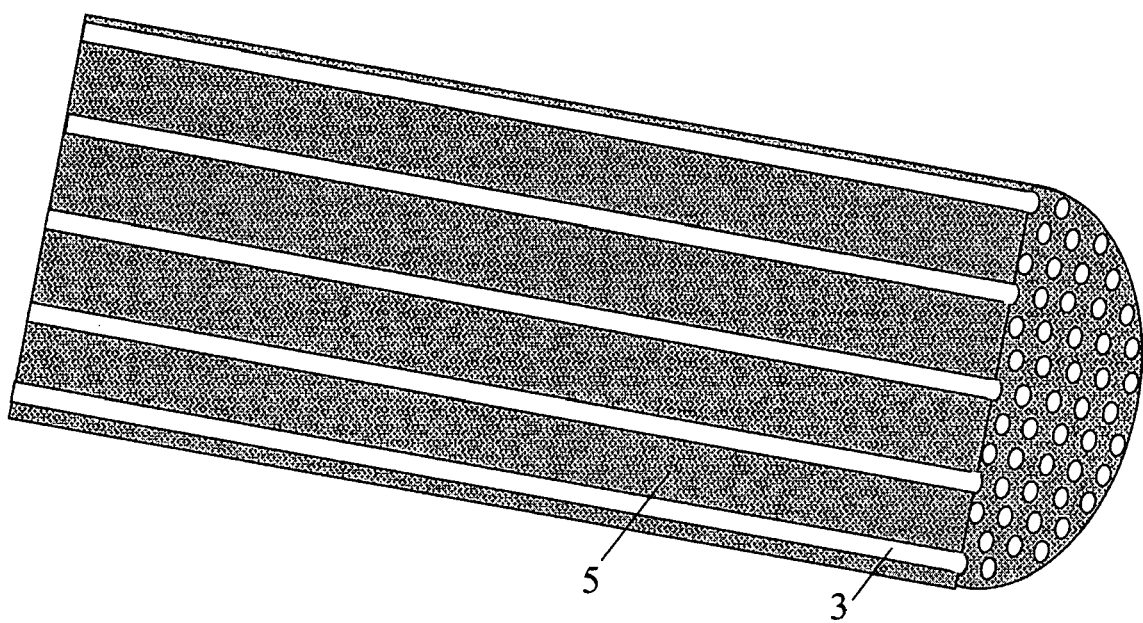
FIG. 2 hereof is a cross-sectional representation along the longitudinal axis of the monolith of FIG. 1.
Figure 3:
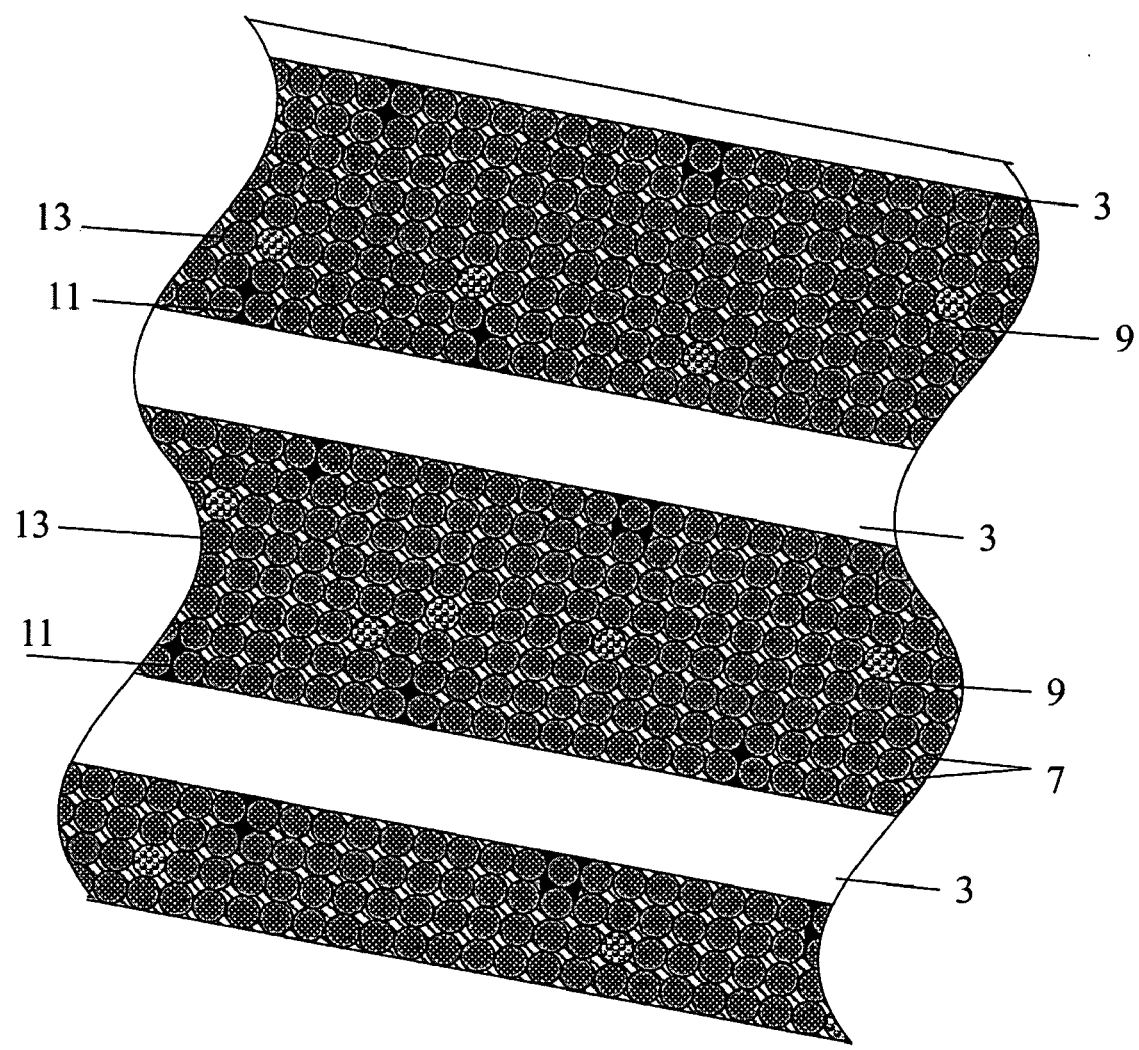
FIG. 3 hereof is a representation of a magnified section of the cross-sectional view of the monolith of FIG. 2 showing the detailed structure of the adsorbent layer along with a blocking agent occupying some of the mesopores and macropores.

For the monolith of FIG. 1 hereof the effective thickness of the adsorbent will be about 1.5 times the diameter of the feed channel. When the channel diameter is in a range from about 50 to about 250 microns it is preferred that the thickness of the adsorbent layer, in the case wherein the entire contactor is not comprised of the adsorbent, be in a range from about 25 to about 2,500 microns. For a 50 micron diameter channel, the preferred range of thickness for the adsorbent layer is from about 25 to about 300 microns, more preferred range from about 50 to about 250 microns. FIG. 2 is a cross-sectional view along the longitudinal axis showing feed channels 3 extending through the length of the monolith with the walls of the flow channels formed entirely from adsorbent 5 plus binder. A schematic diagram enlarging a small cross section of the feed channels 3 and adsorbent layer 5 of FIG. 2 is shown in FIG. 3 hereof. The adsorbent layer is comprised of a microporous adsorbent, or polymeric, particles 7; solid particles (thermal mass) 9; that act as heat sinks, a blocking agent 13 and open mesopores and micropores 11. As shown, the microporous adsorbent or polymeric particles 7 occupy about 60% of the volume of the adsorbent layer and the particles of thermal mass 9 occupy about 5% of the volume. With this composition, the voidage (flow channels) is about 55% of the volume occupied by the microporous adsorbent or polymeric particles. The volume of the microporous adsorbent 5 or polymeric particles 7 can range from about 25% of the volume of the adsorbent layer to about 98% of the volume of the adsorbent layer. In practice, the volume fraction of solid particles 9 used to control heat will range from about 0% to about 75%, preferably about 5% to about 75%, and more preferably from about 10% to about 60% of the volume of the adsorbent layer. A blocking agent 13 fills the desired amount of space or voids left between particles so that the volume fraction of open mesopores and macropores 11 in the adsorbent layer 5 is less than about 20%.

When the monolith is used in a gas separation process that relies on a kinetic separation (predominantly diffusion controlled) it is advantageous for the microporous adsorbent or polymeric particles 7 to be substantially the same size. It is preferred that the standard deviation of the volume of the individual microporous adsorbent or polymeric particles 7 be less than 100% of the average particle volume for kinetically controlled processes. In a more preferred embodiment the standard deviation of the volume of the individual microporous adsorbent or polymeric particles 7 is less than 50% of the average particle volume. The particle size distribution for zeolite adsorbents can be controlled by the method used to synthesize the particles. It is also possible to separate pre-synthesized microporous adsorbent particles by size using methods such as a gravitational settling column. It may also be advantageous to use uniformly sized microporous adsorbent or polymeric particles in equilibrium controlled separations.

There are several ways that monoliths can be formed directly from a structured microporous adsorbent. For example, when the microporous adsorbent is a zeolite, the monolith can be prepared by extruding an aqueous mixture containing effective amounts of a solid binder, zeolite and adsorbent, solid heat control particles, and polymer. The solid binder can be colloidal sized silica or alumina that is used to bind the zeolite and solid heat control particles together. The effective amount of solid binder will typically range from about 0.5 to about 50% of the volume of the zeolite and solid heat control particles used in the mixture. If desired, silica binder materials can be converted in a post processing step to zeolites using hydrothermal synthesis techniques and, as such, they are not always present in a finished monolith. A polymer is optionally added to the mixture for rheology control and to give green extrudate strength. The extruded monolith is cured by firing it in a kiln where the water evaporates and the polymer burns away, thereby resulting in a monolith of desired composition. After curing the monolith, the adsorbent layer 5 will have about 20 to about 40 vol. % mesopores and macropores. A predetermined amount of these pores can be filled with a blocking agent 13, as previously discussed, in a subsequent step such as by vacuum impregnation.

Another method by which a monolith can be formed directly from a microporous adsorbent is by extruding a polymer and microporous adsorbent mixture. Preferred microporous adsorbents for use in extrusion process are carbon molecular sieves and zeolites. Non-limiting examples of polymers suitable for the extrusion process include epoxies, thermoplastics, and curable polymers such as silicone rubbers that can be extruded without an added solvent. When these polymers are used in the extrusion process, the resulting product will preferably have a low volume fraction of mesopores and macropores in the adsorbent layer.

Figure 4:
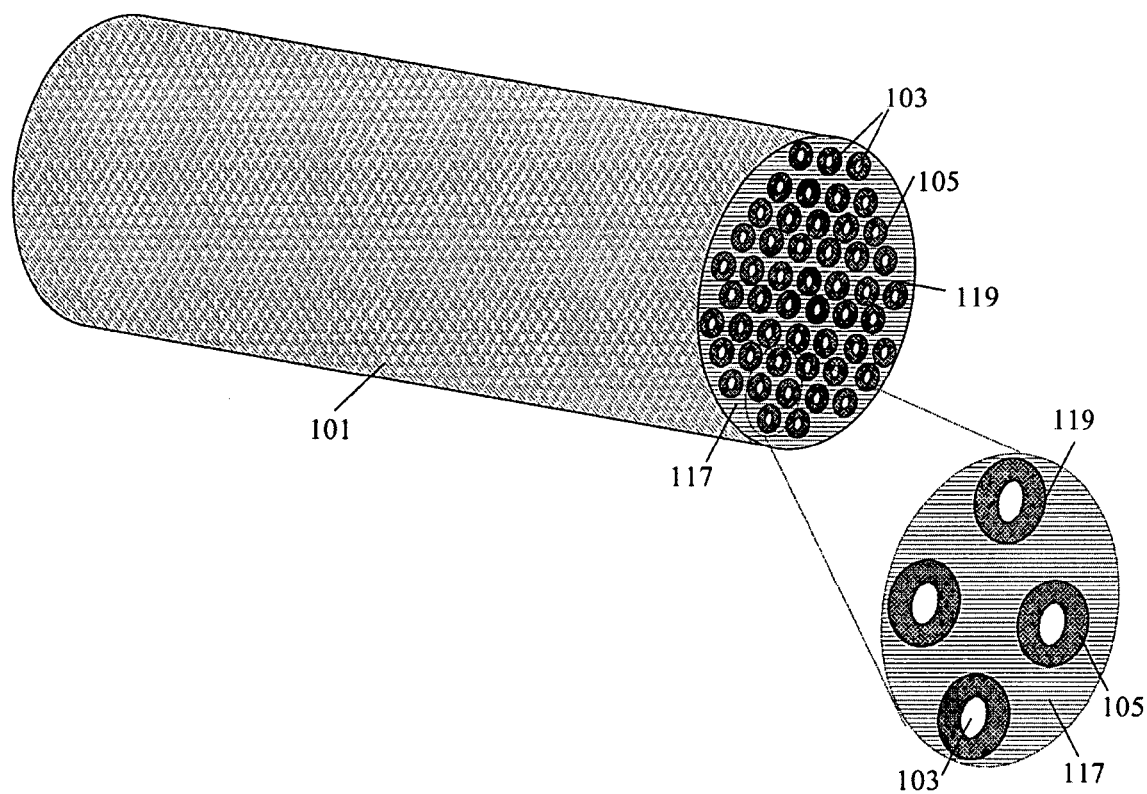
FIG. 4 hereof is another representation of an embodiment of a parallel channel contactor of the present invention in the form of a coated monolith where the adsorbent layer is coated onto the channel wall.

FIG. 4 hereof is a representation of a parallel channel contactor 101 of the present invention in the form of a coated monolith where an adsorbent layer is coated onto the walls of the flow channels of a preformed monolith. For the parallel channel contactors of this Figure, an extrusion process is used to form a monolith from a suitable non-adsorbent solid material, preferably a metal such as steel, a ceramic such as cordierite, or a carbon material. By the term "non-adsorbent solid material" we mean a solid material that is not to be used as the selective adsorbent for the parallel channel contactor. An effective amount and thickness of a ceramic or metallic glaze, or sol gel coating, 119 is preferably applied to effectively seal the channel walls of the monolith. Such glazes can be applied by slurry coating the channel walls, by any suitable conventional means, followed by firing the monolith in a kiln.

Another approach is to apply a sol gel to the channel walls followed by firing under conditions that densify the coating. It is also possible to use vacuum and pressure impregnation techniques to apply the glaze or sol gel to the channel walls. In such a case, the glaze or sol gel will penetrate into the pore structure of the monolith 117. In all cases, the glaze seals the wall of the channel such that gas flowing thorough the channel is not readily transmitted into the body of the monolith. An adsorbent layer 105 is then uniformly applied onto the sealed walls of the channels. The adsorbent layer 105 reduces the opening, or bore, of the channels, thus the flow channel 103 used in swing adsorption processes is the open channel left inside of the coating. These flow channels 103 can have channel gaps as previously defined. The adsorbent layer 105 can be applied as a coating, or layer, on the walls of the flow channels by any suitable method. Non-limiting examples of such methods include fluid phase coating techniques, such as slurry coating, slip coating, hydrothermal film formation, hydrothermal coating conversion, and hydrothermal growth. When non-hydrothermal coating techniques are used, the coating solutions should include at least the microporous adsorbent or polymeric particles, a viscosifying agent such as polyvinyl alcohol, heat transfer (thermal mass) solids, and optionally a binder. The heat transfer solid may not be needed because the body of the monolith 101 can act to as its own heat transfer solid by storing and releasing heat in the different steps of the separation process cycle. In such a case, the heat diffuses through the adsorbent layer 105 and into the body of the monolith 101. If a viscosifying agent, such as polyvinyl alcohol, is used it is usually burns away when the coating is cured in a kiln. It can be advantageous to employ a binder such as colloidal silica or alumina to increase the mechanical strength of the fired coating. Mesopores or macropores will typically occupy from about 20 to about 40% of the volume of the cured coating. An effective amount of blocking agent is applied to complete the adsorbent layer for use. By effective amount of blocking agent we mean that amount needed to occupy enough of the mesopores and macropores such that the resulting coating contains less than about 20% of its pore volume in open mesopores and macropores.

Figure 5:
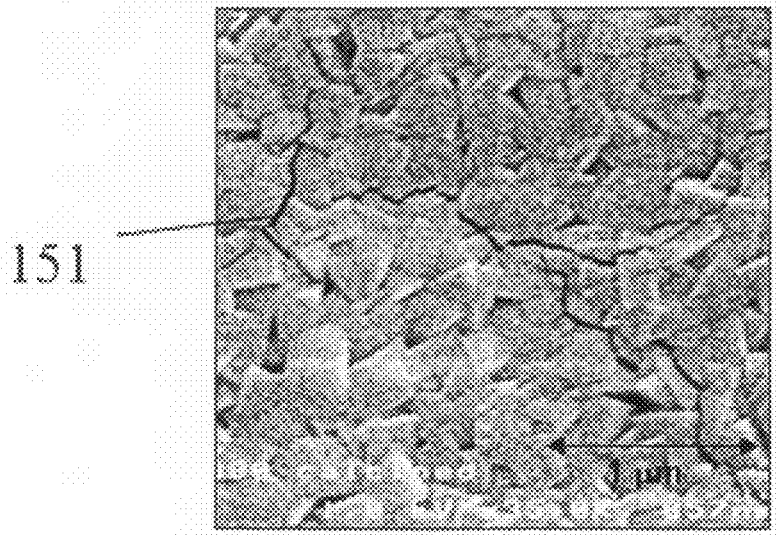
FIG. 5 hereof is an electron micrograph of the surface of a DDR film that is suitable to act as the adsorbent layer of the contactors of the present invention with a volume fraction of open mesopores and micropores that is less than about 7%.
Figure 6:
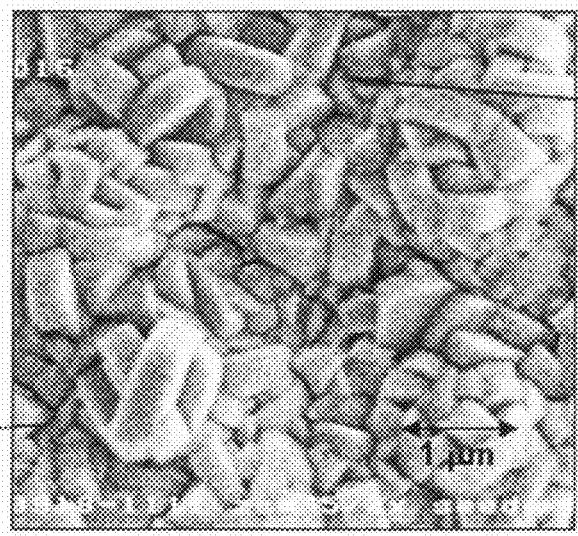
FIG. 6 is an electron micrograph of the surface of an MFI film that is also suitable to act as an adsorbent layer of the contactors of the present invention with a volume fraction of open mesopores and micropores that is less than about 7%.

If a hydrothermal film formation method is employed, the coating techniques used can be very similar to the way in which zeolite membranes are prepared. An example of a method for growing a zeolite layer is taught in U.S. Pat. No. 7,049,259, which is incorporated herein by reference. Zeolite layers grown by hydrothermal synthesis on supports often have cracks and grain boundaries that are mesopore and macropore in size. The volume of these pores is often less than about 10 volume % of the film thickness and there is often a characteristic distance, or gap, between cracks. Thus, as-grown films can often be used directly as an adsorbent layer without the need for a blocking agent. Examples of crack and grain boundaries in as-grown zeolite films are shown in high resolution scanning electron micrographs FIGS. 5 and 6 hereof. The zeolite film of FIG. 5 is comprised of Sigma-1 zeolite which has a framework structure that is isotypic with DDR. The film is about 25 micrometers thick with cracks 151 that are about 100 to about 300 angstrom wide, which cracks are readily visible on the surface of the film. The zeolite film in FIG. 6 is an MFI film that was produced by coating a first coating layer approximately 0.5 micrometers thick using colloidal ZSM-5 seeds onto a support and then placing the seed covered support in a hydrothermal synthesis solution. The colloidal ZSM-5 seeds nucleated the growth of a MFI film about 15 micrometers thick in the hydrothermal synthesis step. The Si/Al ratio of the deposited film was greater than about 100. Cracks of several hundred angstrom size 153 and gaps 155 between the MFI zeolite crystals are apparent in the micrograph. Besides the cracks and gaps there are grain boundaries between crystals. These grain boundaries can connect to the crack structure and aid in transport of molecules to the zeolite crystals that are deeper in the film. Many of the grain boundaries have dimensions in the micropore range and some have dimensions in the mesopore range. It is apparent from the micrographs of FIGS. 5 and 6 that the open mesopores and macropores occupy a very small amount of the overall volume at the surface of the film. Cross sectional images of these films confirmed that the open mesopores and macropores in fact do occupy less than about 7% of the volume of the films.

Figure 7:
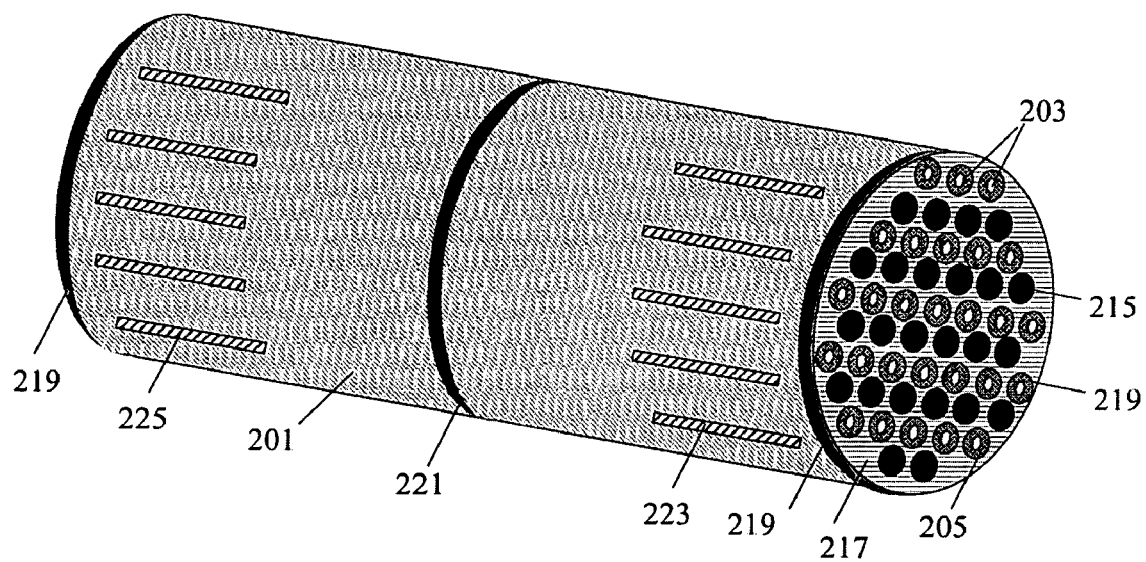
FIG. 7 hereof represents another embodiment of the present invention in which the parallel channel contactor is in the form of a coated monolith for TSA applications where the adsorbent layer is coated onto the channel walls of a pre-formed monolith.

FIG. 7 hereof is a representation of a parallel channel contactor of the present invention in the form of a coated monolith 201 for TSA applications where the adsorbent layer is coated onto the channel of a preformed monolith comprised of non-adsorbent material. When TSA or RCTSA processes are performed the contactor will preferably have paths, or separate channels, that can be used to heat and cool the adsorbent. For TSA or RCTSA processes, the parallel channel contactor can be configured in a configuration similar to a shell and tube heat exchanger with the adsorbent coated on the tube walls of the heat exchanger. In this Figure, an extrusion process is used to form a monolith from a suitable non-adsorbent material including a metal such as steel, or a ceramic such as cordierite, or a carbon. A ceramic or metallic glaze or sol gel coating 219 is applied to seal the channel walls of the monolith. As previously mentioned, such glazes can be applied by slurry coating the channel walls followed by curing by firing. A sol gel can also be applied to the channel walls and then fired under conditions that densify the coating. As previously mentioned, it is also possible to use vacuum and pressure impregnation techniques to apply the glaze or sol gel. In this case the glaze or sol gel will penetrate into the pore structure of the monolith 217. In all cases the glaze seals the wall of the channel such that gas flowing thorough the channel is not readily transmitted into the body of the monolith. It may also be desirable to impregnate the pore structure of the monolith 217 with a solid material before the channel walls are sealed. Alternate rows of channels are sealed at their ends 215 in order to provide for TSA operation. At the opposite end of the monolith these same rows of channels are also sealed. Slots (223 and 225) are cut through the monolith at both ends to provide flow access to the sealed rows of channels 215. Sealing surfaces 219 are provided at both ends of the monolith as well as in the middle of the monolith 221. In operation, the monolith will be mounted in a module in a manner that seals the ends of the channels as well as the middle of the monolith. Any suitable technology can be used to seal the ends of the channels including metallic welds, gasketing with materials such as rubbers or carbons, and the use of adhesives such as inorganic cements and epoxies. The module is configured so that a heating or cooling fluid can be flowed through the channels sealed at the ends 215 by introducing it through the slots 223 and removing it through slots 225. The heating and cooling fluid will undergo heat exchange with fluid flowing through the channels that are open at the end of the module. These modifications to the monolith convert it into a heat exchanger. It will be understood that there are various other ways in which heat exchangers can be produced or configured. Non-limiting examples of such other ways include shell and tube heat exchangers, fiber film heat exchangers and printed circuit heat exchangers, all of which are well known in the art. By coating an adsorbent layer with a low volume fraction of mesopores and macropores on one side of a heat exchanger it can be used in accordance with the present invention. As such, this example illustrates how heat exchangers can be converted into modules suitable for TSA with an adsorbent layer having a low volume fraction of mesopores and macropores.

Feed channels 203 can have channel gaps from about 5 to about 1,000 microns, preferably from about 50 to about 250 microns. When the channel gap 203 is in a range from 50 to about 250 microns it is preferred that the thickness of the adsorbent layer 205 be in a range form about 25 to about 2,500 microns. For a 50 micron diameter feed channel 203 the preferred range of thickness for the adsorbent layer is from 25 to 300 microns and a more preferred range is from 50 to 250 microns. The techniques previously discussed above can be used to coat the adsorbent layer into the monolith.

Figure 8:
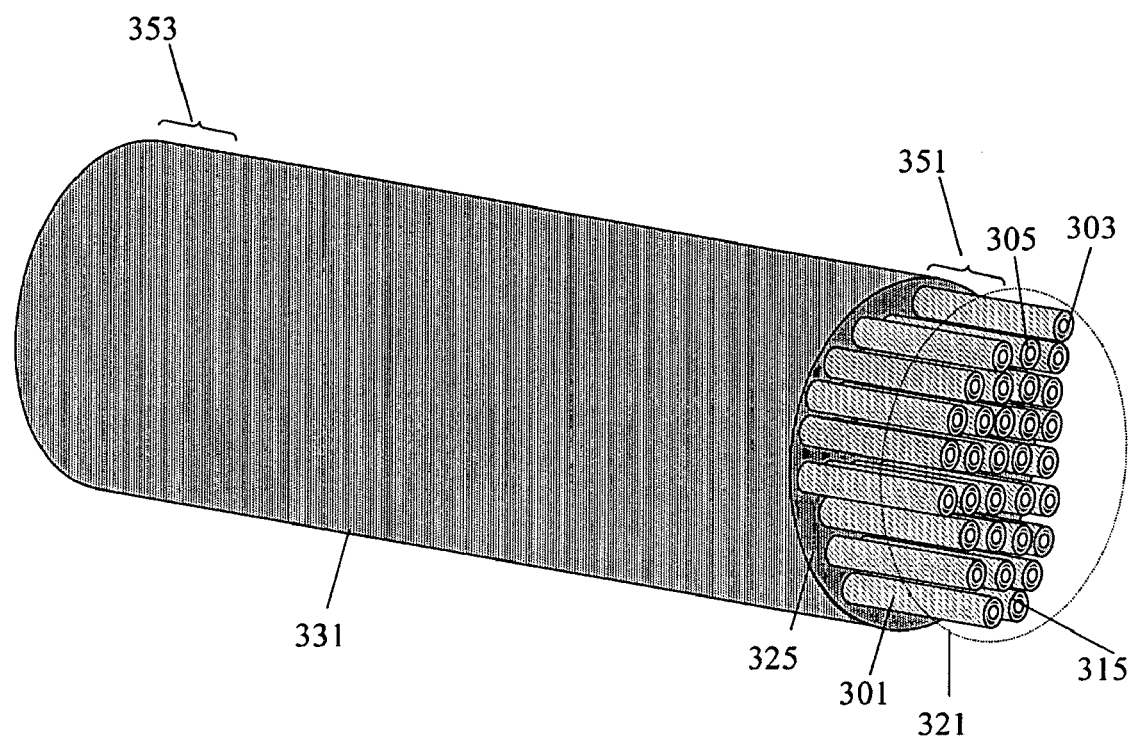
FIG. 8 hereof is a representation of a parallel channel contactor of the present invention in the form of an array of hollow fibers.

FIG. 8 hereof is a schematic of a parallel channel contactor of the present invention in the form of a substantially parallel array of hollow fibers embedded in a matrix material 331. A wide variety of hollow fibers can be formed directly using conventional spinning and extrusion processes. The contactor of FIG. 8 is formed from an array of hollow fibers 301. The bores 303 of the fibers are used as flow channels. These flow channels 303 can also have a channel gap from about 5 to about 1,000 microns, preferably from about 50 to about 250 microns as previously mentioned. Also as previously mentioned, the walls of the fibers contain an adsorbent layer 305. When the channel gap 303 is in a range from 50 to about 250 microns it is preferred that the thickness of the adsorbent layer 305 be in a range from about 25 to 2,500 microns.

Various different methods known in the art can be used to produce the adsorbent layer 305 in the fiber. For example, the hollow polymer fibers with low mesoporosity can be extruded. Some spinning techniques can also be used to produce hollow fibers with mesopores and macropores that can be removed in post treatments such as thermal annealing, polymer coating, epoxy coating or filling with a blocking agent. Hollow fibers that are composites of polymers and adsorbents can be formed in both spinning and extrusion processes. These processes often form the fiber from a dope containing the polymer, adsorbent particles, and often a solvent. In some cases, the surface of the adsorbent particle is functionalized to promote adhesion between the polymer matrix and the adsorbent particle. When the volume fraction of mesopores and macropores is too high, it can be lowered by a post treatment using thermal annealing, or by filling an effective amount of mesopores and macropores with a blocking agent.

It is also possible to produce hollow fibers of zeolites by extrusion. In these processes the zeolite is mixed with a polymer or an oligomeric viscosifying agent, such as a lower molecular weight polyvinyl alcohol. Optionally, a solvent such as water, alcohol, or liquid hydrocarbon can be added to the dope. It is also optional to use a binder material, such as colloidal silica or colloidal alumina that can be added to this dope. Solid particles, such as alumina or aluminum can also be added to the dope. The dope is then extruded and from the green state the final ceramic body is produced. This fiber, in the green state, can then be placed into a kiln and fired to form the final fiber comprised of zeolite, and optionally binder and solid particles. Alternatively, the fiber in the green state can be placed in a hydrothermal synthesis reactor to produce a final fiber comprised of zeolite, and optionally binder and solid thermal mass particles. Another method to produce a zeolite fiber is by hydrothermally growing a zeolite coating on a solid polymer fiber that burns away during the calcinations step. In all cases, mesoporosity and microporosity in the fiber can be reduced to within a target range by filling with a blocking agent in a subsequent step.

The fibers can be formed into a substantially parallel array to form a contactor of the present invention. One method to do this is with an embedding or potting process that surrounds the entire length of the fibers with a matrix material 325. To visualize the array in FIG. 8 the end of the matrix material 351 has been rendered transparent along with the face 321 of the embedded hollow fiber bundle. In many instances, it can be advantageous to coat the exterior of the fiber with a material that acts as a diffusion barrier 315. Non-limiting examples of materials that can act as diffusion barriers include sputter deposited metal and ceramic films, evaporated metal and ceramic films, metal and ceramic films formed by chemical vapor deposition, coated composites of polymers and solids (such as clays) and coatings of polymers that have low diffusion coefficients. To act as a diffusion barrier, the effective diffusion coefficient of the coating should be less than about $\frac{1}{10}$ the average diffusion coefficient in the adsorbent layer and preferably less than about $\frac{1}{1000}$ the average diffusion coefficient in the adsorbent layer. When a diffusion barrier is used, the gas in the feed channel is effectively contained in the feed channel and adsorbent layer. This can eliminate the need for a supporting matrix around the fibers, thus lowering the mass of the contactor, and in some cases allowing for the cycle time in the process to be decreased (i.e., rapid cycle operation).

Another fabrication method suitable for use herein is to coat the adsorbent inside the prefabricated fiber such as a hollow glass fiber, hollow silica fiber or hollow polymer fiber. Coating methods previously described can be used to form an adsorbent layer inside of a prefabricated fiber. When the prefabricated fiber is made from glass, or silica, the final product has a built in diffusion barrier 315.

When there is no diffusion barrier on the fiber it is advantageous for the matrix material to contain an adsorbent having a low volume fraction of mesopores and macropores. In this case, it is advantageous to space the fibers closely together with the distance between adjacent fibers less than about 5 fiber diameters, preferably less than about 1.5 fiber diameters. When there is a diffusion barrier on the outer surface of the fibers, it can be advantageous to embed only the ends 351 and 353 of the fiber bundle in the matrix material. In this case, the matrix material only has to support the fibers and not have substantial gas flow through the material. It can be composed of polymer, metal or ceramic or combinations thereof. It is preferred that the matrix be nonporous and requirements for having an adsorbent in the matrix material can be relaxed or eliminated. Requirements for spacing between fibers can be less critical than when the entire length of the fiber is potted or embedded. The matrix material can be applied selectively to the ends of the fiber bundles by any suitable method known in the art. Non-limiting examples of such methods include potting, embedding, casting, electroplating, or electroless plating processes. To avoid plugging the end of the fibers the end of the fibers can be filled with a material that can be readily removed after the matrix is applied. Non-limiting examples of materials that can be readily removed include polymers, metals, salts and inorganics that can be selectively dissolved or etched away after the matrix material has been applied. Grinding, machining and polishing methods can also be used to open the ends of the fibers. Other methods to pot or embed the ends of the fibers are similar to those used to form hollow fiber membrane modules. When the ends of the fiber bundle are potted with a matrix material it is advantageous to place the contactor into an operational PSA, RCPSA, RCPPSA or PPSA module in a manner such that most of the feed gas flows through the bore of the fiber. One way to ensure that the flow goes through the bore of the fiber is to place a fibrous packing, or inram, between the matrix material at the ends 351 and 353 and the interior of the PSA, RCPSA, RCPPSA or PPSA module. Another way is to bond the ends of the contactor to the interior of the pressure swing adsorption module.

Figure 9:
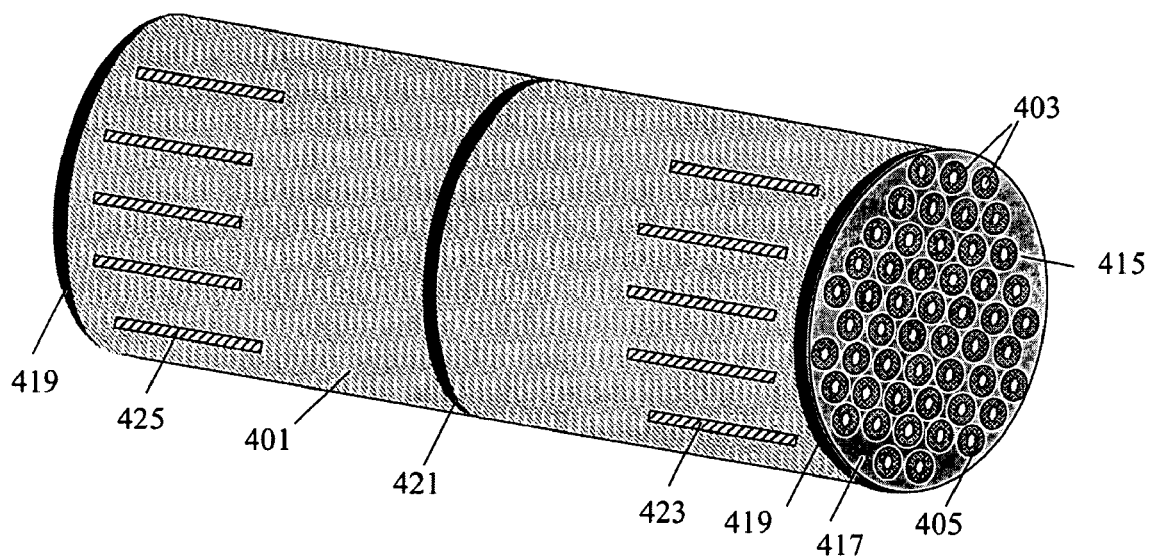
FIG. 9 hereof is yet another representation of a parallel channel contactor of the present invention but in the form of a hollow fiber contactor for TSA applications.
Figure 10:
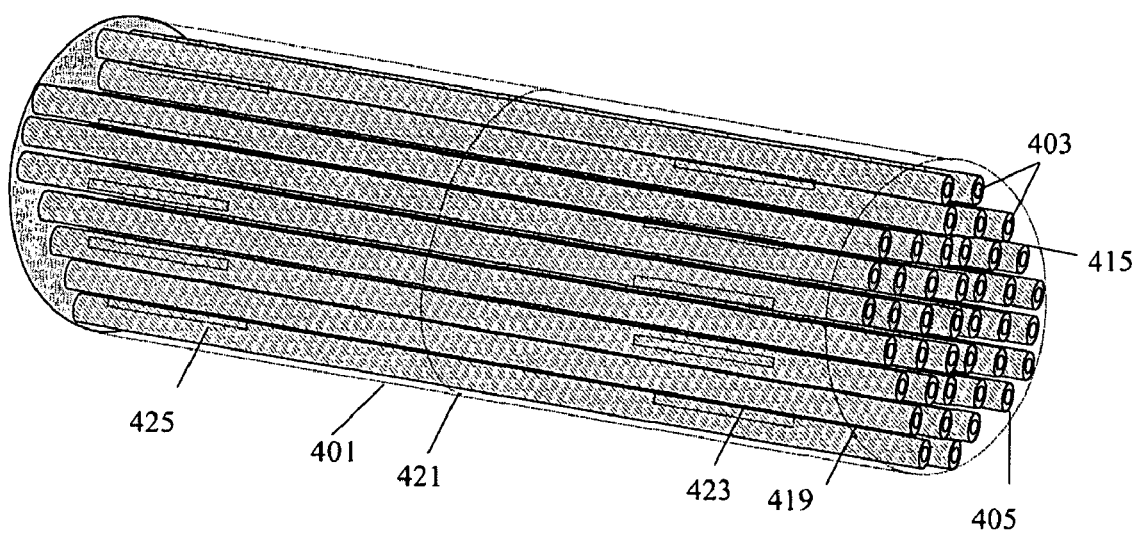
FIG. 10 hereof is another representation of a hollow fiber contactor for TSA as shown in FIG. 9 but with the outer surfaces of the housing for the contactor rendered transparent. Dotted lines are used to indicate the edges of the outer surface.

FIGS. 9 and 10 hereof are representations of a parallel channel contactor of the present invention in the form of a hollow fiber contactor for a TSA process where the adsorbent layer 405 comprises part of the wall of the fiber with a center feed channel 403. In FIG. 10, the outer surfaces of the housing for the contactor 401 are rendered transparent with only dotted lines indicating the edges of the outer surface. The hollow fibers used in this example have a diffusion barrier 415 on their exterior surface and can be manufactured using techniques described for FIG. 4 hereof. The ends of the fiber bundle are potted or embedded in a matrix material 417. This potted array is then sealed into a tubular housing 401. Sealing surfaces 419 are provided at the ends of the tubular housing 401. A sealing surface 421 is also provided in the middle of the housing. Slots 423 and 425 are cut through the wall near the ends of the tubular housing to allow for the flow of heating and cooling fluids.

In operation, the tubular housing is mounted in a TSA or RCTSA module in a manner that seals the ends of the channels as well as the middle of the monolith. Any suitable sealing technology can be used. Non-limiting examples of sealing technologies that can be used in the practice of the present invention include metallic welds, gasketing with materials such as rubbers or carbons, and the use of adhesives such as inorganic cements or epoxies. The module is configured so that a heating or cooling fluid can be flowed inside the hollow tubular housing 401 by introducing it through slots 423 and removing it through slots 425. The heating and cooling fluid will undergo heat exchange with fluid flowing through the hollow fibers which are open at the end of the module. With these sealing arrangements, the tubular housing 401 containing the parallel array of hollow fibers becomes a heat exchanger suitable for use in TSA processes. The fibers have an adsorbent layer 405 with a low volume fraction of mesopores and macropores.

Figure 11:
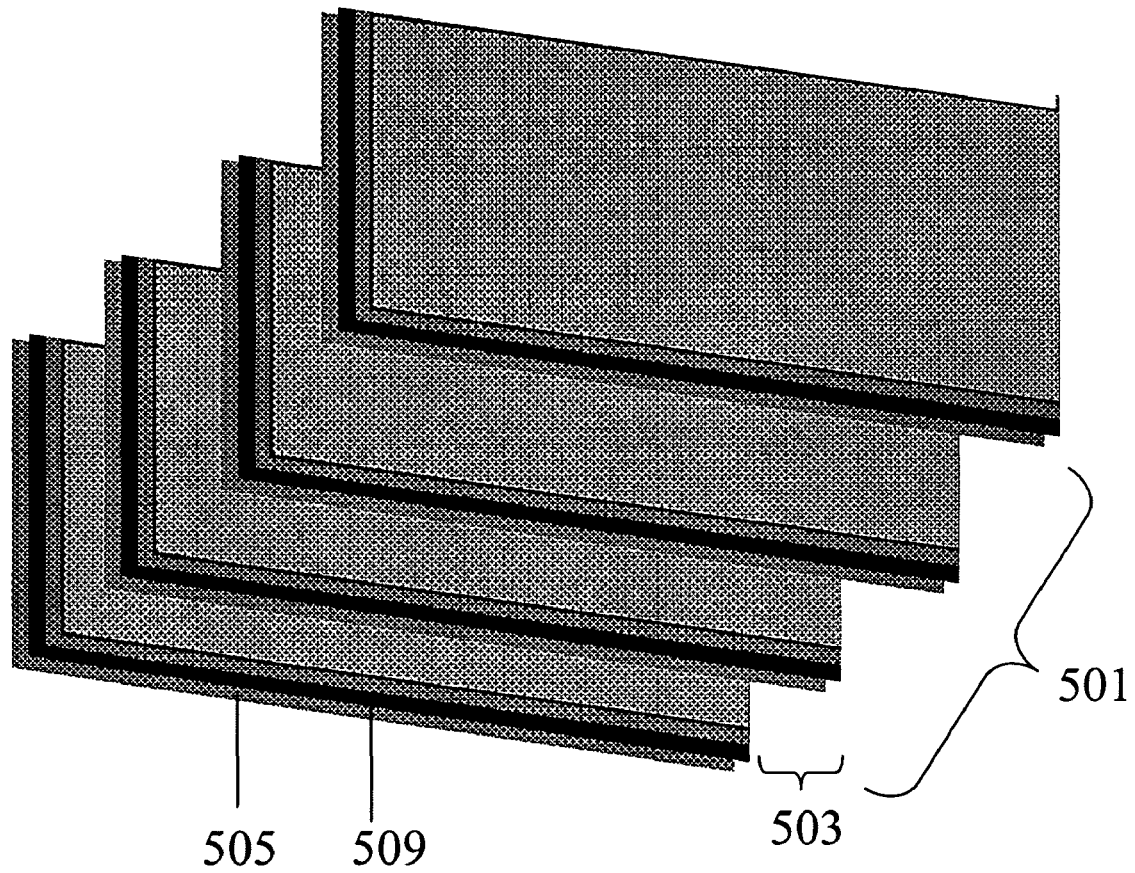
FIG. 11 hereof is a representation of an embodiment of the present invention wherein the parallel contactor is constructed from parallel laminate sheets.

FIG. 11 hereof is a representation of a parallel channel contactor of the present invention in which the parallel channels are formed from laminated sheets containing adsorbent material. Laminates, laminates of sheets, or laminates of corrugated sheets can be used in PSA RCPSA, PPSA or RCPPSA processes. Laminates of sheets are known in the art and are disclosed in U.S. patent applications US20060169142 A1 and U.S. Pat. No. 7,094,275 B2 which are incorporated herein by reference. When the adsorbent is coated onto a geometric structure or components of a geometric structure that are laminated together, the adsorbent can be applied using any suitable liquid phase coating techniques. Non-limiting examples of liquid phase coating techniques that can be used in the practice of the present invention include slurry coating, dip coating, slip coating, spin coating, hydrothermal film formation and hydrothermal growth. When the geometric structure is formed from a laminate, the laminate can be formed from any material to which the adsorbent of the present invention can be coated. The coating can be done before or after the material is laminated. In all these cases the adsorbent is coated onto a material that is used for the geometric shape of the contactor. Non-limiting examples of such materials include glass fibers, milled glass fiber, glass fiber cloth, fiber glass, fiber glass scrim, ceramic fibers, metallic woven wire mesh, expanded metal, embossed metal, surface-treated materials, including surface-treated metals, metal foil, metal mesh, carbon-fiber, cellulosic materials, polymeric materials, hollow fibers, metal foils, heat exchange surfaces, and combinations of these materials. Coated supports typically have two major opposing surfaces, and one or both of these surfaces can be coated with the adsorbent material. When the coated support is comprised of hollow fibers, the coating extends around the circumference of the fiber. Further support sheets may be individual, presized sheets, or they may be made of a continuous sheet of material. The thickness of the substrate, plus applied adsorbent or other materials (such as desiccant, catalyst, etc.), typically ranges from about 10 micrometers to about 2000 micrometers, more typically from about 150 micrometers to about 300 micrometers.

Metallic mesh supports can provide desirable thermal properties of high heat capacity and conductivity which "isothermalize" a PSA, RCPSA, PPSA or RCPPSA cycle to reduce temperature variations that degrade the process when conducted under more adiabatic conditions. Also, metal foils are manufactured with highly accurate thickness dimensional control. The metal foil may be composed of, without limitation, aluminum, steel, nickel, stainless steel or alloys thereof. Hence there is a need for a method to coat metal foils with a thin adsorbent layer of accurately controlled thickness, with necessary good adhesion. One method for doing this is by hydrothermal synthesis. Coating procedures used can be very similar to the way in which zeolite membranes are prepared as discussed above. Zeolite layers grown by hydrothermal synthesis on supports often have cracks which are mesopores and micropores. Examples of these cracks have been shown in FIGS. 5 and 6 hereof. The volume of these pores is often less than about 10 volume % of the film thickness and there is often a characteristic distance between cracks. Another method of coating a metal foil is with thick film coating is slip casting, or doctor blading. An aqueous slurry of prefabricated zeolite particles, binder (for example colloidal silica or alumina), viscosifying agent such as a polymer like polyvinyl alcohol is cast for example onto a metal foil and fired to remove the polymer and cure the binder and zeolite. The product, after firing, is then a bound zeolite film on a metal foil typically containing about 30 to about 40 volume % voids. To make a suitable adsorbent layer, the voids are filled in a subsequent step by coating the bound zeolite film with a polymer or by introducing a liquid into the voids of the bound zeolite film. The final product, after filling the voids with a polymer or liquid, will be an adsorbent layer having the low mesoporosity and microporosity requirements of the present invention.

Another method for coating metal foils with prefabricated zeolite crystals, or microporous particles, is electrophoretic deposition (EPD). EPD is a technique for applying high quality coatings of uniform thickness to metal substrates. The method can be used to apply organic and inorganic particulate coatings on electrically conductive substrates. Slurry compositions containing prefabricated zeolites, or microporous particles, may be electrophoretically applied to a rigid support material, such as by using the method described in Bowie Keefer et al.'s prior Canadian patent application No. 2,306, 311, entitled "Adsorbent Laminate Structure," which is incorporated herein by reference.

Some contactor geometric shapes will require that the adsorbent be applied to the channel surface in a layer using a colloidal binder material or that an entire geometric shape be comprised of the adsorbent plus colloidal binder and containing a plurality of parallel channels. When a colloidal binder is used, the selection of the colloidal material depends on the particular adsorbent used. Colloidal materials capable of functioning as a binder and/or which form a gel are preferred. Such colloidal materials include, without limitation, colloidal silica-based binders, colloidal alumina, colloidal zirconia, and mixtures of colloidal materials. "Colloidal silica" refers to a stable dispersion of discrete amorphous silicon dioxide particles having a particle size ranging from about 1 to about 100 nanometers. Suitable colloidal silica materials also can be surface modified, such as by surface modification with alumina. Another type of colloidal binder suitable for use herein include clay materials, such as palygorskite (also known as attapulgite), which are hydrated magnesium aluminum silicates. Also, inorganic binders may be inert; however, certain inorganic binders, such as clays, used with zeolite adsorbents may be converted in-situ from kaolin binders to zeolite so that the zeolite is self-bound with minimal inert material. In these bound structures, the voids between the colloidal particles form mesopores and the voids between the adsorbent particles form mesopores and/or macropores. A blocking agent can be applied to fill the majority of the mesoporosity and microporosity in these bound layers so that the adsorbent meets the open pore volume requirement of this invention. Organic binders used to bind activated carbon particulates in laminated structures may be pyrolyzed to form a useful carbonaceous adsorbent.

FIG. 11 hereof illustrates an exploded view of an embodiment of the present invention wherein a microporous adsorbent film 505, preferably comprising DDR, is hydrothermally grown on each of both faces of flat metal foils 509, which is preferably fabricated from a corrosion resistant metal such as stainless steel. The separate metal foils 509 with the adsorbent films 505 are fabricated to form a parallel channel contactor 501. Spacers of appropriate size may placed between the metal foils during contactor fabrication so that the channel gap 503 is of a predetermined size. Preferably about half of the volume of the feed channels 503 are filled with a spacer that keeps the sheets substantially evenly spaced apart.

The heat capacity of the metal foils 509 limits the thermal excursions in the process. When $CO_2$ is adsorbed in the adsorbent, heat is released in the amount of the heat of adsorption. This warms the adsorbent films and as the film warms, its temperature rises above that of the metal foils and heat diffuses into the metal foil where it is stored. Desorption of $CO_2$ from the adsorbent is an endothermic process and heat must be supplied in an amount equal to the heat of adsorption. When $CO_2$ desorbs, the temperature of the films falls below that of the metal foils and heat stored in the metal foils flows into the films. The thermal excursion of the adsorbent film is less than +/−10° C. with the contactor dimensions and the process as described in Example 1.

The adsorbent film is composed of individual adsorbent crystals, mesopores (including grain boundaries) and macropores. In this example, the crystals in the film are substantially of the same size. Most of the open volume in the film is comprised of mesoporous cracks with characteristic widths of about 200 angstroms. These mesoporous cracks are substantially evenly distributed throughout the film. The total volume of the mesopores and macropores is about 5 vol. % of the total volume of the adsorbent film.

The present invention can better be understood with reference to the following examples that are presented for illustrative purposes and not to be taken as limiting the invention.

Example 1

Figure 12:
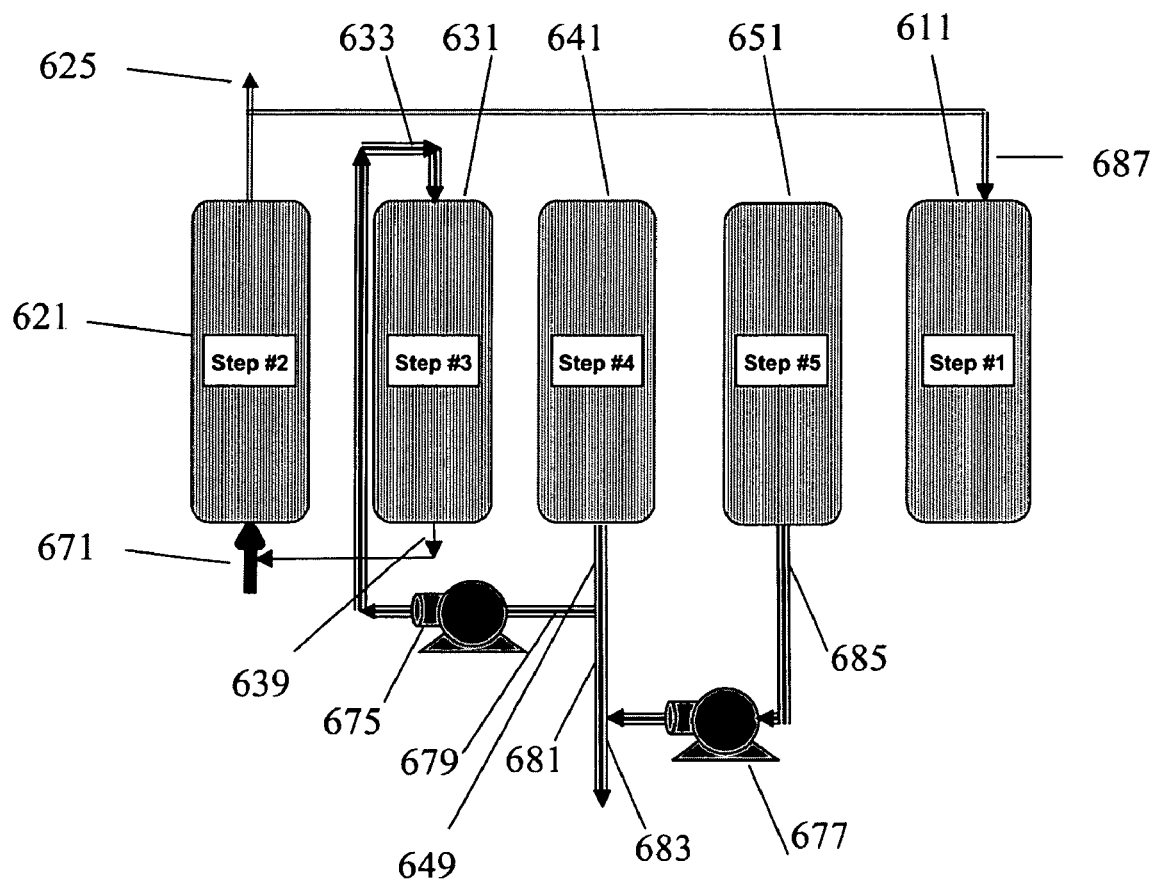
FIG. 12 hereof is a schematic diagram of a preferred five steps PSA/RCPSA process for treating a stream containing about 20 vol. % $CO_2$ and about 80 vol. % $CH_4$.

With a laminated sheet parallel channel contactor described for FIG. 11 hereof, a PSA/RCPSA cycle with five steps is operated to produce a product stream containing about 20 vol. % $CO_2$ and about 80 vol. % $CH_4$. Overall methane recovery for the PSA/RCPSA cycle is computed to be about 95 vol. %. FIG. 12 hereof is a schematic diagram of five different steps in a preferred PSA/RCPSA cycle suitable for use in this invention. In the first step 611 a parallel channel contactor PSA/RCPSA cycle is pressurized with high pressure product gas 687. This pressurization raises the pressure in the parallel channel contactor and fills the contactor with the purified product containing about 20 vol. % $CO_2$ and about 80 vol. % $CH_4$. In a second step 621 a high pressure 51 atmosphere (atm) feed gas 671 is conducted through the parallel channel contactor. During this step 621 the DDR adsorbent layer adsorbs $CO_2$ from the flowing feed gas 671. A purified product 625 flows out of the end of the contactor. The feed gas 671 is flowed at a rate such that as the product 625 emerges from the parallel channel contactor as a concentration front moves through the contactor. Ahead of the front the gas has a composition near that of the product 625. Behind the front the gas has a composition near that of the feed 671. The second step 621 is stopped before this front completely breaks-through the end of the contactor. The amount of feed which emerges from the contactor before this step is halted determines in part the product purity.

At this point, a third step of the cycle 631 is initiated which serves to purge the contactor of feed gas trapped in the contactor channels. The third step 631 also acts, in part, as a partial pressure displacement purge of the contactor. Valves are opened at the top and bottom of the contactor. A pressurized $CO_2$ rich stream 633 flows into the top of the module and gas originally contained in the flow channel 503 of the structured parallel channel contactor flows out 639. The gas fed into the top of the module 633 is a $CO_2$-rich gas produced in later steps 4 and 5 that has been compressed 675 to a pressure slightly greater than the feed pressure (51 atm.). The composition of the gas fed through the top of the contactor is substantially equal to that of the $CO_2$ reject stream 681, containing 97.5 vol. % $CO_2$ and 2.5 vol. % $CH_4$. The gas exiting out the bottom of the contactor has a composition nearer to that of the feed gas 671 (70 vol. % $CO_2$ and 30 vol. % $CH_4$).

As the gas stream entering the module 633 displaces the gas in the flow channels, a compositional front moves from top to bottom of the module. The third step 631 is stopped and a fourth step 641 is begun before, or shortly after, this front breaks through the bottom of the module. The fourth step 641 lets the pressure of the contactor down to an intermediate pressure and recovers some of the $CO_2$ for recompression. In the design discussed in this example, the intermediate pressure is about 22 atm. In the fourth step, a $CO_2$-rich stream 649 exits the module at a pressure of about 22 atm. This stream is split into two streams 679 and 681. Stream 679 is fed to compressor 675 and stream 681 is rejected from the process at a pressure of about 22 atm. Stream 633, that was used to rinse the contactor in the third step of the process 631, is comprised of the gas stream 679 that emerges from compressor 675. As the pressure in the contactor drops towards the outlet pressure of about 22 atm., the flow in streams 679 and 681 decreases. When the flow in these streams has fallen to approximately ¼ of the initial value step 4 is stopped and a step 5 is begun. In the fifth step of the process 651, the module pressure is dropped to about 5 atm. and a $CO_2$-rich stream is recovered 685. This stream 685 can optionally be fed through a compressor 677 that raises the stream pressure to about 22 atm. The stream is then combined with stream 681 and a $CO_2$-rich stream 683 is rejected from the process at a pressure of about 22 atmospheres.

To improve the operation of the process, as well as the pressure at which $CO_2$ is recovered, gas may be recovered in the fifth step 651 using a multi-step process in which the contactor pressure is decreased in a series of pressure equalization steps. Gas from these pressure equalization steps can be recovered as individual gas streams and recompressed. In an example with two pressure equalization steps, one portion of the $CO_2$-rich gas is recovered at a pressure of about 12 atmospheres while the rest is recovered at about 5 atmospheres.

It is also possible to decrease the module pressure in step four 641 using a series of pressure equalization steps. Again, each pressure equalization step can be used to form a gas stream that can either be rejected from the process in stream 683 or recompressed to form stream 633. If pressure equalization steps are employed, it is advantageous to design them to maximize the pressure at which the $CO_2$ reject streams are captured.

Modeling used to predict the performance of the parallel channel contactor uses isotherms for $CO_2$ and $CH_4$ that were measured with well known gravimetric uptake methods, PVT (pressure, volume, temperature) methods, and with analysis of single component gas transport data in DDR membranes. A statistical isotherm shape was found to best describe the single component isotherms for $CO_2$ and $CH_4$. The best fits to the measured isotherms for $CO_2$ and $CH_4$ give saturation capacities of 6 and 5 molecules per cage, respectively, in the DDR zeolite framework. These values correspond to a maximum loading of 5 milli-moles/gram (of DDR) for $CO_2$ and 4.16 milli-moles/gram (of DDR) for $CH_4$. These saturation capacities are consistent with the physical expectation that the maximum possible loading would correspond to $CO_2$ and $CH_4$ filling the pores at a liquid density. A single parameter K, that is analogous to the Henry's constant in a Langmuir isotherm, describes the shape of the statistical isotherm. The K values used for modeling are:

$$K_{CO_2} = 1.93 \times 10^{-10} e^{\frac{25 \times 10^3 \frac{Joule}{Mole}}{RT}} \text{ (in pascals}^{-1})$$

$$K_{CH_4} = 4.25 \times 10^{-10} e^{\frac{17.8 \times 10^3 \frac{Joule}{Mole}}{RT}} \text{ (in pascals}^{-1})$$

where R is the molar gas constant and T is the temperature in Kelvin.

Over a wide range of conditions (less than about 50% of saturation capacity loading), the shape of the statistical and Langmuir isotherms are very similar. For simple modeling of the process given in this example, the statistical isotherm can be supplanted by an equivalent Langmuir isotherm. For modeling competitive adsorption effects, competitive adsorption isotherms can be derived from the single component statistical isotherms using well known techniques.

The single component Stefan-Maxwell transport diffusion coefficients for $CO_2$ and $CH_4$ used in the modeling hereof were:

$$D_{CO_2} = 5.70 \times 10^{-10} e^{-\frac{7.4 \times 10^3 \frac{Joule}{Mole}}{RT}} \text{ (in m}^2/\text{sec)}$$

$$D_{CH_4} = 0.48 \times 10^{-10} e^{-\frac{13.4 \times 10^3 \frac{Joule}{Mole}}{RT}} \text{ (in m}^2/\text{sec)}$$

where R is the molar gas constant and T is the temperature in Kelvin.

It is seen that there is a large difference in the diffusion coefficients of $CO_2$ and $CH_4$ and a smaller difference in the isotherms when these transport parameters are evaluated at a given temperature. From a 50/50 molar mixture of $CO_2$ and $CH_4$ the isotherms slightly favor $CO_2$ adsorption and dramatically favor the diffusional transport of $CO_2$ into the DDR crystals. By controlling the time scale of the adsorption step 621 and the purge displacement step 631, it is possible to take advantage of this difference in diffusion coefficients and improve the selectivity of the process. By controlling these time steps, a kinetic separation of $CO_2$ and $CH_4$ can be achieved that takes advantage of differences, in diffusivity of these molecules. The class of 8-ring zeolites preferred for the removal of $CO_2$ from natural gas will have a large difference in $CO_2$ and $CH_4$ diffusion coefficients. This example illustrates a particular RCPSA cycle that can be tuned to achieve a kinetic separation of $CO_2$ and $CH_4$, however, other swing adsorption cycles are possible. A parameter that can be used to evaluate the ability of a given material to produce a kinetic separation is the ratio of diffusion coefficients for the components that are to be separated and the diffusion coefficients are evaluated at the temperature and pressure of the intended process, $$\kappa = \frac{D_{CO_2}}{D_{CH_4}}$$

It is preferred that the material be chosen to have a value of $\kappa$ for $CO_2$ and methane separation greater than 10 at the operating temperature. More preferably the material is chosen to have a value of $\kappa$ greater than 25 at the operating temperature. More preferably the material is chosen to have a value of K greater than 50 at the operating temperature.

In order to take advantage of the intrinsic kinetic selectivity of the preferred class of 8-ring zeolite materials for removal of $CO_2$ from natural gas, the crystals forming the contactor must be of substantially the same size. If they have widely different sizes, some will substantially fill with $CH_4$ during the adsorption step 621, resulting in increased methane loss during the desorption step 651. It is therefore preferred that the standard deviation of the volume of the individual crystallites in the DDR film forming the adsorbent layer 505 (as seen in FIG. 11) be less than 100% of the volume of an average crystallite in order to increase methane recovery in the process. In a more preferred embodiment, the standard deviation of the volume of the crystallites in the DDR film forming the adsorbent layer 505 is less than 50% of the volume of an average crystallite. In the most preferred embodiment, the standard deviation of the volume of the crystallites in the DDR film forming the adsorbent layer 505 is less than 10% of the volume of an average crystallite. The most preferred embodiment was chosen to model the PSA cycle described in this example.

With this type of adsorbent, the time for steps 621 and 631 is set by the average crystal size in the adsorbent. It is preferred that the time step be chosen so that adsorbed $CO_2$ in the DDR has time to equilibrate with gaseous $CO_2$ in the feed channel 503 but the methane does not have time to equilibrate. The time for $CO_2$ to achieve 90% approach to equilibrium (following a change in surface concentration) within a single DDR crystal that has rapid diffusion path to the gas in the contactor is;

$$\tau_{90} = 0.183 r^2 / D_{CO_2}$$

where r is the average DDR crystal radius and $D_{CO_2}$ is the diffusion coefficient of $CO_2$ at the operating temperature. It is preferred that the time for steps 621 and 631 be in a range from $0.5 \tau_{90}$ to $10 \tau_{90}$ and it is more preferred that the time for steps 621 and 631 be in a range from $1 \tau_{90}$ to $5 \tau_{90}$. For modeling, a time step of $1.5 \tau_{90}$ was chosen for steps 621 and 631. The numerical value of the time step is then set by the crystal size. It is preferred that the average DDR crystal size be in a range from about 0.005 μm to about 100 μm. It is more preferred that the average DDR crystal size be in a range from about 0.5 μm to about 50 μm and it is most preferred that the average DDR crystal size be in a range from about 1 μm to about 10 μm. For modeling an average DDR crystal size of 1 μm was used.

Several different treatments of the molecular transport into and out of the adsorbent layer were developed and results of the different modeling approximations were compared. The most exact treatment solved the time dependent fundamental multi-component transport equations into and out of the DDR zeolite layer at all points along the feed channel for every time step in the process. For this model the DDR film was idealized as fins along the side of the channel with 200 angstrom gaps between the fins. The mesopores formed by these 200 angstrom gaps occupied 5% of the volume of the adsorbent layer. On a grid encompassing 500,000 points, the fundamental time dependent transport equations were solved for this geometry. Three pressure equalization steps were used in the blow-down step 651 for process modeling. Pressure equalizations at 15, 10 and 5 atmospheres were employed. It was determined that the thermal excursion in the adsorption step was 10° C. The methane recovery was computed as the ratio of the methane molar flow rate in purified product stream 625 to that in the feed stream 671 entering the process. The model using the most exact treatment of transport showed a 96% methane recovery. The average pressure at which molecules were recovered in streams 681 and 685 was found to be 12.5 atmospheres.

This modeling approach provides a much more exact solution than the linear driving force (LDF) models that are conventionally used to model PSA processes. Using knowledge of the most exact solution, a simpler model has been constructed that can readily be used by one skilled in the art to compute methane recoveries. In the adsorption step 621, the simple model separately treats the equilibration of $CO_2$ and $CH_4$ in the feed channel within the DDR crystals forming the adsorbent layer. The amount of $CO_2$ adsorbed in the DDR crystals is taken to be 80% of the amount that might be expected if the $CO_2$ adsorbed in the DDR were fully equilibrated with the gaseous feed entering the process 671 at a temperature that is 10° C. higher than the feed temperature. The amount of $CH_4$ adsorbed in the DDR crystals is 1% of the amount that might be expected if the $CH_4$ adsorbed in the DDR has fully equilibrated with the gaseous feed entering the process 671 at a temperature that is 10° C. higher than the feed temperature. In the simple model gas filling the mesopores and macropores in the laminate at the end of the adsorption step 621 is not recovered. For the simple model, the $CO_2$ purge used in step 631 displaces all of the methane left in the feed channel into stream 639. With these approximations, the methane recovery from the process is predicted to be 95%. This closely agrees with the exact model and the model provides a simple method for one skilled in the art to evaluate the effect of changing the mesopore and macropore volume of the adsorbent.

Optionally when the $CO_2$ reject stream 683 is sequestered it is preferred to capture the $CO_2$ at a pressure that is more than 1/10 of the partial $CO_2$ pressure in the feed. In a more preferred embodiment the pressure at which the $CO_2$ is captured is more than 1/4 of the $CO_2$ partial pressure in the feed.

Example 2

The process of Example 1 is repeated except the feed and product specifications are held constant and the volume fraction of mesopores and macropores in the adsorbent are increased from 5% to 10%. The predicted methane recovery is found to fall from 95% (in Example 1) to 92%.

Example 3

The process of Example 1 is repeated except the feed and product specifications are held constant and the volume fraction of mesopores and macropores in the adsorbent are increased from 5% to 15%. The predicted methane recovery is found to fall from 95% (in Example 1) to 88%.

Example 4

The process of Example 1 is repeated except the feed and product specifications are held constant and the volume fraction of mesopores and macropores in the adsorbent are increased from 5% to 20%. The predicted methane recovery is found to fall from 95% (in Example 1) to 85%.

Example 5

The process of Example 1 is repeated except the feed and product specifications are held constant and the volume fraction of mesopores and macropores in the adsorbent are increased from 5% to 25%. The predicted methane recovery is found to fall from 95% (in Example 1) to 81%.

Example 6

The process of Example 1 is repeated except the feed and product specifications are held constant and the volume fraction of mesopores and macropores in the adsorbent are increased from 5% to 30%. The predicted methane recovery is found to fall from 95% (in Example 1) to 77%.

Example 7

The process of Example 1 is repeated except the feed and product specifications are held constant and the volume fraction of mesopores and macropores in the adsorbent are increased from 5% to 35%. The predicted methane recovery is found to fall from 95% (in Example 1) to 73%.

Example 8

The process of Example 1 is repeated except the feed and product specifications are held constant and the volume fraction of mesopores and macropores in the adsorbent are decreased from 5% to 2.5%. The predicted methane recovery is found to increase from 95% (in Example 1) to 97%.

Example 9

The process of Example 1 is repeated but the feed specification is held constant and purity of methane in the product stream 625 is increased from 80% $CH_4$/20% $CO_2$ to 90% $CH_4$/10% $CO_2$. This is done by changing the feed flow rates and the degree to which compositional fronts are allowed to break-through before steps 621 and 631 are stopped. With a 5% volume fraction of mesopores and macropores in the adsorbent the predicted methane recovery is 94%.

Example 10

The process of Example 1 is followed but the feed specification is held constant and purity of methane in the product stream 625 is increased from 80% $CH_4$/20% $CO_2$ to 90% $CH_4$/10% $CO_2$. This is done by changing the feed flow rates and the degree to which compositional fronts are allowed to break-through before steps 621 and 631 are stopped. With a 10% volume fraction of mesopores and macropores in the adsorbent the predicted methane recovery is 90%.

Example 11

This example illustrates use of a parallel contactor of the present invention in a separation process that produces relatively high pressure products and high methane recoveries from $N_2$ containing natural gas stream. In processing natural gas, the amount of $N_2$ that has to be removed depends on the concentration in the field and the way in which the gas is transported to market (i.e., liquefied natural gas vs. pipeline). This example will consider a natural gas stream containing a small amount (<5%) of impurities (for example $H_2O$ and mercury compounds) other than $N_2$. These impurities are removed in initial processing steps using conventional separation techniques. The gas stream fed to the parallel contactor of the present invention has a composition of 70% $CH_4$ and 30% $N_2$. The flowing gas stream is fed to the contactor at a pressure of 100 atmospheres and a temperature of 50° C.

The contactor is comprised of laminated flat sheets of the type described above and a schematic diagram of the type of sheet used in the present example is shown in FIG. 11 hereof. Using the methods described above a 50 µm thick DDR film 505 with an Si/Al ratio greater than 100 is hydrothermally grown on each of both faces of a 100 µm thick flat metal foil 509 (for example stainless steel). The metal foils 509 with the DDR films 505 are laminated together 501 to form a parallel channel contactor. During lamination, spacers are placed between the metal foils so that the channel gap 503 is 50 µm across. Approximately half the volume of the feed channels 503 are filled with spacers that keep the sheets substantially evenly spaced 50 µm apart.

The heat capacity of the metal foil 509 limits the thermal excursions in the process. When $N_2$ is adsorbed in DDR it releases heat in the amount of the heat of adsorption. This warms the DDR film. The DDR film warms to a temperature above that of the metal foil and heat diffuses into the metal foil where it is stored. Desorption of $N_2$ from DDR is an endothermic process and heat must be supplied in the amount of the heat of the adsorption. When $N_2$ desorbs the temperature of the DDR film falls below that of the metal foil and heat stored in the foil flows into the DDR film. With the contactor dimensions and the process described in this example, the thermal excursion of the DDR film is expected to be less than +/−5° C. Due to the smaller heat of adsorption for $N_2$ (compared to $CO_2$) this temperature rise is less than that of the description for Example 1 above.

The DDR film is comprised of individual DDR crystals, mesopores (including grain boundaries) and macropores. In this example, the crystals in the DDR film are substantially of the same size. Most of the open volume in the film is comprised of mesoporous cracks with characteristic widths of 200 angstroms. These mesoporous cracks are substantially evenly distributed throughout the film. The total volume of the mesopores and macropores is 2.5% of the total volume of the in the DDR film.

Figure 13:
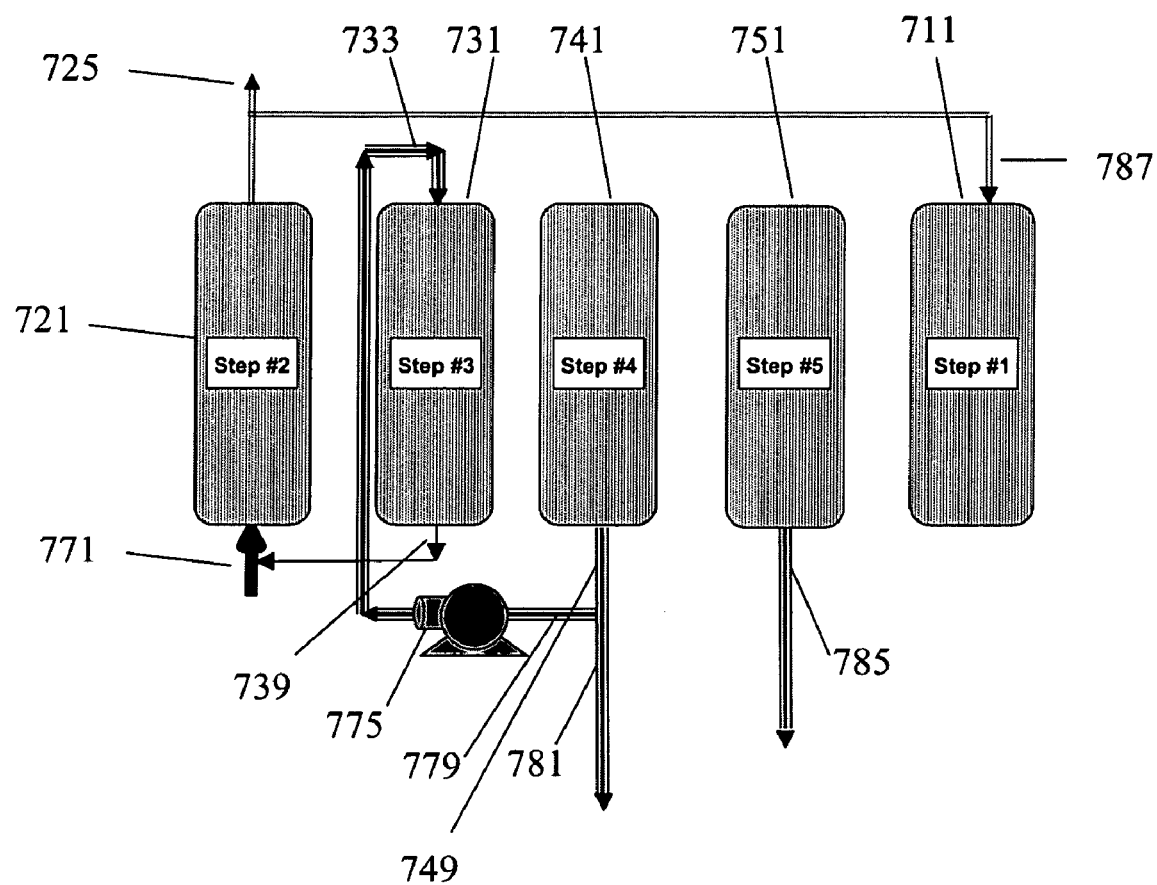
FIG. 13 hereof is a schematic diagram of a preferred five steps PSA/RCPSA process for treating a stream containing about 2 vol. % $N_2$ and about 98 vol. % $CH_4$.

Using this parallel channel contactor, a PSA/RCPSA cycle with five different steps is operated to produce product stream containing 2% $N_2$ and 98% $CH_4$. Overall methane recovery for the PSA/RCPSA cycle is computed to be 91%. FIG. 13 hereof shows a schematic diagram of the five different steps in the PSA/RCPSA cycle. In the first step 711a parallel channel contactor PSA/RCPSA cycle is pressurized with high pressure product gas 787. This pressurization raises the pressure in the parallel channel contactor and fills the contactor with the purified product containing 2% $N_2$ and 98% $CH_4$. In a second step 721a high pressure 100 atm feed gas 771 is flowed through the contactor. During this step 721 the DDR adsorbent layer removes $N_2$ from the flowing feed gas 771. A purified product 725 flows out of the end of the contactor. The feed gas 771 is flowed at a rate such that as the product 725 emerges from the contactor a concentration front moves through the contactor. Ahead of the front the gas has a composition near that of the product 725. Behind the front the gas has a composition near that of the feed 771. Before this front completely breaks through the end of the contactor the second step 721 is stopped. The amount of feed which emerges from the contactor before this step is halted determines in part the product purity.

At this point, a third step of the cycle 731 is initiated which serves to purge the contactor of feed gas trapped in the contactor channels. The third step 731 also acts in part as a partial pressure displacement purge of the contactor. Valves are opened at the top and bottom of the contactor. A pressurized $N_2$ rich stream 733 flows into the top of the module and gas originally contained in the flow channel 503 (of FIG. 11 hereof) of the structured parallel channel contactor flows out 739. The gas fed into the top of the module 733 is a $N_2$ rich gas produced in later steps (4 and 5) that has been compressed 775 to a pressure slightly greater than the feed pressure (100 atm.). Composition of the gas fed in through the top of the contactor is nearly that of the $N_2$ reject stream 781. The gas exiting out the bottom of the contactor has a composition nearer to that of the feed gas 771 (30% $N_2$ and 70% $CH_4$).

As the gas stream entering the module 733 displaces the gas in the feed channel a compositional front moves from top to bottom of the module. Before or shortly after this front breaks through the bottom of the module the third step 731 is stopped and a fourth step 741 is begun. The fourth step 741 lets the pressure of the contactor down to an intermediate pressure and recovers some of the $N_2$ for recompression. In the design discussed in this example the intermediate pressure is 30 atm. In the fourth step a $N_2$ rich stream 749 exits the module at a pressure of 30 atm. This stream is split into two streams 779 and 781. Gas in stream 779 is fed to a compressor 775 and gas in stream 781 is rejected from the process at a pressure of 30 atm. In an optimization of this process a pressure in step 741 is chosen that minimizes the amount of gas flowing in stream 781. Stream 733 that was used to rinse the contactor in the third step of the process 731 is comprised of the gas stream 779 that emerged from the compressor 775. As the pressure in the contactor drops towards the outlet pressure of 30 atm, the flow in streams 779 and 781 decrease. When the flow in these streams has fallen to approximately ¼ of the initial value the fourth step is stopped and a fifth step is begun. In the fifth step of the process 751 the module pressure is dropped to 1.2 atm and a $N_2$ rich stream is recovered 785.

To improve the operation of the process, as well as the pressure at which $N_2$ is recovered, gas may be recovered in the fifth step 751 using a multi-step process in which the contactor pressure is decreased in a series of pressure equalization steps. In an example with two pressure equalization steps, one portion of the $N_2$ rich gas is recovered at a pressure of 12 atmospheres while the rest is recovered at 1.2 atmospheres.

It is also possible to decrease the module pressure in step four 741 with a series of pressure equalization steps. Again each pressure equalization step can be used to form a gas stream that can either be rejected from the process in stream 783 or recompressed to form stream 733. If pressure equalization steps are employed is it advantageous to design them to maximize the pressure at which the $N_2$ reject streams are captured.

The modeling used to predict the performance of the contactor used isotherms for $N_2$ and $CH_4$ that were measured with well known gravimetric uptake methods, PVT (pressure, volume, temperature) methods, and with analysis of single component transport data in DDR membranes. A statistical isotherm shape was found to best describe the single component isotherms for $N_2$ and $CH_4$. The best fits to the measured isotherms for $N_2$ and $CH_4$ give saturation capacities of 5 molecules par cage in the DDR zeolite framework. These values correspond to a maximum loading of 4.17 milli-moles/ gram (of DDR). These saturation capacities are consistent with the physical expectation that the maximum possible loading would correspond to $N_2$ and $CH_4$ filling the pores at a liquid density. A single parameter K, that is analogous to the Henry's constant in a Langmuir isotherm, describes the shape of the statistical isotherm. The K values used for modeling are:

$$K_{N_2} = 3.79 \times 10^{-9} e^{-\frac{9.6 \times 10^3 \frac{Joule}{Mole}}{RT}} \text{ (in pascals}^{-1})$$

$$K_{CH_4} = 4.25 \times 10^{-10} e^{-\frac{17.8 \times 10^3 \frac{Joule}{Mole}}{RT}} \text{ (in pascals}^{-1})$$

where R is the molar gas constant and T is the temperature in Kelvin.

Over a wide range of conditions the shape of the statistical and Langmuir isotherms are very similar. For simple modeling of the process given in this example, the statistical isotherm can be supplanted by an equivalent Langmuir isotherm. For modeling competitive adsorption effects, competitive adsorption isotherms can be derived from the single component statistical isotherms using well known techniques.

The single component Stefan-Maxwell transport diffusion coefficients for $N_2$ and $CH_4$ used in the modeling were $$D_{N_2} = 0.48 \times 10^{-10} e^{-\frac{1.5 \times 10^3 \frac{Joule}{Mole}}{RT}} \text{ (in m}^2\text{/sec)}$$

$$D_{CH_4} = 0.48 \times 10^{-10} e^{-\frac{13.4 \times 10^3 \frac{Joule}{Mole}}{RT}} \text{ (in m}^2\text{/sec)}$$

where R is the molar gas constant and T is the temperature in Kelvin.

When these transport parameters are evaluated at a given temperature, it is seen that there is a large difference in the diffusion coefficients of $N_2$ and $CH_4$ and a smaller difference in the isotherms. From a 50/50 molar mixture of $N_2$ and $CH_4$, the isotherms slightly favor $CH_4$ adsorption but dramatically favor the diffusional transport of $N_2$ into the DDR crystals. By controlling the time scale of the adsorption step 721 and the purge displacement step 731, it is possible to take advantage of this difference in diffusion coefficients and improve the selectivity of the process. By controlling these time steps a kinetic separation of $N_2$ and $CH_4$ can be achieved that takes advantage of differences in diffusivity of these molecules. The preferred class of 8-ring zeolite materials for removal of $N_2$ from natural gas will have a large difference in $N_2$ and $CH_4$ diffusion coefficients. This example illustrates a particular RCPSA cycle that can be tuned to achieve a kinetic separation of $N_2$ and $CH_4$; however, other swing adsorption cycles are possible. A parameter that can be used to evaluate the ability of a given material to produce a kinetic separation is the ratio of the single component diffusion coefficients for the components. The ratio is evaluated at the temperature of the intended process, $$\kappa = \frac{D_{N_2}}{D_{CH_4}}$$

Values of κ for DDR for nitrogen and methane separation at several different temperatures are given in the table below:

| Temperature (C.) | κ |
|---|---|
| 20 | 130 |
| 40 | 100 |
| 60 | 75 |
| 80 | 60 |
| 100 | 50 |

For the preferred class of 8-ring zeolite materials for removal of $N_2$ from natural gas $\kappa_{N2/CH4}$ is a function of temperature. It is preferred that the material be chosen to have a value of $\kappa_{N2/CH4}$ greater than 5 at the operating temperature. More preferably the material is chosen to have a value of $\kappa_{N2/CH4}$ greater than 20 at the operating temperature. Even more preferably the material is chosen to have a value of $\kappa_{N2/CH4}$ greater than 50 at the operating temperature.

In order to take advantage of the intrinsic kinetic selectivity of the preferred class of 8-ring zeolite materials for removal of $N_2$ from natural gas, the crystals forming the contactor must have substantially the same size. If they have widely different sizes some will substantially fill with $CH_4$ during the adsorption step 721, resulting in increased methane loss during the desorption step 751. To increase methane recovery in the process it is then preferred that the standard deviation of the volume of the individual crystallites in the DDR film forming the adsorbent layer 505 be less than 100% of the volume of an average crystallite. In a more preferred embodiment the standard deviation of the volume of the crystallites in the DDR film forming the adsorbent layer 505 is less than 50% of the volume of an average crystallite. In the most preferred embodiment the standard deviation of the volume of the crystallites in the DDR film forming the adsorbent layer 505 is less than 10% of the volume of an average crystallite. The most preferred embodiment was chosen to model the PSA cycle described in this example.

With this type of adsorbent, the time for steps 721 and 731 is set by the average crystal size in the adsorbent. It is preferred that the time step be chosen so that adsorbed $N_2$ in the DDR has time to equilibrate with gaseous $N_2$ in the feed channel 503 but the $CH_4$ does not have time to equilibrate. The time for $N_2$ or $CH_4$ achieve 90% approach to equilibrium (following a change in surface concentration) within a single DDR crystal that has rapid diffusion path to the gas in the contactor is;

$$\tau_{90} = 0.183 r^2 / D_{N2}$$

and $$\tau_{90} = 0.183 r^2 / D_{CH4}$$

where r is the average DDR crystal radius and $D_{N2}$ and $D_{CH4}$ are the diffusion coefficients of $N_2$ and $CH_4$ at the operating temperature. If there are no external mass transfer limitations, the equilibration times for different crystallite sizes are given in the table below:

| Crystallite Size (μm) | Nitrogen $\tau_{90}$ (seconds) | Methane $\tau_{90}$ (seconds) |
|---|---|---|
| 1.5 | 0.01 | 2 |
| 5 | 0.1 | 22 |
| 10 | 0.45 | 91 |
| 25 | 2.8 | 570 |
| 40 | 7.3 | 1460 |

It is preferred that for $N_2$ the time for steps 721 and 731 be in a range from $0.5\,\tau_{90}$ to $10\,\tau_{90}$ and it is more preferred that the time for steps 721 and 731 be in a range from $1\,\tau_{90}$ to $5\,\tau_{90}$. For modeling, a time step of $1.5\,\tau_{90}$ was chosen for steps 721 and 731. The numerical value of the time step is then set by the crystal size. It is preferred that the average DDR crystal size be in a range from 0.005 µm to 100 µm. It is more preferred that the average DDR crystal size be in a range from 0.5 µm to 50 µm and it is most preferred that the average DDR crystal size be in a range from 1 µm to 10 µm. For modeling an average DDR crystal size of 5 µm was used.

A simplified modeling approach similar to that described above was used. In the adsorption step 721, the simple model separately treats the equilibration of $N_2$ and $CH_4$ in the feed channel with the DDR crystals forming the adsorbent layer. The amount of $N_2$ adsorbed in the DDR crystals is taken to be 80% of the amount that might be expected if the $N_2$ adsorbed in the DDR has fully equilibrated with the gaseous feed entering the process 771 at a temperature that is 110° C. higher than the feed temperature. The amount of $CH_4$ adsorbed in the DDR crystals is 1% of the amount that might be expected if the $CH_4$ adsorbed in the DDR has fully equilibrated with the gaseous feed entering the process 771 at a temperature that is 10° C. higher than the feed temperature. In the simple model, gas filling the mesopores and macropores in the laminate at the end of the adsorption step 721 is not recovered. Also, for the simple model the $N_2$ purge used in step 731 displaces all of the methane left in the feed channel into stream 739. With these approximations the methane recovery from the process is predicted to be 91%. This closely agrees with the exact model and the model provides a simple method for one skilled in the art to evaluate the effect of changing the mesopore and macropore volume of the adsorbent.

Example 12

The process of Example 11 is followed but the feed and product specifications are held constant and the volume fraction of mesopores and macropores in the adsorbent are increased from 2.5% to 5%. The predicted methane recovery is found to fall from 91% (in Example 11) to 90%.

Example 13

The process of Example 11 is followed but the feed and product specifications are held constant and the volume fraction of mesopores and macropores in the adsorbent are increased from 2.5% to 15%. The predicted methane recovery is found to fall from 91% (in Example 11) to 84%.

Example 14

The process of Example 11 is followed but the feed and product specifications are held constant and the volume fraction of mesopores and macropores in the adsorbent are increased from 2.5% to 20%. The predicted methane recovery is found to fall from 91% (in Example 11) to 81%.

Example 15

The process of Example 11 is followed but the feed and product specifications are held constant and the volume fraction of mesopores and macropores in the adsorbent are increased from 2.5% to 25%. The predicted methane recovery is found to fall from 91% (in Example 11) to 78%.

Example 16

Figure 14:
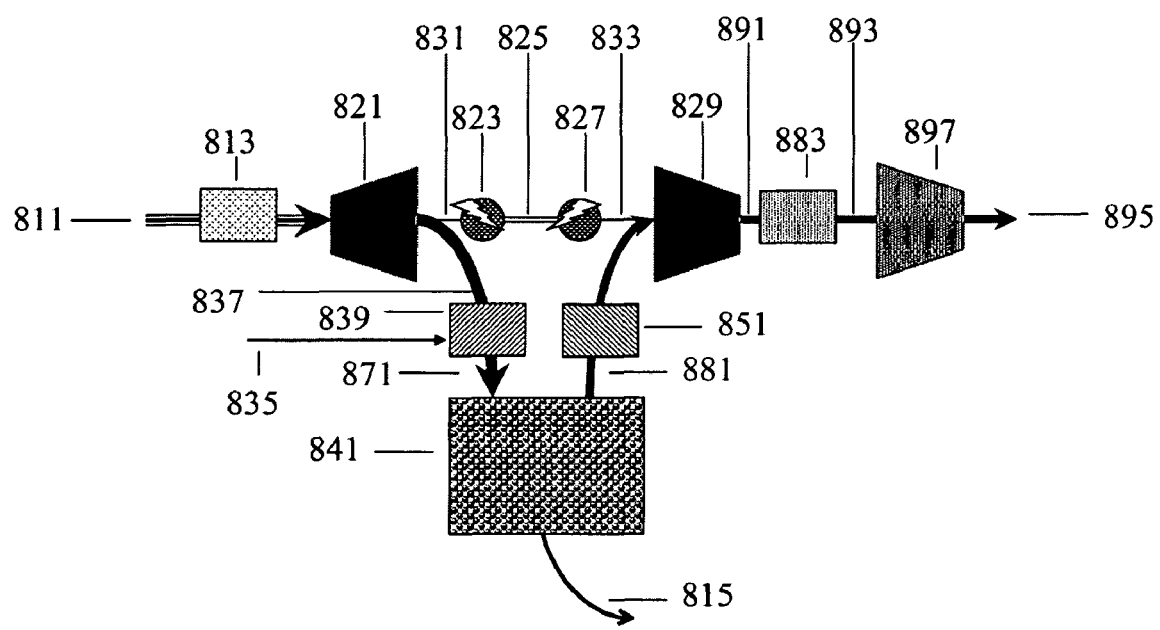
FIG. 14 hereof is a schematic diagram of an integrated process utilizing a turboexpander and a PSA process of the present invention.

This example illustrates the use of a turboexpander to condition sour gas (i.e., natural gas-containing $H_2S$ and $CO_2$) so that PSA can operate in the window that optimizes methane recovery. FIG. 14 hereof shows a process scheme in which a turboexpander is used to set the pressure and temperature of a sour gas that is separated in a PSA apparatus. A sour gas stream 811 with a temperature of 100° C. and a pressure of 1,500 psi is produced from a gas field and fed to the process. The $CO_2$ content of the stream is 66 mole % and the $H_2S$ concentration is 2 mole %. Water is present at its saturated vapor pressure, and the concentration of the heavy hydrocarbons is 2 mole %. The heavy hydrocarbons contain a small fraction of waxy species with carbon numbers as large as 36. For this stream 811, $CO_2$ comprises the majority of the heavy component that will be removed by a kinetically controlled PSA process. If DDR zeolite is used as the adsorbent in the kinetically controlled PSA, the loading in the DDR zeolite from $CO_2$ partial pressure in stream 811 would be in excess of $0.6\,q_s$ and the slope of the $CO_2$ isotherm would be:

$$\frac{\partial q_{CO_2}}{\partial P_{CO_2}} \cong .02\,K_{CO_2}\,q_s$$

where $K_{CO_2}$ is the Henry's constant for $CO_2$, and $q_s$ is the saturated loading for $CO_2$ in DDR.

To bring the stream into a more preferred window of operation the stream is passed through a turboexpander 821 that reduces the stream pressure to about 500 psi. In a preferred embodiment, the turboexpander 821 is designed to have a radial inflow. Radial inflow turbine designs suitable for use in this process can be found in Perry's Chemical Engineers' Handbook (7th Edition© 1997 McGraw-Hill edited by R. H. Perry and D. W. Green). During the approximately isentropic expansion, the gas temperature falls significantly and liquids may fall out of the gas stream due to a change in the dew point and reduction in temperature. Radial inflow turbine designs can be operated so that liquids falling out of the gas stream will not impede the operation of the turboexpander. In this example, the power generated by the turboexpander is coupled through a shaft 831 to and an electric generator 823. In an alternative embodiment, the power from the turboexpander shaft is coupled to a compressor instead of an electric generator.

Before the stream is passed through turboexpander 821, it may optionally be sent through a process 813 to remove any particles, or a portion of the wax, or optionally some of the heavy hydrocarbons, $H_2S$ and/or water. The absolute temperature of the stream 837 coming out of the turboexpander is approximately 30% less than feedstream 811, and it contains a mixture of gas and liquid droplets. Stream 837 is then sent to a process block 839 that at least removes the liquid droplets from the stream. Liquid droplet removal can be accomplished through a variety of methods including coalescing filters, settling drums, static centrifugation, and electrostatic precipitation. The process block 839 also contains equipment to increase the temperature of stream 837. Means of heating the stream within process block 839 include heat exchangers such as shell and tube heat exchangers as well as other types of heat exchangers including the many varieties discussed in Perry's Chemical Engineers' Handbook (7th Edition© 1997 McGraw-Hill edited by R. H. Perry and D. W. Green), including packed bed heat exchangers. Alternatively, stream 837 may be by mixing it with a separately formed hot gas stream 835. When heat exchangers are used in process block 839, it is preferred that they extract heat from stream 881, 891, 895, or some combination thereof using a multi-pass heat exchanger. Optionally, the heat exchanger used in process block 839 can extract heat from an optional stream 835. In one embodiment stream 835 is produced by combusting hydrocarbon and air or oxygen enriched air. In another embodiment, stream 835 is produced by heat exchanging a working fluid or gas with high temperature combustion products. Besides increasing the temperature of stream 837 and removing liquid droplets, process block 839 can optionally be configured to remove heavy hydrocarbons, water vapor, or $H_2S$ from the gas phase. In this example, process block 839 is configured to remove liquid droplets, and to heat stream 837 to a temperature of 90° C.

The physical composition of stream 871 coming from process block 839 is such that if DDR zeolite is used as the adsorbent in a kinetically controlled PSA, the loading in the DDR zeolite from $CO_2$ partial pressure in stream 871 would be in excess of 0.5 $q_s$ and the slope of the $CO_2$ isotherm would be:

$$\frac{\partial q_{CO_2}}{\partial P_{CO_2}} \cong .07\, K_{CO_2}\, q_s$$

where $K_{CO2}$ is the Henry's constant for $CO_2$ at 90° C. and $q_s$ is the saturated loading for $CO_2$ in DDR.

This operating condition is in a more desirable range for high methane recovery with a kinetically controlled PSA process than that for stream 811. PSA unit 841 is used to separate most of the $CO_2$ and a fraction of the $H_2S$ out of stream 871. In a preferred embodiment, PSA unit 841 contains a parallel channel contactor with an adsorbent having an open volume fraction of mesopores and macropores that is less than 10%. In a preferred embodiment, the microporous adsorbent in the contactor is an 8-ring zeolite and PSA unit 841 is a RCPSA unit that is operated in a kinetically controlled mode. In a preferred embodiment more than 90% of the methane and heavy hydrocarbon fed to PSA unit 841 is recovered in the methane enriched stream 815. In a an even more preferred embodiment, more than 95% of the methane and heavy hydrocarbon fed to PSA unit 841 is recovered in the methane enriched stream 815. In this example the molar ratio of methane to $CO_2$ in the methane enriched stream 815 is greater than 9:1. Depending upon final use, the methane enriched stream 815 may be further processed or purified in other processes. The $CO_2$ enriched stream 881 coming from the PSA 841 can be sent through an optional process block 851 to remove water vapor.

The optional process block 851 can also contain one side of a heat exchanger that is used to provide heat to the heat exchanger in process block 839. The $CO_2$ in stream 881 is ultimately sent to a compressor 829. The compressor 829 is preferably driven by the energy recovered from the turboexpander 821. In this example energy produced by the electric generator 823 is sent through a power transmission line 825 to power a motor 827 that is shaft-coupled via 833 to the compressor 829. As was previously mentioned in an alternative embodiment, the compressor 829 can be shaft-coupled to the turboexpander 821. Because of the work of compression, the temperature of the stream 891 coming out of the compressor 829 is greater than that of stream 881. It can be advantageous to cool this stream 891 before further compression to pressures required for $CO_2$ disposal/sequestration. Cooling can be accomplished with an optional process block 883 that contains one side of a heat exchanger that is used to provide heat to the heat exchanger in process block 839. If needed, process block 883 can contain equipment such as a glycol dehydration unit to reduce the corrosivity of the gas mixture. To raise the pressure of the $CO_2$ rich gas stream 893 to the level needed for $CO_2$ disposal/sequestration, a final compressor 897 is provided. The compressed $CO_2$ rich gas stream 895 is injected into an underground formation for $CO_2$ disposal/sequestration, or for enhanced oil recovery.

Example 17

This example illustrates use of a parallel contactor in a separation that removes $CO_2$ from flue gas in a thermal swing adsorption process. Flue gas or stack gas is emitted in a wide variety of industrial processes. Pressure of the flue gas is typically slightly above atmospheric pressure and is generally less than two atmospheres. The temperature of the flue gas is typically in a range from about 150° C. to about 250° C. The major components in the gas are typically $N_2$, $O_2$, $CO_2$, and $H_2O$, Small quantities of pollutants such as $NO_x$ and $SO_x$ are often present. $CO_2$ concentration in the gas is usually in a range from 3% to 15% (molar) and $H_2O$ in the gas is usually in a range from 0.1% to 15%. The total molar concentration of $CO_2+H_2O$ is usually less than 25% when a stoichiometric combustion produces the stack gas and is usually less than 15% when dilution or excess air is employed in the process to limit the temperature in the higher temperature portion of the process. For example gas turbines use dilution air to limit the temperature of the combustion gas before it reaches the blades of a power turbine.

A thermal wave adsorption process, as described in Example 18 hereof, is employed to remove $CO_2$ from hot stack gas. The thermal wave adsorption process uses a parallel channel contactor to remove more than 70% of the $CO_2$ out of the stack gas, preferably more than 80% of the $CO_2$ out of the stack gas, even more preferably more than 90% of the $CO_2$ out of the stack gas and most preferably more than 95% of the $CO_2$ out of the stack gas. At least one $CO_2$ rich stream is produced in the process that has a purity such that it contains more than 70% $CO_2$, preferably more than 80% $CO_2$ and even more preferably more than 90% $CO_2$ and most preferably more than 95% $CO_2$.

This example illustrates a thermal wave process with sequential adsorption, desorption and cooling steps operated with three parallel contactor units. Those skilled in the art can construct several other potential embodiments of thermal wave process to remove $CO_2$ from flue gas using this example. Many of these embodiments involve the use of other numbers of contactors to construct a process.

Figure 15:
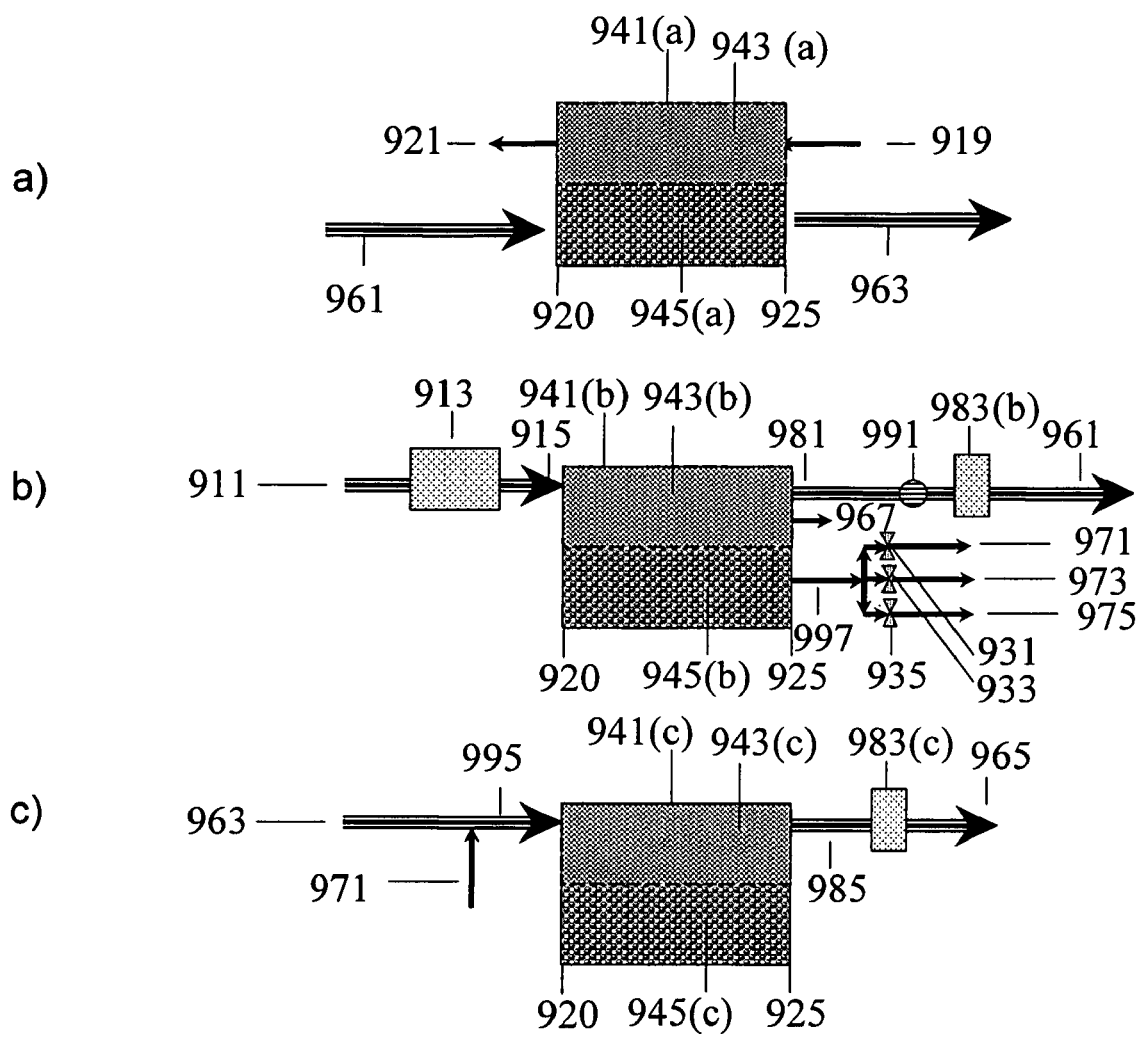
FIG. 15 hereof is a schematic representation of an embodiment of the present invention for treating a flue gas stream.

In the three unit operation of this example, one contactor undergoes an adsorption step while another contactor undergoes a desorption step and yet another contactor is being cooled. A diagram of the three unit process is shown in FIG. 15. FIG. 15(a) shows the streams flowing into and out of the contactor 941(a) during the adsorption step. FIG. 15(b) shows the streams flowing into and out of the contactor 941(b) during the desorption/regeneration step. FIG. 15(c) shows the streams flowing into and out of the contactor 941(c) during the contactor cooling step. The contactors 941(a), 941(b) and 941(c) are substantially similar. Properties of the contactors are similar to those discussed in Example 17 with each contactor having an array of heating/cooling channels 943 and adsorbent channels 945.

In this example, the adsorbent contains a microporous material. The microporous material is chosen so that at the temperature of the adsorption step in the process it adsorbs more than 0.25 milli-mole of $CO_2$ per $cm^3$ of adsorbent from an atmospheric gas mixture containing 90% $N_2$ and 10% $CO_2$. In a preferred embodiment the adsorbent contains at least a microporous material, such that at the temperature of the adsorption step in the process, it will adsorb more than about 0.75 milli-mole of $CO_2$ per $cm^3$ of adsorbent from an atmospheric gas mixture containing 90% $N_2$ and 10% $CO_2$. In a more preferred embodiment the adsorbent contains at least a microporous material such that, at the temperature of the adsorption step in the process, it will adsorb more than 1.5 milli-mole of $CO_2$ per $cm^3$ of adsorbent from an atmospheric gas mixture containing 90% $N_2$ and 10% $CO_2$. Depending upon design, the adsorption step can be conducted in a temperature range from about 5° C. to about 60° C., preferably in a temperature range from about 5° C. to about 45° C. and more preferably in a range from about 2° C. to about 35° C. The microporous material can be a zeolite such as zeolite 4A, 5A, 13X, NaX, and NaY. It is also within the scope of this invention that a hydrotalcite be used as the microporous material for the treatment of a flue gas stream. It is also possible for the microporous material to be made from a framework containing elements other than Si or Al, such as P. Another candidate adsorbent material is microporous carbon. Microporous sol-gel derived materials and silicas can also be candidate adsorbent materials. These materials can be used alone or in combination with other materials. It is preferred that the adsorbent in the contactor have low mesoporosity and microporosity. That is, the structured adsorbent contains less than about 20 vol. %, preferably less than about 15 vol. %, more preferably less than about 10 vol. %, and most preferably less than about 5 vol. % of their pore volume in open pores in the mesopore and larger size. As previously described, the low mesoporous and macroporous adsorbent can contain a blocking agent.

Regeneration of the adsorbent is done with heat contained in the stack gas and FIG. 15(*b*) shows the stream flow into and out of the contactor being regenerated 941(*b*). Stack gas 911 enters the "heating/cooling channel" (as opposed to the adsorbent channel) at the temperature at which it is produced which is in a range from about 150° C. to about 250° C. When the regeneration process starts the temperature of contactor 941(*b*) is in a range from about 2° C. to about 35° C. Before the stack gas 911 enters the contactor 941(*b*) the stream 911 can optionally be fed through a process block 913 that removes particulates. Several different methods to remove particulates can be used including filtration with ceramic candle filters, monolithic inorganic (metal or ceramic) filters, tubular metal filters, polymeric, or bag filters. Alternatively an electrostatic precipitator can be used to remove particulates. A stream 915 that is nearly at the same temperature of the stack gas 911 emerges from the optional process block 913 and enters the heating/cooling channels 943(*b*) of parallel channel contactor 941(*b*). At the start of the desorption step the microporous adsorbent material in the contactor contains adsorbed $CO_2$. It is preferred that at the beginning of the regeneration step (i.e. after the adsorption step is complete) the volume averaged $CO_2$ loading in the adsorbent be greater than about 0.25 milli-mole per $cm^3$ of adsorbent material. It is more preferred that the volume averaged $CO_2$ loading in the adsorbent be greater than 0.75 milli-mole per $cm^3$ of adsorbent material. In its most preferred embodiment the volume averaged $CO_2$ loading in the adsorbent would be greater than 1.5 milli-mole per $cm^3$ of adsorbent material. A specific example of loading in the most preferred range would be an average $CO_2$ loading of 1.7 milli-mole per $cm^3$ of the microporous adsorbent material. As the stream 915 begins to flow into the contactor 941(*b*), gas begins to flow out of the adsorption/cooling channels 943(*b*) forming stream 981. When the process starts stream 981 is at the initial temperature of the contactor. As a thermal wave of the type described in Example 18 moves through the contactor the temperature of stream 981 increases slightly. The temperature of stream 981 increases sharply when the thermal wave moves through the contactor. It is preferable not to terminate the desorption step before the thermal wave has moved through the contactor. If the thermal wave breaks through the contactor before the adsorption step (FIG. 15*a*) has been completed, then an additional thermal bed 983(*b*) can be employed to soak up heat until it is time to stop the adsorption, desorption/regeneration and contactor cooling steps. The thermal bed 983(*b*) can be a packed bed of solid particles through which a thermal wave also passes. If the thermal mass is a packed bed of solid particles its temperature at the start of the regeneration process is near that of the adsorbent bed.

It is preferable for the thermal front to break through the contactor before the adsorption, regeneration and cooling steps are terminated. To ensure that the thermal front breaks through the contactor, the total mass of the adsorbent layer and barrier wall between the adsorption channel and heating/cooling channel should be less than about 10 times the mass of the adsorbent materials, preferably less than about 5 times the mass of the adsorbent materials, even more preferably less than about 2 times the mass of the adsorbent materials and most preferably less than about 1.5 times the mass of the adsorbent materials.

As the thermal wave moves through the contactor being regenerated 941(*b*) water condenses out of the gas stream. Condensation occurs because the temperature of the gas falls as it passes along the contactor. The concentration of water vapor in gas stream 981 coming out of the heating/cooling channels 943(*b*) is nearly that for saturated gas at the temperature of stream 981 which can be more than about 100° C. lower than the stream 911 entering the regenerator. Because liquid water falls out of the stream 915 passing through the contactor being regenerated 941(*b*), it can be advantageous to align the contactor so that the gas flows downward and the liquid flows under action of gravity concurrently with the gas to the bottom of the contactor. An optional method can be provided to remove condensed water from the contactor to form water stream 967. Optionally a knockout 991 can be provided to remove any mist of liquid water flow coming out of the contactor. It is preferred that there is not a significant amount of liquid phase water flowing along with the cooled partially dehydrated flue gas stream 961.

In this example the gas passing through the heating/cooling channels of the contactor 943(*b*) moves in the same direction as gas passing through the adsorption channels 945(*a*) during the adsorption step (i.e. co-currently). This type of co-current thermal wave desorption process was described in detail in Example 17. Elements 920 and 925 as shown in FIG. 15, represent the inlet end and outlet end of the adsorption channels, respectively. In this example the microporous adsorbent is chosen such that $H_2O$ is a strongly adsorbed species, $CO_2$ is adsorbed somewhat less strongly, and $N_2$ and $O_2$ are weakly adsorbed. Examples of microporous materials that have this ordering of adsorption include zeolites such as zeolite 4A, 5A, 13X, NaX, and NaY. Trace materials such as $SO_x$ and $NO_x$ can be very strongly adsorbed. The following description of regenerator operation will apply to a contactor that was designed and operated to remove most of the $CO_2$ from the flue gas and the description will focus on the majority components in the flue gas. The process described will capture much of the $SO_x$ and $NO_x$ from the gas stream. It should be noted that it is possible to use the principles described in this example to remove $SO_x$ and $NO_x$ from gas streams in a process that captures less of the $CO_2$.

In the co-current thermal wave desorption process the least strongly adsorbed $N_2$ and $O_2$ species flow out of the contactor in the initial phase of the desorption process forming stream 997. It can be advantageous to divide the stream 997 coming out of the contactor into streams emerging at earlier versus later times, because streams emerging at different times will have different $CO_2$ and $H_2O$ concentrations and thus may preferably be processed in different manors. In an optional embodiment of the process valve 931 is opened at the start of the regeneration step allowing stream 977 to flow and form stream 971. Stream 971, recovered early in the regeneration, has very low $CO_2$ concentration. In the process shown in FIG. 15 hereof this stream is combined with stream 963 which is ultimately vented through a stack. As time progresses, the concentration of $CO_2$ in stream 971 begins to increase and valve 931 is closed to stop flow in stream 971. In this optional embodiment valve 933 is "simultaneously" opened to start flow in stream 973. The time at which these valves actuate sets the $CO_2$ purity in stream 973. Alternatively valve 933 was opened at the start of the regenerations process allowing stream 997 to flow and form stream 973. Stream 973 contains the majority of the $CO_2$ that was originally in the stack gas. The concentration of $CO_2$ in stream 973 is high enough that it can be sent to a sequestration process with little or no additional processing. In this example the stream is produced at atmospheric or slightly higher than atmospheric pressures. It is possible to design processes producing stream 973 from pressures ranging from vacuum to several (approximately 3) atmospheres. It is less desirable to produce stream 973 at sub-atmospheric pressures because this increases costs of compression in $CO_2$ sequestration processes.

Stream 973 can be sent to different types of $CO_2$ sequestration processes. Non-limiting examples include sending the $CO_2$ into underground formations such as aquifers with a top seal that prevents significant loss of injected acid gas components, oil reservoirs, gas reservoirs, depleted oil reservoirs and depleted gas reservoirs. Deep open storage is also a potential disposition for the $CO_2$, through purity requirements can be anticipated to be more stringent. Typically the separated $CO_2$ and $H_2S$ has to be compressed to pressures greater than about 2,000 psi and often to pressures greater than about 5,000 psi to be injected into these types of underground formations. Several properties of stream 973 make it suitable for compression in a sequestration process. These properties include the fact that its temperature is significantly below that of the stack gas and it is highly concentrated in $CO_2$. In some instances additional processing is required before stream 973 is sequestered. A non-limiting example of an additional processing step would be a more rigorous dehydration of the stream to mitigate potential corrosion in pipes and compressors used in the sequestration process. Towards the end of the regeneration process the $H_2O$ concentration in stream 973 increases. To minimize potential corrosion problems in equipment used to sequester $CO_2$ it can be advantageous to separate the stream coming out towards the end of the regeneration process and to handle this stream separately. In an optional embodiment when the $H_2O$ concentration in stream 973 increases above a desired threshold, valve 933 is closed and valve 935 is opened. This stops flow of stream 973 and starts flow of stream 975 that has a higher concentration of water. Stream 975 can then be dehydrated separately and then recombined with stream 971.

The cool partially dehydrated flue gas stream 961 coming out of the contactor being regenerated, 941(b), is sent to contactor 941(a) that is undergoing an adsorption step. The stream 961 is sent through the adsorption channels 945(a) of the contactor where a microporous adsorbent preferentially removes $CO_2$ and $H_2O$. Contactor 941(a) can optionally be constructed with several different microporous adsorbents along the length of the channels 945(a). In one embodiment where different microporous adsorbents are placed along the length of the channels 945(a), the adsorbent that is most selective for $H_2O$ is placed at the beginning of the channels. In this manner the water vapor partial pressure in the stream can be reduced allowing adsorbents towards the end of the channel to operate more effectively for $CO_2$ removal. Zeolites with large cation concentrations such as 4A, 5A, NaX are examples of microporous adsorbents that can operate more effectively when they are dry. The reason for this is that the $CO_2$ adsorption isotherm of zeolites with large cation concentrations tends to increase when the zeolite is dry (i.e. the $CO_2$ isotherm of a dry cationic zeolite usually lies above a wet zeolite). Materials that can be used to remove water include silica, alumina, carbons, and zeolites.

In this example a single type of microporous adsorbent lines the adsorbent channels 945(a). At the start of the adsorption process the temperature of the contactor 941(a) is the same as that produced at the end of the cooling step in FIG. 15(c). This temperature is slightly above that of the ambient air in the atmosphere. As the adsorption step begins $CO_2$ and $H_2O$ are selectively taken up by the adsorbent near the front end of the contactor 921. The concentration of $CO_2$ and $H_2O$ in the remaining portion of the adsorbent is low and nearly equal to that at the end of the regeneration step in FIG. 15(b) and the $CO_2$ concentration of gas stream 963 coming out of the contactor 941(a) is less than 5% of that in the flue gas stream 911.

In this example the microporous adsorbent has the property that $H_2O$ is more strongly adsorbed than $CO_2$. An example of a microporous zeolite adsorbent with this property is zeolite 5A. For this zeolite as well as any other microporous adsorbent the temperature increases when molecules are adsorbed. The temperature rise is determined by the heat of adsorption of the sorbed species, the amount adsorbed, the thermal conductivity in the contactor, and the thermal mass of the contactor. An optional stream 919 can be flowed through the contactor to limit the temperature rise in the contactor. Stream 919 is derived from the ambient air and is blown through the heating/cooling channels 943(a) of the contactor. In the embodiment shown in FIG. 15(a) it moves counter-currently to stream 961 that flows through the adsorption channels. The stream 919 removes heat generated by the heat of adsorption and forms stream 921 exiting the contactor that carries away most of this heat. In a different embodiment this optional stream 919 can flow co-currently with stream 961.

As the adsorption step continues relatively sharp concentration fronts in the adsorbed phase concentration (i.e. adsorbates in the microporous material lining the channel) move along the length of the contactor. The concentration front for $H_2O$ is closer to the entrance of the adsorber channel than that for $CO_2$. The way in which they move with time down the length of the adsorber channel is referred to as concentration waves. With time these waves or fronts advance along the length of the adsorption channel. As these waves advance, the $CO_2$ concentration in the outlet stream 963 remains low until $CO_2$ front reaches the end of the contactor 925. At this point in time the $CO_2$ concentration in the outlet stream 963 begins to rise and the adsorption step is stopped.

The cool stream 963 (with the $CO_2$ removed) is routed to a contactor 941(c) that has been regenerated and is undergoing a cooling step. Additional cool gas produced in the regeneration process (stream 971) can optionally be added to stream 963 to form stream 995. This stream 995 is introduced into the heating/cooling channels of the contactor 941(c). At the start of the cooling step contactor 941(c) is near the temperature of the flue gas stream 911. As stream 995 begins to flow through the contactor a cooing thermal wave develops. This cooling wave is such that the temperature of the contactor near the inlet side 920 is low and at a sharp front located further along the length of the contactor the temperature rises abruptly. The gas exiting the contactor 985 remains hot as the thermal wave advances across the contactor. If an optional thermal mass 983 is used in the regeneration step then the gas stream 985 can also be passed through the thermal mass 983(c). When a thermal mass is used in the process the thermal wave breaks through the end of the contactor and cools the thermal mass before the cooling process is terminated. In this optional embodiment the gas stream exiting the thermal mass 965 remains hot during the majority of the cooling step. The hot gas stream 965 is substantially free of $CO_2$ and can be vented or sent up a stack. The cooling step is terminated simultaneously with the adsorption and regeneration steps. Throughout the cooling step there is no flow out of the adsorbent channels 945(c).

Example 18

Another important gas separation technique is temperature swing adsorption (TSA). TSA processes also rely on the fact that under pressure gases tend to be adsorbed within the pore structure of the microporous adsorbent materials, or within the free volume of a polymeric material. When the temperature of the adsorbent is increased, the gas is released, or desorbed. By cyclically swinging the temperature of adsorbent beds, TSA processes can be used to separate gases in a mixture when used with an adsorbent that selectively picks up one or more of the components in the gas mixture.

TSA has the advantage that adsorption isotherms are strongly influenced by temperature. Thus, very high purities can be obtained by adsorbing at low temperature (where adsorption is strong) with the release of a strongly held specie being possible by means of high temperature for desorption. Also, compared to pressure swing adsorption, TSA can be operated in the saturation regime of the isotherm, a significant advantage for capacity and range of utility with zeolitic adsorbents.

However, TSA as practiced has several disadvantages. In directly-heated TSA processes, a hot fluid is typically flowed through the adsorption bed to raise the adsorbent temperature. The greater the temperature rise, the more fluid is needed. The desorbed impurities thus end up dispersed in a large volume of heating fluid, and the large amount of heat that is used to raise the adsorbent temperature is often not recovered. In some cases the heat is not recovered because many directly-heated TSA systems are operated with long adsorption times, sometimes over 24 hours, and much shorter regeneration times. Finally, the occasional and gradual regeneration gives rise to concentration and flow variations in downstream equipment that can be difficult to manage in an otherwise steady state process plant. In indirectly-heated TSA systems, the heat can be supplied with a heat exchanger, avoiding dilution of the product with a heated purge gas. However, heat management and the cyclic nature of indirectly heated TSA processes often presents difficulties.

This example illustrates a TSA system that enables chromatographic-like separation of a multi-component feed into several streams each concentrating different species. This chromatographic-like separation will be referred to as "Temperature Wave Adsorption" (TWA).

TWA is a TSA process that uses indirect heating (i.e., it does not dilute the desorbed materials into a heating medium). In its simplest embodiment, one set of channels in a contactor contains an adsorbent and another set of channels is used to bring heat into and take heat out of the contactor. In a preferred embodiment, the heat adding/removing channels are designed in a manner that results in a thermal wave moving along the length of the channels in heating and cooling steps of the TSA process. FIGS. 7 and 9 show two parallel channel contactor configurations that are suitable for use in this preferred TWA embodiment. In FIG. 7 channels between 223 and 225 act as heating/cooling channels and channels 203 act as adsorption channels. In FIG. 9 channels between 423 and 425 act as heating/cooling channels and channels 403 act as adsorption channels.

To maximize the TWA effect, it is desirable to have a sharp thermal front move along the length of the channel during the adsorption and cooling steps. In order to do this the contactor must act as an efficient heat exchanger, rapidly transferring heat between a fluid heat transfer medium flowing in the heating/cooling channels and the adsorbent in the adjacent channels. The fluid heat transfer medium can be a liquid, a gas or a slurry. The heat transfer coefficient between fluid flowing in the heating/cooling channel and the adsorbent is set in part by the dimensions of the flow channels. In one embodiment of the present invention, the heat exchange channels are characterized in terms of the boundary between the feed-containing channel and the channels containing heating/cooling medium. That boundary can be characterized as having a cross-sectional area (A) and a perimeter (P). A parameter D can be calculated as 4A/P. For example, for cylindrical tubes packed with adsorbent pellets, D will equal the tube diameter. In a preferred embodiment of the present invention, the parameter D for the channels that contain adsorbent is less than 1 inch, and more preferably D is less than ½ inch.

By recording the time dependence of the temperature of the fluid emerging from the heating/cooling channels, it is possible to determine whether a thermal wave has moved through the contactor and the sharpness of the thermal front. The time delay before the temperature begins to change provides a measurement of the velocity of the thermal wave and the rate at which the temperature changes provides a measurement of the sharpness of the front. The needed data can be acquired from a thermocouple placed in the fluid stream emerging from the heat exchange channels. One way to characterize the velocity of the thermal front is to measure $t_{delay}$, the time it takes from when the fluid begins to flow at a steady rate to the point that the temperature at the outlet has risen to 25% of its final steady state value. The rate of rise can be characterized by measuring $t_{rise}$; the time it takes the temperature at the outlet to rise from 25% to 75% of its final, steady-state value. It is preferred that the ratio $t_{delay}/t_{rise}$ be greater than 2, preferably greater than 5, more preferably greater than 10 and even more preferably greater than 50.

Shorter cycle times provide the most compact and productive use of adsorbent, but also require the highest heat transfer coefficients. Methods for achieving high heat transfer coefficients in heat exchangers are well known in the art.

When the contactor containing the heat exchange/adsorber system is designed with good heat transfer and thermal conduction characteristics, a sharp temperature wave will be created during heating and cooling steps. Such a condition enables the system to achieve the second object of this invention, which is to substantially recuperate and recover the heat required to temperature-swing the bed. This, in turn, enables the potential use of very high desorption temperatures that would not normally be considered for TSA operation. In the desorption step, the thermal wave can be used to produce a chromatographic effect that enables multicomponent separation.

Before the desorption step begins molecules are preferentially adsorbed in the micropores or free volume of an adsorbent within the adsorbent channel. These molecules are preferentially taken up in the adsorption step where a multicomponent feed flows through a relatively cool adsorbent channel. The temperature of the channel at this point is significantly below the temperature that will be used to regenerate the adsorbent. It is preferred that the adsorption channels of the parallel channel contactor are designed so that the concentration gradients along the length of the channel formed during the adsorption step are relatively sharp. Sharp gradients are preferred because they enable feed to be passed through the bed for a long time before "breakthrough" of adsorbate occurs. If mass transfer is not adequate, then the gradient will be shallow. Such a condition results in adsorbate beginning to escape the bed long before the bed's capacity to adsorb is well utilized. In practice, high mass transfer is achieved by providing relatively small channels for the feed fluids to travel through. This is accomplished using beds of small adsorbent particles or using parallel channel contactors with small channel sizes. In a preferred embodiment, a space-filling adsorbent covers the walls of adsorbent channels in a parallel-channel contactor leaving a hydraulic radius for fluid flow that is less than 1 inch, preferably less than 0.25 inches, and more preferably less than 0.1 inches. A thermal wave separation can be created with adsorbents that do not have low mesoporosity and microporosity, but to obtain the highest possible recovery and purity, it is preferred to use an adsorbent with low mesoporosity and microporosity. That is, the structured adsorbent contains less than about 20 vol. %, preferably less than about 15 vol. %, more preferably less than about 10 vol. %, and most preferably less than about 5 vol. % of their pore volume in open pores in the mesopore and larger size.

When feed enters the adsorbent channel at the start of the adsorption step, the adsorbent is relatively cool and molecules are taken up by the adsorbent near the point at which feed is introduced. The adsorbate concentration is high in the early part of the bed or layer, and at low concentration in the downstream part of the bed or layer. Ideally, there is a sharp gradient of adsorbate concentration along the length of the adsorbent channel. As operation proceeds, this concentration front moves along the length of the adsorbent channel. The dividing line between high concentration and low concentration zones gradually moves towards the bed exit as adsorbate accumulates in the adsorbent bed or layer.

With a feed for which many different components are selectively taken up by the adsorbent, it is possible to have multiple concentration fronts move along the length of the adsorbent. Due to either strength of adsorption, or differences in diffusion coefficients between different species in the feed, the adsorbent will preferentially take up different feed components. The most preferred components will be referred to as the strongest-adsorbing components. The less preferred components will be referred to as the weakly-adsorbed components. During adsorption, the strongest-adsorbing components will occupy the regions of adsorbent closest to the inlet and will displace weakly-adsorbed materials from that region. Over the period of adsorption, the adsorbates will order themselves from strongest to weakest as one moves from inlet to outlet of the adsorption channels. This type of patterning can occur for gaseous as well as liquid feeds, and TWA processes can be designed to operate with either type of feed. For the purpose of this example, a gaseous feed will be considered.

Figure 16:
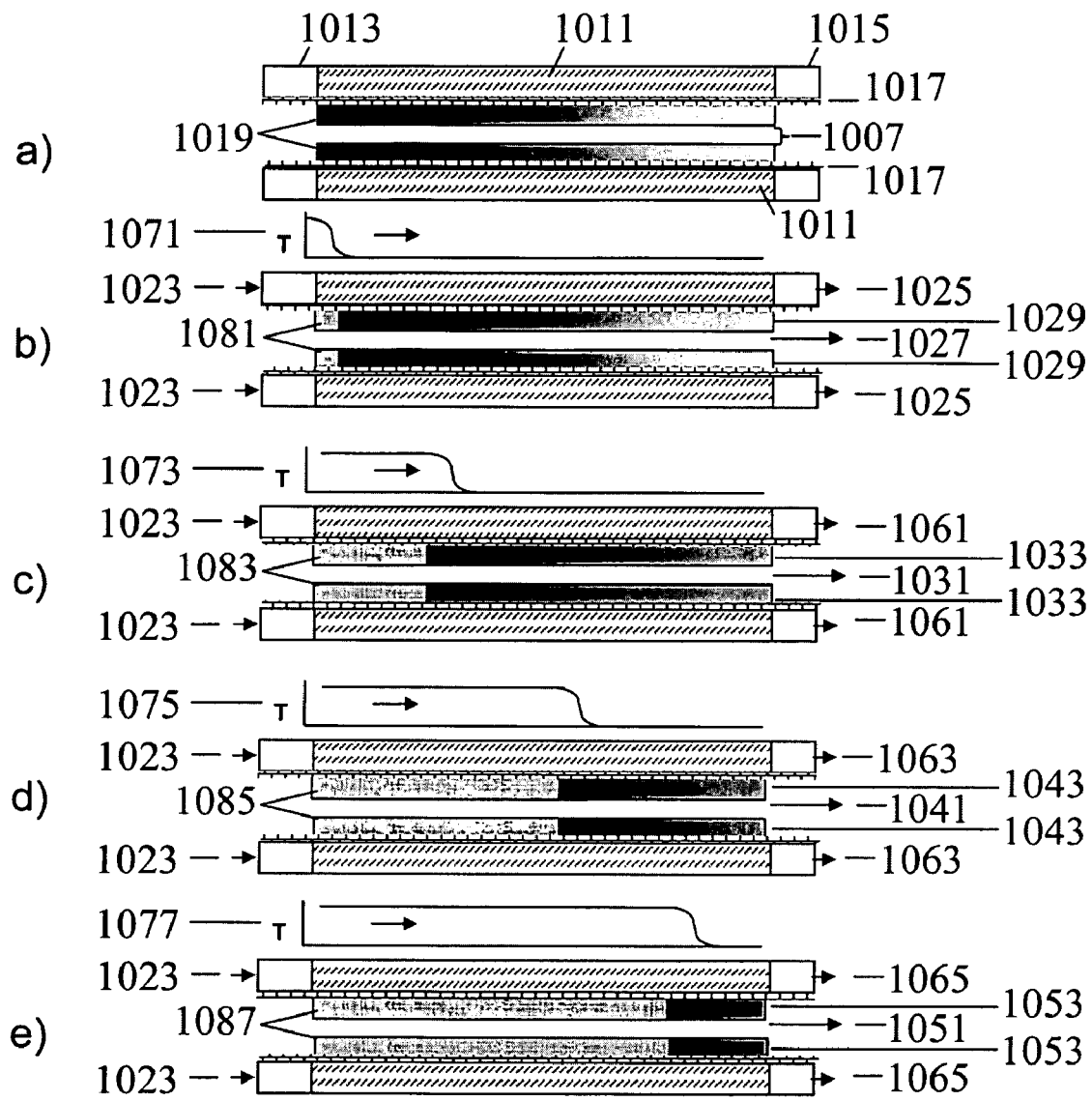
FIG. 16 hereof is a schematic representation of an embodiment of the present invention that enables chromatographic-like separation of a multicomponent feed into several streams each concentrating different species. This chromatographic-like separation is referred to as "Temperature Wave Adsorption" (TWA).

FIG. 16(*a*) shows schematically the patterning of adsorbates deposited along the length of the adsorbent layer 1019 at the end of an adsorption step for a multicomponent feed. The strongly-adsorbed species are shaded a darker gray than the less strongly-adsorbed species. Layer 1019 would correspond to layer 205 in FIG. 7 and layer 405 in FIG. 9. A diffusion barrier 1017 acts as a wall separating molecules in the feed channel 1007 from those in the heating/cooling channel 1011. The wall separating the feed and heating/cooling channel 1017 would correspond to 219 in FIG. 7 and 415 in FIG. 9. The adsorbent channel 1007 would correspond to 203 in FIG. 7 and 403 in FIG. 9. The heating/cooling channel 1011 would correspond to channels running from 223 to 225 in FIG. 7 and from 423 to 425 in FIG. 9.

In the adsorption step the feed flowed in the direction from contactor end 1013 to the end 1015. As such the strongly-adsorbed species were deposited closest to the end 1013. More weakly-adsorbed species were deposited closer to the end 1015. In this example the flow of the hot fluid in the desorption occurs in the same direction as feed that was flowed during the adsorption step. This is referred to as performing the adsorption and desorption in a co-current fashion. It should be noted that a TWA process can also be constructed with the adsorption and desorption steps occurring in a counter-current fashion.

FIG. 16(*b*) shows the state of the channels at the beginning of the desorption step. At this point in time hot, fluid has begun to flow in the heating/cooling channel, with a hot stream flowing in from 1023 and a cold stream 1025 flowing out. A thermal wave 1071 has begun to advance along the contactor. In this example there is very good thermal conductivity in the contactor, and the temperature of the adsorbent layer closely follows the temperature of the heating/cooling channel. In this example there is no imposed gas flow in the adsorbent channel 1007. A gas flow can optionally be added at any point in the desorption step to aid in the removal of molecules from the adsorbent channel 1007. At this early stage most of the adsorbate has been removed from the adsorbent layer in the lightly shaded region labeled 1081. Molecules have been released from the region of the adsorbent layer 1081 because its temperature has increased and adsorption isotherms are strongly influenced by temperature. The entrance end of the adsorption flow channel is valved off and desorbed molecules move down the adsorption channel to form stream 1027 that flows out of the contactor. As such the strongly-adsorbed species move down the adsorption channel 1007 towards end 1015. As they move down the channel, they are reabsorbed in the adsorbent layer (in some instances displacing the most weakly, weakly, and less-strongly-adsorbed species). The concentration of the strongly-adsorbed species in the shaded region of the adsorbent 1029 is then increased. Gas that is displaced into the stream 1027 flowing out of channel 1007 is preferentially enriched in the most-weakly-adsorbed species. With a time actuated valve this gas stream 1027 can be separated from gas that evolves at later stages of the desorption step.

FIG. 16(*c*) shows the state of the channels at a later stage of the desorption step. At this point in time more hot fluid has flowed through the heating/cooling channels. A hot stream continues flowing in from 1023 and a cold stream 1061 flows out of the contactor. The temperature of this cold stream 1061 is slightly different from that of stream 1025 that was flowing out of the of the contactor at the earlier time shown in FIG. 16(*b*). The thermal wave 1073 has advanced further along the contactor. More of the strongly-adsorbed molecules have been displaced from the adsorbent layer 1083 because its temperature over a longer length has increased. The entrance end of the adsorption flow channel remains valved off and desorbed molecules move down the adsorption channel to form stream 1031 that flows out of the contactor. As the strongly-adsorbed molecules move down the channel they continue to re-adsorb in colder region of the adsorbent layer 1033 and in some instances displace the most weakly, weakly, and less-strongly adsorbed species. The concentration of the strongly-adsorbed species in the shaded colder region of the adsorbent 1033 is thus increased. Gas that is displaced into the stream flowing out of channel 1033 is preferentially enriched in the weakly-adsorbed species. With a time-actuated valve, this gas stream 1033 can be separated from gas that evolves at later stages of the desorption step.

FIG. 16(*d*) shows the state of the channels at an even later stage of the desorption step. At this point in time even more hot fluid has flowed through the heating/cooling channels. A hot stream continues flowing in from 1023 and a cold stream 1063 flows out of the contactor. The temperature of this cold stream (1063) is slightly different from that of stream 1061 that was flowing out of the contactor at the earlier time shown in FIG. 16(*c*). The thermal wave 1075 has advanced further along the contactor. More of the strongly bound molecules been removed from the adsorbent layer and the lightly shaded region labeled 1085 and this region (1085) has grown with respect to the region 1083 at the earlier time shown in FIG. 16(*c*). More strongly-bound molecules have been displaced from the adsorbent layer in region 1085 because its temperature over a longer length has increased. The entrance end of the adsorption flow channel remains valved off and desorbed molecules move down the adsorption channel. As the strongly-bound molecules move down the channel they continue to reabsorb in colder region of the adsorbent layer 1043 and in some instances displace the remaining most weakly, or weakly-adsorbed species as well as less strongly-adsorbed species. The concentration of the strongly-adsorbed species in the shaded colder region of the adsorbent 1043 is thus increased. Gas that is displaced into the stream flowing out of channel 1041 is preferentially enriched in the less strongly-adsorbed species. With a time-actuated valve this gas stream 1041 can be separated from gas that evolves at later stages of the desorption step.

FIG. 16(*e*) shows the state of the channels at an even later stage of the desorption step. At this point in time even more hot fluid has flowed through the heating/cooling channels. A hot stream continues flowing in from 1023 and a cold stream 1065 flows out of the contactor. The temperature of this cold stream (1065) is slightly greater than that of stream 1063 which was flowing out of the contactor at the earlier time shown in FIG. 16(*d*). The thermal wave 1077 has advanced further along the contactor. More of the strongly-bound molecules been removed from the adsorbent layer and the lightly-shaded region labeled 1087 and this region (1087) has grown with respect to the region 1085 at the earlier time shown in FIG. 16(*d*). More strongly-bound molecules have been displaced from the adsorbent layer in region 1087 because its temperature over a longer length has increased. The entrance end of the adsorption flow channel remains valved off and desorbed molecules move down the adsorption channel. As the strongly-bound molecules move down the channel they continue to re-adsorb in colder region of the adsorbent layer 1053 and in some instances displace the remaining most weakly, weakly-adsorbed species and less strongly adsorbed species. The concentration of the strongly-adsorbed species in the shaded colder region of the adsorbent 1053 is thus increased. Gas that is displaced into the stream flowing out of channel 1051 is preferentially enriched in the most stronglyadsorbed species. The desorption step is ended near the time (i.e., before or after) the thermal front breaks through the end of the contactor.

It is preferred that adsorption, desorption and cooling steps be performed sequentially in a TWA process. An advantage of this operation is that the heat used to swing the contactor is retained in the heat transfer medium. If adsorption was to proceed simultaneously with cooling, then a substantial part of the heat in the bed will be lost to the adsorbate-free feed, and a higher heat load will be needed to restore the high temperature of the heat transfer medium To provide a continuous operation the TWA system operating with sequential adsorption, desorption and cooling steps, the process may be operated with two or more contactor units. For a three-unit operation, one unit can undergo an adsorption step while another unit undergoes a desorption step while yet another unit is being cooled. It is preferable to cool the unit by passing cool fluid through the heating/cooling channel of the contactor in a manner such that a thermal (cooling) wave moves through the contactor. While the thermal wave moves through the contactor, a hot fluid will emerge from the end of the contactor. The cooling step is ended near the time (i.e. before or after) the thermal front breaks through the end of the contactor. As such it is possible to design a process in which hot fluid emerging from a contactor that is being cooled is routed to supply heat to a contactor that is undergoing desorption. Similarly cool fluid emerging from a contactor that is undergoing a desorption step can be routed to feed cooling fluid to a contactor that is undergoing a cooling step. In this manner, or variations of this manner that would be known to those skilled in the art, a continuous process can be constructed.

In practice it may be necessary add or subtract heat from fluid (heat transfer medium) streams flowing between contactors. For example, due to heat loses from desorbed material leaving the system hot, some heat may be added to "top off" the temperature of the hot fluid heat transfer medium. Cooling may also need to be provided to decrease the cooling fluid temperature to a temperature lower than that of the incoming feed, thus pre-cooling the adsorbent to a temperature below the incoming separation feed temperature.

Several other thermal process integrations can be used to control the thermal wave. The timing of the adsorption and desorption steps can be varied by adding a heat storage medium between either the adsorption and desorption step, or the desorption and adsorption step. The heat storage medium is configured so that a thermal wave will pass through the medium. An example is a packed bed heat exchanger. The time for a thermal wave to pass though this medium allows one to adjust the timing of the thermal waves in the adsorption and desorption steps. In addition, in many cases (particularly for impurity removal) the time required for adsorbent regeneration may be shorter than the time required for the contactor's adsorption capacity to be fully utilized. In such cases, it may be desirable to have several contactors undergoing the adsorbing step, while two paired contactors are in the heat/ regen (desorption) phase and the re-cooling phase. In a preferred embodiment, the several contactors engaged in adsorption are connected in serial fashion, such that the mostrecently regenerated contactor unit is the last bed in line, and the first unit in line will be next to be regenerated. In another preferred embodiment, the contactors undergoing the adsorption step are connected in parallel, such that that adsorbent in each unit treats a fraction of the whole feed. In yet another embodiment, thermal wave storage devices are used to store and allow proper timing of the cycles.

When the contactors are used in this manner, it is acceptable for each HX-Adsorber unit to be oriented in co-flow, counter-flow, cross-flow, or other configuration. However, in a preferred embodiment, the contactors are used in co-flow and/or counter-flow orientation.

Several hybridized processes that combine a thermal wave process with either a pressure swing or partial pressure displacement process can be created. A thermal wave process can be combined with pressure swing to make a hybridized thermal wave/pressure swing process that produces a multi-component separation while facilitating the desorption of strongly held species. A thermal wave process can be combined with a partial pressure displacement process to make a hybridized thermal wave/partial pressure displacement process that can be run with liquid feeds.

With multi-component feeds such as natural gas it can be advantageous to employ a thermal wave separation. Natural gas usually has several different impurities and the thermal wave process provides a method to produce several different product streams each enriched with a different impurity. Examples of impurities that can be removed with a thermal wave separation process include $H_2S$, COS, mercaptans, $CO_2$, nitrogen, water, heavy hydrocarbons, and some Hg compounds. When the thermal wave separation is used for heavy hydrocarbon recovery it is possible to directly produce separate streams enriched with different hydrocarbon fractions. In all of these separations the methane is the light (poorly adsorbed) component and the impurities are taken up in the adsorption step. The adsorption can involve either a kinetic or equilibrium separation. The methane is thus produced at or near the feed pressure. Because the thermal desorption step can occur at a higher pressure than would be possible in a PSA process the adsorbed impurities can be recovered at relatively high pressures. The thermal wave process can also be used to separate nitrogen out of LNG boil off LNG flash gas and regassified LNG. In other applications a thermal wave process can be used to separate, concentrate, and pressurize $CO_2$ captured from flue gas, or oxygen captured from air. As a multi-component separation system, it could form the basis for a compact and non-cryogenic steam cracker back-end. The invention can replace PSA and distillation anywhere those processes are used with reversibly-absorbable molecules whose isotherms are temperature sensitive.

In one embodiment of the present invention, a series of cross-flow contactors is used to create a parallel channel contactor that has separate and parallel adsorption and heating channels. It is well known in chemical engineering art that a plug flow reactor can be approximated by connecting a large number of perfectly-stirred reactors in series. We have discovered that a plug flow channel system that is in parallel orientation with a second plug-flow channel system can be approximated using a series of cross-flow heat-exchange contactors. Cross-flow contactors have two sets of channels, with each set of channels having fluid flow at a 90° orientation to the other set. For example, a cross flow heat exchanger has many high-conductivity (typically metal) plates that are stacked with a gap in between one plate and the next. The series of plates defines a series of gaps that may be numbered from first to last. In a cross-flow heat exchanger, the odd-numbered gaps would constitute one set of channels and would carry a fluid traveling in one direction. The even numbered gaps would constitute the second set of channels and would carry a different fluid traveling in a direction 90° rotated from the first fluid. This cross-flow arrangement is convenient for fabrication. In the present embodiment, the parallel channel contactor is created by using a number of cross-flow contactors, by connecting the first set of channels of each contactor in series fashion, and by connecting the second set of channels of each contactor in the identical series order. Connected in this fashion, the two resulting channel systems can be operated in co-flow or counter-flow orientation.

In one embodiment of the present invention, an adsorbent is coated in one or both sets of channels of a series of cross flow heat exchangers. In a preferred embodiment the adsorbent has a low volume of mesopores and macropores. When the adsorbent is coated on one set of channels of the heat exchanger elements, the series connection is such that the heating or cooling in of one set of channels is coupled with adsorption or desorption in the other set of channels. The system of cross-flow heat exchangers connected in series approximates the behavior of a parallel channel contactor and can be used in similar fashion. When the heating/cooling channels are used in a fashion that generates a thermal wave, only a small part of that wave will manifest itself in any single cross-flow contactor. Because the exchanges are coupled in series a thermal wave can propagate along the series of exchangers (or stack of exchangers).

What is claimed is:

1. An adsorbent contactor for use in swing adsorption gas separation process units, comprising:
   a) a gas inlet end; and
   b) a gas outlet end;
   wherein the gas inlet end and the gas outlet end are in fluid connection by a plurality of open flow channels wherein the surface of the open flow channels are comprised of an adsorbent material that has a selectivity for a first gas component over a second gas component of a gas mixture greater than 5, and wherein the contactor has less than about 20% of its open pore volume in pores with diameters greater than about 20 angstroms and less than about 1 micron; and
   wherein the open pore volume (in volume percentage) is defined as the volume of the pores in the adsorbent that are between 20 angstroms and 1 micron in diameter divided by the total volume of the adsorbent contactor that is occupied by the adsorbent material including associated mesopores and macropores in the adsorbent structure; and the adsorbent contactor is comprised of substantially parallel channels wherein the geometry of the adsorbent contactor is selected from monoliths, a plurality of tubular members, stacked layers of adsorbent sheets with or without spacers between each sheet, multi-layered spiral rolls, bundles of hollow fibers, and bundles of substantially parallel solid fibers.

2. The adsorbent contactor of claim 1 wherein the adsorbent material has a selectivity for $CO_2$ over $CH_4$ greater than 5.

3. The adsorbent contactor of claim 1 wherein the adsorbent material has a selectivity for $N_2$ over $CH_4$ greater than 5.

4. The adsorbent contactor of claim 1 wherein the adsorbent material has a selectivity for $H_2S$ over $CH_4$ greater than 5.

5. The adsorbent contactor of claim 1 wherein the adsorbent material is comprised of a structured microporous adsorbent selected from the group consisting of zeolites, titanosilicates, ferrosilicates, stannosilicates, aluminophosphates (AlPOs), silicaaluminophosphates (SAPOs) and carbon molecular sieves.

6. The adsorbent contactor of claim 1 wherein the adsorbent material is comprised of a zeolite selected from the group consisting of MFI, faujasite, MCM-41 and Beta.

7. The adsorbent contactor of claim 1 wherein the adsorbent material is comprised of an 8-ring zeolite with a Si to Al ratio of about 1:1 to about 1000:1.

8. The adsorbent contactor of claim 7 wherein the 8-ring zeolite is DDR.

9. The adsorbent contactor of claim 7 wherein the 8-ring zeolite is selected from Sigma-1 and ZSM-58.

10. The adsorbent contactor of claim 1 wherein the adsorbent contactor is comprised of a first adsorption zone comprising a first adsorbent material which is in fluid contact with a second adsorption zone comprising a second adsorbent material, wherein the composition of the first adsorbent material is different from the composition of a second adsorbent material.

11. The adsorbent contactor of claim 10 wherein the first adsorbent material has a selectivity for the first gas component of a gas mixture over a second gas component of the gas mixture greater than 5; the second adsorbent material has a selectivity for a third gas component over the second gas component of the gas mixture greater than 5; and the second adsorbent material has a greater adsorption uptake for the third gas component than the first adsorbent material.

12. The adsorbent contactor of claim 11 wherein the first gas component is $CO_2$, the second gas component is $CH_4$ and the third gas component is $H_2S$.

13. The adsorbent contactor of claim 11 wherein the first gas component is $N_2$, the second gas component is $CH_4$ and the third gas component is $H_2S$.

14. The adsorbent contactor of claim 11 wherein at least one adsorbent material is comprised of a material selected from the group consisting of zeolites, titanosilicates, ferrosilicates, stannosilicates, aluminophosphates (AlPOs), silicaaluminophosphates (SAPOs) and carbon molecular sieves.

15. The adsorbent contactor of claim 11 wherein the at least one adsorbent material is comprised of an 8-ring zeolite that has a Si to Al ratio of about 1:1 to about 1000:1.

16. The adsorbent contactor of claim 15 wherein the 8-ring zeolite is DDR.

17. The adsorbent contactor of claim 15 wherein the 8-ring zeolite is selected from Sigma-1 and ZSM-58.

18. The adsorbent contactor of claim 1 wherein the adsorbent contactor has less than about 15% of its open pore volume in pores with diameters greater than about 20 angstroms and less than about 1 micron.

19. The adsorbent contactor of claim 1 wherein the adsorbent material also contains an effective amount of a thermal mass material having a higher capacity for adsorbing heat than the adsorbent material.

20. The adsorbent contactor of claim 1 wherein the adsorbent material has both mesopores and macropores and wherein at least some of the mesopores and macropores are occupied with a blocking agent of an effective size that is small enough to fit into a mesopore but too large to fit into a micropore of the adsorbent material.

21. The adsorbent contactor of claim 20 wherein the blocking agent is selected from the group consisting of polymers, microporous materials, solid hydrocarbons, and liquids.

22. The adsorbent contactor of claim 1 wherein the parallel flow channels have a channel gap from about 5 to about 1000 microns.

23. The adsorbent contactor of claim 1 wherein the ratio of adsorbent volume to flow channel volume is from about 0.5:1 to about 100:1.

* * * * *